(12) United States Patent
Chen et al.

(10) Patent No.: US 11,035,000 B2
(45) Date of Patent: Jun. 15, 2021

(54) METHODS AND COMPOSITIONS FOR ENRICHING NON-HOST SEQUENCES IN HOST SAMPLES

(71) Applicant: University of Alaska Fairbanks, Fairbanks, AK (US)

(72) Inventors: Jiguo Chen, Fairbanks, AK (US); Fang Ge, Fairbanks, AK (US)

(73) Assignee: UNIVERSITY OF ALASKA FAIRBANKS, Fairbanks, AK (US)

( * ) Notice: Subject to any disclaimer, the term of this patent is extended or adjusted under 35 U.S.C. 154(b) by 833 days.

(21) Appl. No.: 15/101,590

(22) PCT Filed: Dec. 4, 2014

(86) PCT No.: PCT/US2014/068644
§ 371 (c)(1),
(2) Date: Jun. 3, 2016

(87) PCT Pub. No.: WO2015/085105
PCT Pub. Date: Jun. 11, 2015

(65) Prior Publication Data
US 2016/0304953 A1  Oct. 20, 2016

Related U.S. Application Data

(60) Provisional application No. 61/911,642, filed on Dec. 4, 2013.

(51) Int. Cl.
*C12Q 1/6874* (2018.01)
*C12Q 1/6806* (2018.01)
*C12Q 1/6888* (2018.01)
*C12N 15/10* (2006.01)

(52) U.S. Cl.
CPC ....... *C12Q 1/6874* (2013.01); *C12N 15/1003* (2013.01); *C12Q 1/6806* (2013.01); *C12Q 1/6888* (2013.01)

(58) Field of Classification Search
CPC ............ C12Q 2525/173; C12Q 1/6806; C12Q 2537/159
See application file for complete search history.

(56) References Cited

U.S. PATENT DOCUMENTS

| 5,525,471 | A | | 6/1996 | Zeng | |
|---|---|---|---|---|---|
| 5,888,751 | A | * | 3/1999 | Tureci | ................ C07K 14/4748 435/6.14 |
| 2009/0170717 | A1 | | 7/2009 | Agan et al. | |
| 2013/0020998 | A1 | | 1/2013 | Howard | |

FOREIGN PATENT DOCUMENTS

WO  WO-2015/085105 A1  6/2015

OTHER PUBLICATIONS

Accession No. rs145884404 [database on-line][retrieved on Mar. 14, 2019] Retrieved from: https://www.ncbi.nlm.nih.gov/projects/SNP/snp_ref.cgi?do_not_redirect&rs=rs145884404 (Year: 2019).*
Accession No. rs9325224 [database on-line][retrieved on Mar. 14, 19] Retrieved from: https://www.ncbi.nlm.nih.gov/projects/SNP/snp_ref.cgi?rs=9325224 (Year: 2019).*
Alter, H. J., Stramer, S. L. & Dodd, R. Y. Emerging infectious diseases that threaten the blood supply. Semin Hematol 44, 32-41 (2007).
Chen, J. Serial analysis of binding elements for human transcription factors. Nat Protoc 1, 1481-1493 (2006).
Consortium, E. P. et al. An integrated encyclopedia of DNA elements in the human genome. Nature 489, 57-74, doi:10.1038/nature11247 (2012).
Djebali, S. et al. Landscape of transcription in human cells. Nature 489, 101-108, Nature. 11233 (2012).
Dobin, A. et al. STAR: ultrafast universal RNA-seq aligner. Bioinformatics 29, 15-21, doi: 10.109 3/bioinformatics/bts635 (2013).
Feng, H. et al. Human transcriptome subtraction by using short sequence tags to search for tumor viruses in conjunctival carcinoma. J Virol 81, 11332-11340 (2007).
Feng, H., Shuda, M., Chang, Y. & Moore, P. S. Clonal integration of a polyomavirus in human Merkel cell carcinoma. Science 319, 1096-1100, doi:10.1126/science.1152586 (2008).
Gerhard, D. S. et al. The status, quality, and expansion of the NIH full-length cDNA project: the Mammalian Gene Collection (MGC). Genome research 14, 2121-2127, doi: 10.1101gr.2596504 (2004).
Glenn, T. C. Field guide to next-generation DNA sequencers. Mol Ecol Resour 11, 759-769, doi:10.1111/j.1755-0998.2011.03024.x (2011).
Gonzalez-Porta, M., Frankish, A., Rung, J., Harrow, J. & Brazma, A. Transcriptome analysis of human tissues and cell lines reveals one dominant transcript per gene. Genome Biol14, R70, doi:10.1186/gb-2013-14-7-r70 (2013).
Grabherr, M.G. et al. Full-length transcriptome assembly from RNA-Seq data without a reference genome. Nat Biotechnol 29, 644-652, doi: 10.1038/nbt.1883 (2011).
Holland, P. V. Viral infections and the blood supply. The NEJM. 334:1734-1735 (1996).
Huang, X. & Madan, A. CAP3: A DNA sequence assembly program. Genome Res 9, 868-877 (1999).
Kupferschmidt, K. Epidemiology. Outbreak detectives embrace the genome era. Science 333, 1818-1819, doi:10.1126/science.333.6051.1818 (2011).
Lander, E. S. et al. Initial sequencing and analysis of the human genome. Nature 409, 860-921, doi:10.1038/35057062 (2001).

(Continued)

*Primary Examiner* — Young J Kim
(74) *Attorney, Agent, or Firm* — Ballard Spahr LLP

(57) ABSTRACT

Disclosed are compositions and methods for enriching a non-host sequence from a host sample. Also disclosed are compositions and methods for detecting a non-host sequence in a host sample. For example, a pathogen can be enriched and detected in a sample taken from a human without knowing what the pathogen is.

27 Claims, 12 Drawing Sheets

Specification includes a Sequence Listing.

(56) References Cited

OTHER PUBLICATIONS

Li, W. & Godzik, A. Cd-hit: a fast program for clustering and comparing large sets of protein or nucleotide sequences. Bioinformatics 22, 1658-1659 (2006).
Marcais, G. & Kingsford, C. A fast, lock-free approach for efficient parallel counting of occurrences of k-mers. Bioinformatics 27, 764-770, doi: 10.1093/bioinformatics/btr011 (2011).
Mardis, E. R. Anticipating the 1,000 dollar genome. Genome Biol 7, 112 (2006).
Mardis, E. R. The impact of next-generation sequencing technology on genetics. Trends Genet 24, 133-141 (2008).
Metzker, M. L. Emerging technologies in DNA sequencing. Genome Res 15, 1767-1776 (2005).
Metzker, M. L. Sequencing technologies—the next generation. Nat Rev Genet 11, 31-46, doi: 10.1038/nrg2626 (2010).
Morgulis, A. et al. Database indexing for production MegaBLAST searches. Bioinformatics 24, 1757-1764, doi: 10.1093/bioinformatics/btn322 (2008).
Palacios, G. et al. A New Arenavirus in a Cluster of Fatal Transplant-Associated Diseases. The New England journal of medicine (2008).
Rizk, G., Lavenier, D. & Chikhi, R. DSK: k-mer counting with very low memory usage. Bioinformatics 29, 652-653, doi: 10.1093/bioinformatics/btt020 (2013).
Sayers, E. W. et al. Database resources of the National Center for Biotechnology Information. Nucleic Acids Res 38, D5-16, doi: 10.1093/nar/gkp967 (2010).
Schmieder, R. & Edwards, R. Quality control and preprocessing of metagenomic datasets. Bioinformatics 27, 863-864, doi: 1 0.1093/bioinformatics/btr026 (2011 ).
Schreiber, G. B., Busch, M.P., Kleinman, S. H. & Korelitz, J. J. The risk of transfusion-transmitted viral infections. The Retrovirus Epidemiology Donor Study. The New England journal of medicine 334, 1685-1690 (1996).
Schuster, S.C. Next-generation sequencing transforms today's biology. Nat Methods 5, 16-18 (2008).
Shaffer, C. Next-generation sequencing outpaces expectations. Nat Biotechnol 25, 149 (2007).
Shendure, J. & Ji, H. Next-generation DNA sequencing. Nat Biotechnol 26, 1135-1145, 1486 (2008).
Shendure, J. & Lieberman Aiden, E. The expanding scope of DNA sequencing. Nat. Biotechnol 30, 1084-1094, doi:10.1038/nbt.2421 (2012).
Strausberg, R. L. et al. Generation and initial analysis of more than 15,000 full-length human and mouse eDNA sequences. Proceedings of the National Academy of Sciences of the United States of America 99, 16899-16903, doi:10.1073/pnas.242603899 (2002).
Strausberg, R. L., Feingold, E. A., Klausner, R. D. & Collins, F. S. The mammalian gene collection. Science 286, 455-457 ( 1999).
Team, M.G. C. P. et al. The completion of the Mammalian Gene Collection (MGC). Genome research 19, 2324-2333, doi:10.1101/gr.095976.109 (2009).
Von Bubnoff, A. Next-generation sequencing: the race is on. Cell132, 721-723 (2008).
Weber, G., et al. Identification of foreign gene sequences by transcript filtering against the human genome. Nat Genet 30, 141-142 (2002).
Wheeler, D. A. et al. The complete genome of an individual by massively parallel DNA sequencing. Nature 452, 872-876 (2008).
Xu, Y. et al. Pathogen discovery from human tissue by sequence-based computational subtraction. Genomics 81, 329-335 (2003).
International Search Report dated Apr. 7, 2015 for Application No. PCT/US2014/068644, which was filed on Dec. 4, 2014 and published as WO 2015/085105 on Jun. 11, 2015 (Applicant—University of Alaska Fairbanks) (3 Pages).
Written Opinion dated Apr. 7, 2015 for Application No. PCT/US2014/068644, which was filed on Dec. 4, 2014 and published as WO 2015/085105 on Jun. 11, 2015 (Applicant—University of Alaska Fairbanks) (8 Pages).
International Preliminary Report on Patentability dated Jun. 7, 2016 for Application No. PCT/US2014/068644, which was filed on Dec. 4, 2014 and published as WO 2015/085105 on Jun. 11, 2015 (Applicant—University of Alaska Fairbanks) (9 Pages).

\* cited by examiner

5'-ACGGCCTAATACGACTCACTATAGGGTTTTTTTTTTTTTTTTTTTVN-3'

T7 promoter poly d(T) primer

|  | Top 1000 transcripts | | | Top 2000 transcripts | | | Top 4000 transcripts | | | All 86,248 transcripts | | |
|---|---|---|---|---|---|---|---|---|---|---|---|---|
|  | Full transcript | 1000bp- 3' End | 500bp - 3'End | Full transcript | 1000bp - 3' End | 500bp - 3' End | Full transcript | 1000bp - 3' End | 500bp - 3' End | Full transcript | 1000bp - 3' End | 500bp - 3' End |
| 7-mer | 1 | 2 | 65 |  |  | 4 |  |  | 1 |  |  |  |
| 8-mer |  |  |  | 88 | 455 |  | 1 | 74 |  |  |  |  |
| 9-mer |  |  |  |  |  |  |  |  |  | 1 | 20 | 197 |

| Instrument | Instrument Cost | Service Contract | Run time | Millions of reads/run | Bases/read | Yield MB/run | Reagent Cost/run | Reagent Cost/MB |
|---|---|---|---|---|---|---|---|---|
| 454 FLX Titanium | 29.5K | - | 10 hrs. | 1 | 400 | 400 | $6,200 | $12 |
| 454 FLX* | 450K | 50K | 20 hrs. | 1 | 650 | 650 | $6,200 | $7 |
| 454 GS Jr. Titanium | 108K | 12.6K | 10 hrs. | 0.1 | 400 | 50 | $1,100 | $22 |
| Illumina GAIIx | 250K | 44.5K | 14 days | 300 | 150+150 | 96,000 | $17,575 | $0.19 |
| Illumina HiSeq 1000 | 560K | 62K | 8.5 days | ≤1500 | 100+100 | ≤300,000 | $10,220 | $0.04 |
| Illumina HiSeq 2000 | 690K | 75.9K | 11.5 days | ≤3000 | 100+100 | ≤600,000 | $23,470 | ≥$0.04 |
| Illumina HiSeq 2500 | 690K | 75.9K | 40 hrs. | ≤600 | 150+150 | ≤180,000 | $6,145 | ≤$0.05 |
| Illumina iScanSQ | 405K | 41.5K | 8.5 days | 700 | 100+100 | 140,000 | $12,750 | $0.09 |
| Illumina MiSeq v.1 | 125K | 12.5K | 26 hrs. | 4 | 150+150 | 1,200 | $1,040 | $0.70 |
| Illumina MiSeq v. 2 | 125K | 12.5K | 39 hrs. | 15 | 250+250 | 7,500 | $1,070 | $0.14 |
| Ion Torrent 314 chip | 49K | 7.5K | 4 hrs. | 0.1 | 400 | 40 | $539 | $5 |
| Ion Torrent 316 chip | | | 4 hrs. | 1.6 | 400 | 400 | $739 | $1.20 |
| Ion Torrent 318 chip | | | 7 hrs. | 4 | 400 | 1,500 | $939 | $.060 |
| Ion Torrent Proton I | 224K | 22.4K | ≤4 hrs. | 70 | ≤200 | 10,000 | $1,050 | $0.09 |
| Ion Torrent Proton II | | | [>4 hrs.] | [250] | [≤200] | [50,000] | [$1,000] | [$0.02] |
| Ion Torrent Proton III | | | [>4 hrs.] | [500] | [≤200] | [100,000] | [$1,000] | [$0.01] |
| Oxford Nano 2000 | | | [? hrs.] | [4] | [10,000] | [40,000] | varies | [$0.04] |
| Oxford Nano 8000 | | | [5 hrs.] | [10] | [10,000] | [100,000] | varies | $0.02 |
| Oxford Nano minion | | | ≤6 hrs. | [0.1] | [9,000] | 1,000 | ≤$900 | $1 |
| PacBio RS | 695K | 85K | ≤2 hrs. | 0.03 | >3,000 | 100-150 | ≥$300 | $2-17 |
| SOLID – 5500xl | 251K | 44.4K | 8 days | >1,410 | 75+35 | 155,100 | $10,503 | <$0.07 |

FIG. 4

| Adaptor | Sequence | Sequence | Adaptor |
|---|---|---|---|
| A | ACGCGTATGA (SEQ ID NO:1) | CGTAATACGT (SEQ ID NO:21) | 1 |
| B | ACGTAGCGTG (SEQ ID NO:2) | CGTAATCGGT (SEQ ID NO:22) | 2 |
| C | ATACGCGACT (SEQ ID NO:3) | CGTACAAACG (SEQ ID NO:23) | 3 |
| D | ATCGACGCAA (SEQ ID NO:4) | CGTACGAAAC (SEQ ID NO:24) | 4 |
| E | ATCGTTCGAC (SEQ ID NO:5) | CGTACGTTAG (SEQ ID NO:25) | 5 |
| F | ATTCGATCGC (SEQ ID NO:6) | GCGCGATAGG (SEQ ID NO:26) | 6 |
| G | CCGTCGAAGT (SEQ ID NO:7) | GCGCGTAAAT (SEQ ID NO:27) | 7 |
| H | CGAACGAATC (SEQ ID NO:8) | GTACGCGACT (SEQ ID NO:28) | 8 |
| I | CGACGTATTG (SEQ ID NO:9) | GTCGAACGAG (SEQ ID NO:29) | 9 |
| J | CGATACGTTC (SEQ ID NO:10) | TAACGTATCG (SEQ ID NO:30) | 10 |
| K | CGATCTAACA (SEQ ID NO:11) | TAACGTCGGC (SEQ ID NO:31) | 11 |
| L | CGATTCGGTT (SEQ ID NO:12) | TACGCGATTG (SEQ ID NO:32) | 12 |
| M | CGCCCGTTAA (SEQ ID NO:13) | TAGCGAACGC (SEQ ID NO:33) | 13 |
| N | CGCGATAGTG (SEQ ID NO:14) | TAGCGACGCA (SEQ ID NO:34) | 14 |
| O | CGCGTGTTAT (SEQ ID NO:15) | TATGCGACGC (SEQ ID NO:35) | 15 |
| P | CGGATCGTTA (SEQ ID NO:16) | TCGATCGGTG (SEQ ID NO:36) | 16 |
| Q | CGGTACGCAT (SEQ ID NO:17) | TCGCGAAATT (SEQ ID NO:37) | 17 |
| R | CGGTCGTAGA (SEQ ID NO:18) | TCGCGAATGA (SEQ ID NO:38) | 18 |
| S | CGTAACGACT (SEQ ID NO:19) | TCGTTCGTAC (SEQ ID NO:39) | 19 |
| T | CGTAACTAGG (SEQ ID NO:20) | TTATCGCGCA (SEQ ID NO:40) | 20 |

FIG. 5A

|   | 1  | 2  | 3  | 4  | 5  | 6  | 7  | 8  | 9  | 10  | 11  | 12  | 13  | 14  | 15  | 16  | 17  | 18  | 19  | 20  |
|---|----|----|----|----|----|----|----|----|----|-----|-----|-----|-----|-----|-----|-----|-----|-----|-----|-----|
| A | A1 | A2 | A3 | A4 | A5 | A6 | A7 | A8 | A9 | A10 | A11 | A12 | A13 | A14 | A15 | A16 | A17 | A18 | A19 | A20 |
| B | B1 | B2 | B3 | B4 | B5 | B6 | B7 | B8 | B9 | B10 | B11 | B12 | B13 | B14 | B15 | B16 | B17 | B18 | B19 | B20 |
| C | C1 | C2 | C3 | C4 | C5 | C6 | C7 | C8 | C9 | C10 | C11 | C12 | C13 | C14 | C15 | C16 | C17 | C18 | C19 | C20 |
| D | D1 | D2 | D3 | D4 | D5 | D6 | D7 | D8 | D9 | D10 | D11 | D12 | D13 | D14 | D15 | D16 | D17 | D18 | D19 | D20 |
| E | E1 | E2 | E3 | E4 | E5 | E6 | E7 | E8 | E9 | E10 | E11 | E12 | E13 | E14 | E15 | E16 | E17 | E18 | E19 | E20 |
| F | F1 | F2 | F3 | F4 | F5 | F6 | F7 | F8 | F9 | F10 | F11 | F12 | F13 | F14 | F15 | F16 | F17 | F18 | F19 | F20 |
| G | G1 | G2 | G3 | G4 | G5 | G6 | G7 | G8 | G9 | G10 | G11 | G12 | G13 | G14 | G15 | G16 | G17 | G18 | G19 | G20 |
| H | H1 | H2 | H3 | H4 | H5 | H6 | H7 | H8 | H9 | H10 | H11 | H12 | H13 | H14 | H15 | H16 | H17 | H18 | H19 | H20 |
| I | I1 | I2 | I3 | I4 | I5 | I6 | I7 | I8 | I9 | I10 | I11 | I12 | I13 | I14 | I15 | I16 | I17 | I18 | I19 | I20 |
| J | J1 | J2 | J3 | J4 | J5 | J6 | J7 | J8 | J9 | J10 | J11 | J12 | J13 | J14 | J15 | J16 | J17 | J18 | J19 | J20 |
| K | K1 | K2 | K3 | K4 | K5 | K6 | K7 | K8 | K9 | K10 | K11 | K12 | K13 | K14 | K15 | K16 | K17 | K18 | K19 | K20 |
| L | L1 | L2 | L3 | L4 | L5 | L6 | L7 | L8 | L9 | L10 | L11 | L12 | L13 | L14 | L15 | L16 | L17 | L18 | L19 | L20 |
| M | M1 | M2 | M3 | M4 | M5 | M6 | M7 | M8 | M9 | M10 | M11 | M12 | M13 | M14 | M15 | M16 | M17 | M18 | M19 | M20 |
| N | N1 | N2 | N3 | N4 | N5 | N6 | N7 | N8 | N9 | N10 | N11 | N12 | N13 | N14 | N15 | N16 | N17 | N18 | N19 | N20 |
| O | O1 | O2 | O3 | O4 | O5 | O6 | O7 | O8 | O9 | O10 | O11 | O12 | O13 | O14 | O15 | O16 | O17 | O18 | O19 | O20 |
| P | P1 | P2 | P3 | P4 | P5 | P6 | P7 | P8 | P9 | P10 | P11 | P12 | P13 | P14 | P15 | P16 | P17 | P18 | P19 | P20 |
| Q | Q1 | Q2 | Q3 | Q4 | Q5 | Q6 | Q7 | Q8 | Q9 | Q10 | Q11 | Q12 | Q13 | Q14 | Q15 | Q16 | Q17 | Q18 | Q19 | Q20 |
| R | R1 | R2 | R3 | R4 | R5 | R6 | R7 | R8 | R9 | R10 | R11 | R12 | R13 | R14 | R15 | R16 | R17 | R18 | R19 | R20 |
| S | S1 | S2 | S3 | S4 | S5 | S6 | S7 | S8 | S9 | S10 | S11 | S12 | S13 | S14 | S15 | S16 | S17 | S18 | S19 | S20 |
| T | T1 | T2 | T3 | T4 | T5 | T6 | T7 | T8 | T9 | T10 | T11 | T12 | T13 | T14 | T15 | T16 | T17 | T18 | T19 | T20 |

FIG. 5B

|        | Top 1000 | Top 2000 | Top 3000 | Top 4000 | Top 5000 | Top 6000 | Top 7000 | Top 8000 | Top 9000 | Top 10000 | Top 20000 | All 86248 |
|--------|----------|----------|----------|----------|----------|----------|----------|----------|----------|-----------|-----------|-----------|
| 8-mer  | 329      | 44       | 9        | 4        | 2        | 1        | 1        | 0        | 0        | 0         | 0         | 0         |
| 9-mer  | 23473    | 8883     | 4402     | 2411     | 1493     | 953      | 651      | 455      | 347      | 249       | 28        | 1         |
| 10-mer | 351888   | 203816   | 139254   | 100542   | 76937    | 60510    | 49753    | 41374    | 35737    | 30336     | 10053     | 1075      |

FIG. 6

| Percent of the sequences in the Virome covered by the oligos | | | | | | | | | | | | |
|---|---|---|---|---|---|---|---|---|---|---|---|---|
| | Top 1000 | Top 2000 | Top 3000 | Top 4000 | Top 5000 | Top 6000 | Top 7000 | Top 8000 | Top 9000 | Top 10000 | Top 20000 | All 75987 |
| 8-mers percent of virome covered | 86.9346734 | 41.2060302 | 16.5829146 | 11.5577889 | 9.04522613 | 8.04020101 | 8.04020101 | 0 | 0 | 0 | 0 | 0 |
| 8-mers total number | 329 | 44 | 9 | 4 | 4 | 2 | 1 | 0 | 0 | 0 | 0 | 0 |
| 8-mers number in short list | 62 | 26 | 8 | 4 | 2 | 1 | 1 | 0 | 0 | 0 | 0 | 0 |
| 9-mers percent of virome covered | 100 | 100 | 98.4924623 | 93.9698492 | 87.9396985 | 76.8844221 | 70.3517588 | 61.8090452 | 57.7889447 | 46.7336683 | 16.080402 | 2.01005025 |
| 9-mers total number | 23473 | 8883 | 4402 | 2411 | 1493 | 953 | 651 | 455 | 347 | 249 | 28 | 1 |
| 9-mers number in short list | 57 | 81 | 87 | 91 | 94 | 85 | 83 | 69 | 62 | 51 | 14 | 1 |
| 10-mers percent of virome covered | 100 | 100 | 100 | 100 | 100 | 100 | 100 | 100 | 100 | 100 | 95.4773869 | 48.241206 |
| 10-mers total number | 351888 | 203816 | 139254 | 100542 | 76937 | 60510 | 49753 | 41374 | 35737 | 30336 | 10053 | 1075 |
| 10-mers number in short list | 164 | 167 | 174 | 179 | 177 | 180 | 180 | 181 | 179 | 179 | 171 | 81 |

FIG. 7

| | Top 1000 | Top 2000 | Top 3000 | Top 4000 | Top 5000 | Top 6000 |
|---|---|---|---|---|---|---|
| 8-mers percent of virome covered | 86.9346734 | 41.2060302 | 16.5829146 | 11.5577889 | 9.04522613 | 8.04020101 |
| 8-mers total number | 329 | 44 | 9 | 4 | 2 | 1 |
| 8-mers number in short list | 62 | 26 | 8 | 4 | 2 | 1 |
| 9-mers percent of virome covered | 100 | 100 | 98.4924623 | 93.9698492 | 87.9396985 | 76.8844221 |
| 9-mers total number | 23473 | 8883 | 4402 | 2411 | 1493 | 953 |
| 9-mers number in short list | 57 | 81 | 87 | 91 | 94 | 85 |
| 10-mers percent of virome covered | 100 | 100 | 100 | 100 | 100 | 100 |
| 10-mers total number | 351888 | 203816 | 139254 | 100542 | 76937 | 60510 |
| 10-mers number in short list | 164 | 167 | 174 | 179 | 177 | 180 |

| | Top 7000 | Top 8000 | Top 9000 | Top 10000 | Top 20000 | All 75987 |
|---|---|---|---|---|---|---|
| 8-mers percent of virome covered | 8.04020101 | 0 | 0 | 0 | 0 | 0 |
| 8-mers total number | 1 | 0 | 0 | 0 | 0 | 0 |
| 8-mers number in short list | 1 | 0 | 0 | 0 | 0 | 0 |
| 9-mers percent of virome covered | 70.3517588 | 61.8090452 | 57.7889447 | 46.7336683 | 16.080402 | 2.01005025 |
| 9-mers total number | 651 | 455 | 347 | 249 | 28 | 1 |
| 9-mers number in short list | 83 | 69 | 62 | 51 | 14 | 1 |
| 10-mers percent of virome covered | 100 | 100 | 100 | 100 | 95.4773869 | 48.241206 |
| 10-mers total number | 49753 | 41374 | 35737 | 30336 | 10053 | 1075 |
| 10-mers number in short list | 180 | 181 | 179 | 179 | 171 | 81 |

FIG. 9

| | | | | |
|---|---|---|---|---|
| ACGCCGGGTT | CAGACCGGAT | CGAGTAAGTA | ATGTAACCGT | CACGAACAAC |
| TCGCACATCG | TAAGGCAACG | GTACGACAAA | CGCATCATTA | TCGAGATACG |
| GATGCGTTAA | GGTACGCTAT | TCAGGCGTAA | CAATCGTTGA | TTGACCCGTA |
| GCGTGGTTAA | TATCGGTCAA | TCGTAACGCT | TCCGAATAGG | TCGTAATCAA |
| CGGACGAAAA | CGTACCTAGA | GCGTGGATAA | CGGGTCGCAA | CTCGACCAAA |
| TTATTCGCGC | ATTCGACGCT | TGGAACGCCG | GATATTCGCA | AATACTCGAG |
| TTATTCGCGT | AGCTCGATAG | CAACGATCAA | ATTCGCGCAT | ATGTTTTGCG |
| CGACTACTAA | GTTGGCGAAA | AAGGTCGACG | TATCGAGGTT | TGTCGCGTCA |
| AGCTTGCGTC | CGAACAACTA | TACTTACGGA | ACGTTATAGC | TCCCATACCG |
| GACCCGTAAA | GCACGGTATC | CATAACGCAC | ATAGGGCGT | TAGCGAGTAG |
| TAGCGACCGA | TGCGTAACTA | GTCGGTGAAA | AGGTTGCGAC | CTAAACCCGC |
| CCGTTGAACG | GGTACGCGAC | GCGATTGCGA | CGACGTTGCA | GATGAATTCG |
| ACTACGATTA | ACGCGTCATA | CCGTAACTTA | GTCTTCGGTA | CGATTGTACT |
| TGCGATTTCG | GATCACGTAA | ACGCAAGACA | AGCGCAATCA | |
| TGTAATCCGC | GATCACGTAT | TCGTCCCGAT | TGTTATGCGA | |
| GCGCAGCGAT | CCGTAGTACC | GGCATAATCG | GTCATACGTA | |
| CGGTCTATAT | TCAAGTTACG | ACGTATTCTA | CGTAATTATG | |
| TCGGTCGTAA | CGCATATACA | CGCGTACGAG | TCGCAAAATA | |
| GACGCATAGG | AACGTTACGT | CGACTTATCG | TAGCACCGCC | |
| GCGCATACGT | GTAACCGCGA | AGTCGAGTAC | GTCTAAACGA | |
| CCGAAGTCGA | GCACGATCGA | TTCGTAACGA | TAGCACGCCA | |
| ATACGTCGGA | ATCAGTTCGG | CTATAATCGG | GGCGTTTAGC | |
| TACCGGTTGC | CGATATCGGA | CTATCGATAG | CTACGATTAT | |
| TCCGATTAAC | GTTTTCCGGG | AACCAATCCG | GGTACGGTTA | |
| TCCGATTAAA | GTTACGCGAC | TCGTGAGTTA | ATAGAGTCGG | |
| CAATACGTAC | ATACCGGTCG | GCTCTCAACG | CGTTATGGGT | |
| GAACAATGCG | TCGCATGGGT | TTATCGGTCA | CGGACATAAA | |
| TACACGCGAT | TGACGTACGG | TCATGTCGTT | TCGAACCGGC | |
| AATCGATCGA | ATTGCGCTTT | CGTATACAAG | ACAAGTCGCA | |
| GCGCGTCTAA | TGACGCAATG | CGCAATAGAA | CGATCCCTAT | |
| CGTTAAGAGG | TATCGCACTA | TATCTCGATC | TAGACGACCA | |
| ATCGCCTATA | AGTGCGGTAA | CATTTGCGCA | TAGTCGGAAT | |
| CGTACGCGTC | CTAATAAGCG | CGGTACGACG | ATTCGCAGTT | |
| TATTTACGGC | ATAATCCGAT | TACCCCCGT | CTTCGTTAGC | |

FIG. 10

| | | | | |
|---|---|---|---|---|
| CGCGAAATGG | CTATCGATAG | ATCGTATCGA | CTCGACCAAA | TGCTAATCGC |
| CTATACGCAA | ATATATCGAA | TCTACGCATC | GTTGACGTAT | CGAACCGAAC |
| TACACGATAT | TTATCGCGAG | CGTCATCGGT | CATCGCTAGA | ATCGTATGGT |
| AGCGCACGTA | TATTGGATCG | CACGATTCGT | TGTCGCGTCA | TGTCGATCAC |
| CCGTCAAACG | GTAAGCGTAG | CGTCTCTCGT | CGCGCTTATT | CGTACCGATG |
| ATTCTCGTCG | CCGCTGATAC | TATCGATTAG | CGAGCATGTA | ATACATGCGG |
| GGCGCGATAC | GTTCGCACTA | GTTAATACGA | TAGCGAGTAG | |
| CATATTGCGT | GCGTCGAACT | TCGAACCGGC | GACCATAGCG | |
| CCGCGGTAAG | TTCGACTAGT | GTCTAACGAC | TAATCAACCG | |
| CACGATTGAT | GATGCGTTAA | ACAAGTCGCA | GCAATCGTTG | |
| GTCTAGACGC | CGGACGAAAA | TATCGTACAC | ATTAGTCGAG | |
| CGTTACGCTT | TCGGTCGTAA | GTGCGGTATC | CGCCGTTTGA | |
| TACGTCGAGT | TACCGGTTGC | ACTACGCATT | CGTTTCCGAA | |
| GGCATAATCG | AATAGGGCGA | TGACGGTTCG | CGACTGATCA | |
| GGCGCATATA | AATCGATCGA | TACCTAACCG | ACGACTAATG | |
| TAACTCGTGG | GCGCGTCTAA | ATAATGGTCG | GTTGTCCGAT | |
| CGCGGTATAC | GGTACGCTAT | ACTCATTCCG | ACTTATCGGA | |
| ATGCGCGACG | TATCGGTCAA | ATCGTTAACG | GAACTATCGT | |
| CGTTATCCGC | CGTACCTAGA | ATGTCGCATC | TATAGTTTCG | |
| AACGTTACGT | GGTACGCGAC | CGTACTATTA | ATACGGACAA | |
| GCGTAACTAG | CGGTACGACG | TAGTGTCGCC | TAACGCTAGG | |
| GCGTAACTAA | CCGCATATAG | CTACGGTTAG | CGGTCCGTAT | |
| TGCGCCGAAC | ATAATATCGC | TAGGCTAGCG | TTAAACGGTA | |
| ATCAGTTCGG | CTTAACGATC | CGATTCGGTT | TATCGCGTGT | |
| CGATATCGGA | TCGCCATACG | GATGCGACTA | ACTAGGGTCG | |
| ATACCGGTCG | TATCGTATTG | TAAGTTACCG | TCTAGCGAAT | |
| TCGAGGTTAC | GTACTCGTAG | GGTATGCGTA | TAACATCGCC | |
| CTCGTACCTA | TACGAATGCG | AACCGAACGT | TTCAATCCGG | |
| TATCGCACTA | ACGCTTGCGT | TCACGATACA | TTCGATAACT | |
| AAGTCTAACG | CGGTTAGATC | CAATTGCCGA | ACCGTCTCGA | |
| GTATCACGCG | ACGATAGGAC | ATTAATATCG | TATCCGTTCG | |
| TAAGACGGGG | CGACCCATAA | CAATCCGTAC | CGGTGTATAT | |
| TACTATCGAC | ATTCGCGCAT | GGTCGAATAA | GGGCATAGCG | |
| CGAGTAAGTA | ATAGGGGCGT | CGCAATAAGG | TAAGCTACGG | |
| CGGTAAGCGC | TAACATGCGA | TACTTTCGGT | TAGAACGCGA | |

FIG. 11

SEQUENCE LISTING

<160> NUMBER OF SEQ ID NOS: 336

<210> SEQ ID NO 1
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 1
acgcgtatga                                                          10

<210> SEQ ID NO 2
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 2

-continued acgtagcgtg                                                              10

<210> SEQ ID NO 3
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 3
atacgcgact                                                              10

<210> SEQ ID NO 4
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 4
atcgacgcaa                                                              10

<210> SEQ ID NO 5
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 5
atcgttcgac                                                              10

<210> SEQ ID NO 6
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 6
attcgatcgc                                                              10

<210> SEQ ID NO 7
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 7
ccgtcgaagt                                                              10

<210> SEQ ID NO 8
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 8
cgaacgaatc                                                              10

<210> SEQ ID NO 9
<211> LENGTH: 10
<212> TYPE: DNA
<213> ORGANISM: Artificial Sequence

```
<220> FEATURE:
<223> OTHER INFORMATION: synthetic construct; oligonucleotide

<400> SEQUENCE: 9
cgacgtattg                                                              10

<210> SEQ ID NO 10
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 10
cgatacgttc                                                              10

<210> SEQ ID NO 11
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 11
cgatctaaca                                                              10

<210> SEQ ID NO 12
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 12
cgattcggtt                                                              10

<210> SEQ ID NO 13
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 13
cgcccgttaa                                                              10

<210> SEQ ID NO 14
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 14
cgcgatagtg                                                              10

<210> SEQ ID NO 15
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 15
cgcgtgttat                                                              10
```

```
<210> SEQ ID NO 16
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 16
cggatcgtta                                                              10

<210> SEQ ID NO 17
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 17
cggtacgcat                                                              10

<210> SEQ ID NO 18
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 18
cggtcgtaga                                                              10

<210> SEQ ID NO 19
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 19
cgtaacgact                                                              10

<210> SEQ ID NO 20
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 20
cgtaactagg                                                              10

<210> SEQ ID NO 21
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 21
cgtaatacgt                                                              10

<210> SEQ ID NO 22
<211> LENGTH: 10
<212> TYPE: DNA
<213> ORGANISM: Artificial Sequence
<220> FEATURE:
<223> OTHER INFORMATION: synthetic construct; oligonucleotide
```

```
<400> SEQUENCE: 22
cgtaatcggt                                                              10

<210> SEQ ID NO 23
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 23
cgtacaaacg                                                              10

<210> SEQ ID NO 24
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 24
cgtacgaaac                                                              10

<210> SEQ ID NO 25
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 25
cgtacgttag                                                              10

<210> SEQ ID NO 26
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 26
gcgcgatagg                                                              10

<210> SEQ ID NO 27
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 27
gcgcgtaaat                                                              10

<210> SEQ ID NO 28
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 28
gtacgcgact                                                              10

<210> SEQ ID NO 29
```

```
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 29
gtcgaacgag                                                          10

<210> SEQ ID NO 30
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 30
taacgtatcg                                                          10

<210> SEQ ID NO 31
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 31
taacgtcggc                                                          10

<210> SEQ ID NO 32
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 32
tacgcgattg                                                          10

<210> SEQ ID NO 33
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 33
tagcgaacgc                                                          10

<210> SEQ ID NO 34
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 34
tagcgacgca                                                          10

<210> SEQ ID NO 35
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 35
```
tatgcgacgc                                                                 10

<210> SEQ ID NO 36
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 36
tcgatcggtg                                                                 10

<210> SEQ ID NO 37
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 37
tcgcgaaatt                                                                 10

<210> SEQ ID NO 38
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 38
tcgcgaatga                                                                 10

<210> SEQ ID NO 39
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 39
tcgttcgtac                                                                 10

<210> SEQ ID NO 40
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 40
ttatcgcgca                                                                 10

<210> SEQ ID NO 41
<211> LENGTH: 46
<212> TYPE: DNA
<213> ORGANISM: Artificial Sequence
<220> FEATURE:
<223> OTHER INFORMATION: synthetic construct; poly d(T) oligo
<220> FEATURE:
<221> NAME/KEY: misc_feature
<222> LOCATION: (46)..(46)
<223> OTHER INFORMATION: n is a, c, g, or t

<400> SEQUENCE: 41
acggcctaat acgactcact atagggtttt tttttttttt ttttvn                         46

```
<210> SEQ ID NO 42
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 42
acgccgggtt                                                              10

<210> SEQ ID NO 43
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 43
tcgcacatcg                                                              10

<210> SEQ ID NO 44
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 44
gatgcgttaa                                                              10

<210> SEQ ID NO 45
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 45
gcgtggttaa                                                              10

<210> SEQ ID NO 46
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 46
cggacgaaaa                                                              10

<210> SEQ ID NO 47
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 47
ttattcgcgc                                                              10

<210> SEQ ID NO 48
<211> LENGTH: 10
<212> TYPE: DNA
<213> ORGANISM: Artificial Sequence
<220> FEATURE:
<223> OTHER INFORMATION: synthetic construct; oligonucleotide
```

<400> SEQUENCE: 48
ttattcgcgt                                                          10

<210> SEQ ID NO 49
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 49
cgactactaa                                                          10

<210> SEQ ID NO 50
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 50
agcttgcgtc                                                          10

<210> SEQ ID NO 51
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 51
gacccgtaaa                                                          10

<210> SEQ ID NO 52
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 52
tagcgaccga                                                          10

<210> SEQ ID NO 53
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 53
ccgttgaacg                                                          10

<210> SEQ ID NO 54
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 54
actacgatta                                                          10

<210> SEQ ID NO 55

```
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 55
tgcgatttcg                                                              10

<210> SEQ ID NO 56
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 56
tgtaatccgc                                                              10

<210> SEQ ID NO 57
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 57
gcgcagcgat                                                              10

<210> SEQ ID NO 58
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 58
cggtctatat                                                              10

<210> SEQ ID NO 59
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 59
tcggtcgtaa                                                              10

<210> SEQ ID NO 60
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 60
gacgcatagg                                                              10

<210> SEQ ID NO 61
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 61
```

```
gcgcatacgt                                                          10

<210> SEQ ID NO 62
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 62
ccgaagtcga                                                          10

<210> SEQ ID NO 63
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 63
atacgtcgga                                                          10

<210> SEQ ID NO 64
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 64
taccggttgc                                                          10

<210> SEQ ID NO 65
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 65
tccgattaac                                                          10

<210> SEQ ID NO 66
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 66
tccgattaaa                                                          10

<210> SEQ ID NO 67
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 67
caatacgtac                                                          10

<210> SEQ ID NO 68
<211> LENGTH: 10
<212> TYPE: DNA
```

```
<213> ORGANISM: Artificial Sequence
<220> FEATURE:
<223> OTHER INFORMATION: synthetic construct; oligonucleotide

<400> SEQUENCE: 68
gaacaatgcg                                                           10

<210> SEQ ID NO 69
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 69
tacacgcgat                                                           10

<210> SEQ ID NO 70
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 70
aatcgatcga                                                           10

<210> SEQ ID NO 71
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 71
gcgcgtctaa                                                           10

<210> SEQ ID NO 72
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 72
cgttaagagg                                                           10

<210> SEQ ID NO 73
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 73
atcgcctata                                                           10

<210> SEQ ID NO 74
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 74
cgtacgcgtc                                                           10
```

<210> SEQ ID NO 75
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 75
tatttacggc                                                                 10

<210> SEQ ID NO 76
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 76
cagaccggat                                                                 10

<210> SEQ ID NO 77
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 77
taaggcaacg                                                                 10

<210> SEQ ID NO 78
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 78
ggtacgctat                                                                 10

<210> SEQ ID NO 79
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 79
tatcggtcaa                                                                 10

<210> SEQ ID NO 80
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 80
cgtacctaga                                                                 10

<210> SEQ ID NO 81
<211> LENGTH: 10
<212> TYPE: DNA
<213> ORGANISM: Artificial Sequence
<220> FEATURE:

<223> OTHER INFORMATION: synthetic construct; oligonucleotide

<400> SEQUENCE: 81
attcgacgct    10

<210> SEQ ID NO 82
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 82
agctcgatag    10

<210> SEQ ID NO 83
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 83
gttggcgaaa    10

<210> SEQ ID NO 84
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 84
cgaacaacta    10

<210> SEQ ID NO 85
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 85
gcacggtatc    10

<210> SEQ ID NO 86
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 86
tgcgtaacta    10

<210> SEQ ID NO 87
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 87
ggtacgcgac    10

```
<210> SEQ ID NO 88
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 88
acgcgtcata                                                              10

<210> SEQ ID NO 89
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 89
gatcacgtaa                                                              10

<210> SEQ ID NO 90
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 90
gatcacgtat                                                              10

<210> SEQ ID NO 91
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 91
ccgtagtacc                                                              10

<210> SEQ ID NO 92
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 92
tcaagttacg                                                              10

<210> SEQ ID NO 93
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 93
cgcatataca                                                              10

<210> SEQ ID NO 94
<211> LENGTH: 10
<212> TYPE: DNA
<213> ORGANISM: Artificial Sequence
<220> FEATURE:
<223> OTHER INFORMATION: synthetic construct; oligonucleotide
```

```
<400> SEQUENCE: 94
aacgttacgt                                                              10

<210> SEQ ID NO 95
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 95
gtaaccgcga                                                              10

<210> SEQ ID NO 96
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 96
gcacgatcga                                                              10

<210> SEQ ID NO 97
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 97
atcagttcgg                                                              10

<210> SEQ ID NO 98
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 98
cgatatcgga                                                              10

<210> SEQ ID NO 99
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 99
gttttccggg                                                              10

<210> SEQ ID NO 100
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 100
gttacgcgac                                                              10

<210> SEQ ID NO 101
<211> LENGTH: 10
```

```
<212> TYPE: DNA
<213> ORGANISM: Artificial Sequence
<220> FEATURE:
<223> OTHER INFORMATION: synthetic construct; oligonucleotide

<400> SEQUENCE: 101
ataccggtcg                                                              10

<210> SEQ ID NO 102
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 102
tcgcatgggt                                                              10

<210> SEQ ID NO 103
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 103
tgacgtacgg                                                              10

<210> SEQ ID NO 104
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 104
attgcgcttt                                                              10

<210> SEQ ID NO 105
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 105
tgacgcaatg                                                              10

<210> SEQ ID NO 106
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 106
tatcgcacta                                                              10

<210> SEQ ID NO 107
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 107
```
agtgcggtaa 10

<210> SEQ ID NO 108
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 108
ctaataagcg 10

<210> SEQ ID NO 109
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 109
ataatccgat 10

<210> SEQ ID NO 110
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 110
cgagtaagta 10

<210> SEQ ID NO 111
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 111
gtacgacaaa 10

<210> SEQ ID NO 112
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 112
tcaggcgtaa 10

<210> SEQ ID NO 113
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 113
tcgtaacgct 10

<210> SEQ ID NO 114
<211> LENGTH: 10
<212> TYPE: DNA
<213> ORGANISM: Artificial Sequence

```
<220> FEATURE:
<223> OTHER INFORMATION: synthetic construct; oligonucleotide

<400> SEQUENCE: 114
gcgtggataa                                                              10

<210> SEQ ID NO 115
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 115
tggaacgccg                                                              10

<210> SEQ ID NO 116
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 116
caacgatcaa                                                              10

<210> SEQ ID NO 117
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 117
aaggtcgacg                                                              10

<210> SEQ ID NO 118
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 118
tacttacgga                                                              10

<210> SEQ ID NO 119
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 119
cataacgcac                                                              10

<210> SEQ ID NO 120
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 120
gtcggtgaaa                                                              10
```

```
<210> SEQ ID NO 121
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 121
gcgattgcga                                                          10

<210> SEQ ID NO 122
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 122
ccgtaactta                                                          10

<210> SEQ ID NO 123
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 123
acgcaagaca                                                          10

<210> SEQ ID NO 124
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 124
tcgtcccgat                                                          10

<210> SEQ ID NO 125
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 125
ggcataatcg                                                          10

<210> SEQ ID NO 126
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 126
acgtattcta                                                          10

<210> SEQ ID NO 127
<211> LENGTH: 10
<212> TYPE: DNA
<213> ORGANISM: Artificial Sequence
<220> FEATURE:
<223> OTHER INFORMATION: synthetic construct; oligonucleotide
```

```
<400> SEQUENCE: 127
cgcgtacgag                                                              10

<210> SEQ ID NO 128
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 128
cgacttatcg                                                              10

<210> SEQ ID NO 129
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 129
agtcgagtac                                                              10

<210> SEQ ID NO 130
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 130
ttcgtaacga                                                              10

<210> SEQ ID NO 131
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 131
ctataatcgg                                                              10

<210> SEQ ID NO 132
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 132
ctatcgatag                                                              10

<210> SEQ ID NO 133
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 133
aaccaatccg                                                              10

<210> SEQ ID NO 134
```

```
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 134
tcgtgagtta                                                          10

<210> SEQ ID NO 135
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 135
gctctcaacg                                                          10

<210> SEQ ID NO 136
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 136
ttatcggtca                                                          10

<210> SEQ ID NO 137
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 137
tcatgtcgtt                                                          10

<210> SEQ ID NO 138
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 138
cgtatacaag                                                          10

<210> SEQ ID NO 139
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 139
cgcaatagaa                                                          10

<210> SEQ ID NO 140
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 140
```
tatctcgatc 10

<210> SEQ ID NO 141
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 141
catttgcgca 10

<210> SEQ ID NO 142
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 142
cggtacgacg 10

<210> SEQ ID NO 143
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 143
tacccccgt 10

<210> SEQ ID NO 144
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 144
atgtaaccgt 10

<210> SEQ ID NO 145
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 145
cgcatcatta 10

<210> SEQ ID NO 146
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 146
caatcgttga 10

<210> SEQ ID NO 147
<211> LENGTH: 10
<212> TYPE: DNA

<213> ORGANISM: Artificial Sequence
<220> FEATURE:
<223> OTHER INFORMATION: synthetic construct; oligonucleotide

<400> SEQUENCE: 147
tccgaatagg       10

<210> SEQ ID NO 148
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 148
cgggtcgcaa       10

<210> SEQ ID NO 149
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 149
gatattcgca       10

<210> SEQ ID NO 150
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 150
attcgcgcat       10

<210> SEQ ID NO 151
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 151
tatcgaggtt       10

<210> SEQ ID NO 152
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 152
acgttatagc       10

<210> SEQ ID NO 153
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 153
ataggggcgt       10

```
<210> SEQ ID NO 154
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 154
aggttgcgac                                                          10

<210> SEQ ID NO 155
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 155
cgacgttgca                                                          10

<210> SEQ ID NO 156
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 156
gtcttcggta                                                          10

<210> SEQ ID NO 157
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 157
agcgcaatca                                                          10

<210> SEQ ID NO 158
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 158
tgttatgcga                                                          10

<210> SEQ ID NO 159
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 159
gtcatacgta                                                          10

<210> SEQ ID NO 160
<211> LENGTH: 10
<212> TYPE: DNA
<213> ORGANISM: Artificial Sequence
<220> FEATURE:
```

```
<223> OTHER INFORMATION: synthetic construct; oligonucleotide

<400> SEQUENCE: 160
cgtaattatg                                                              10

<210> SEQ ID NO 161
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 161
tcgcaaaata                                                              10

<210> SEQ ID NO 162
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 162
tagcaccgcc                                                              10

<210> SEQ ID NO 163
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 163
gtctaaacga                                                              10

<210> SEQ ID NO 164
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 164
tagcacgcca                                                              10

<210> SEQ ID NO 165
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 165
ggcgtttagc                                                              10

<210> SEQ ID NO 166
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 166
ctacgattat                                                              10
```

```
<210> SEQ ID NO 167
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 167
ggtacggtta                                                              10

<210> SEQ ID NO 168
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 168
atagagtcgg                                                              10

<210> SEQ ID NO 169
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 169
cgttatgggt                                                              10

<210> SEQ ID NO 170
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 170
cggacataaa                                                              10

<210> SEQ ID NO 171
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 171
tcgaaccggc                                                              10

<210> SEQ ID NO 172
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 172
acaagtcgca                                                              10

<210> SEQ ID NO 173
<211> LENGTH: 10
<212> TYPE: DNA
<213> ORGANISM: Artificial Sequence
<220> FEATURE:
<223> OTHER INFORMATION: synthetic construct; oligonucleotide
```

<400> SEQUENCE: 173
cgatccctat                                                                      10

<210> SEQ ID NO 174
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 174
tagacgacca                                                                      10

<210> SEQ ID NO 175
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 175
tagtcggaat                                                                      10

<210> SEQ ID NO 176
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 176
attcgcagtt                                                                      10

<210> SEQ ID NO 177
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 177
cttcgttagc                                                                      10

<210> SEQ ID NO 178
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 178
cacgaacaac                                                                      10

<210> SEQ ID NO 179
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 179
tcgagatacg                                                                      10

<210> SEQ ID NO 180
<211> LENGTH: 10

```
<212> TYPE: DNA
<213> ORGANISM: Artificial Sequence
<220> FEATURE:
<223> OTHER INFORMATION: synthetic construct; oligonucleotide

<400> SEQUENCE: 180
ttgacccgta                                                              10

<210> SEQ ID NO 181
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 181
tcgtaatcaa                                                              10

<210> SEQ ID NO 182
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 182
ctcgaccaaa                                                              10

<210> SEQ ID NO 183
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 183
aatactcgag                                                              10

<210> SEQ ID NO 184
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 184
atgttttgcg                                                              10

<210> SEQ ID NO 185
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 185
tgtcgcgtca                                                              10

<210> SEQ ID NO 186
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 186
```
tcccataccg                                                              10

<210> SEQ ID NO 187
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 187
tagcgagtag                                                              10

<210> SEQ ID NO 188
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 188
ctaaacccgc                                                              10

<210> SEQ ID NO 189
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 189
gatgaattcg                                                              10

<210> SEQ ID NO 190
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 190
cgattgtact                                                              10

<210> SEQ ID NO 191
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 191
cgcgaaatgg                                                              10

<210> SEQ ID NO 192
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 192
ctatacgcaa                                                              10

<210> SEQ ID NO 193
<211> LENGTH: 10
<212> TYPE: DNA
<213> ORGANISM: Artificial Sequence

```
<220> FEATURE:
<223> OTHER INFORMATION: synthetic construct; oligonucleotide

<400> SEQUENCE: 193
tacacgatat                                                          10

<210> SEQ ID NO 194
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 194
agcgcacgta                                                          10

<210> SEQ ID NO 195
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 195
ccgtcaaacg                                                          10

<210> SEQ ID NO 196
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 196
attctcgtcg                                                          10

<210> SEQ ID NO 197
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 197
ggcgcgatac                                                          10

<210> SEQ ID NO 198
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 198
catattgcgt                                                          10

<210> SEQ ID NO 199
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 199
ccgcggtaag                                                          10
```

```
<210> SEQ ID NO 200
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 200
cacgattgat                                                            10

<210> SEQ ID NO 201
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 201
gtctagacgc                                                            10

<210> SEQ ID NO 202
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 202
cgttacgctt                                                            10

<210> SEQ ID NO 203
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 203
tacgtcgagt                                                            10

<210> SEQ ID NO 204
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 204
ggcataatcg                                                            10

<210> SEQ ID NO 205
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 205
ggcgcatata                                                            10

<210> SEQ ID NO 206
<211> LENGTH: 10
<212> TYPE: DNA
<213> ORGANISM: Artificial Sequence
<220> FEATURE:
<223> OTHER INFORMATION: synthetic construct; oligonucleotide
```

<400> SEQUENCE: 206
taactcgtgg                                                              10

<210> SEQ ID NO 207
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 207
cgcggtatac                                                              10

<210> SEQ ID NO 208
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 208
atgcgcgacg                                                              10

<210> SEQ ID NO 209
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 209
cgttatccgc                                                              10

<210> SEQ ID NO 210
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 210
aacgttacgt                                                              10

<210> SEQ ID NO 211
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 211
gcgtaactag                                                              10

<210> SEQ ID NO 212
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 212
gcgtaactaa                                                              10

<210> SEQ ID NO 213

```
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 213
tgcgccgaac                                                                10

<210> SEQ ID NO 214
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 214
atcagttcgg                                                                10

<210> SEQ ID NO 215
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 215
cgatatcgga                                                                10

<210> SEQ ID NO 216
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 216
ataccggtcg                                                                10

<210> SEQ ID NO 217
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 217
tcgaggttac                                                                10

<210> SEQ ID NO 218
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 218
ctcgtaccta                                                                10

<210> SEQ ID NO 219
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 219
```
tatcgcacta                                                           10

<210> SEQ ID NO 220
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 220
aagtctaacg                                                           10

<210> SEQ ID NO 221
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 221
gtatcacgcg                                                           10

<210> SEQ ID NO 222
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 222
taagacgggg                                                           10

<210> SEQ ID NO 223
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 223
tactatcgac                                                           10

<210> SEQ ID NO 224
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 224
cgagtaagta                                                           10

<210> SEQ ID NO 225
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 225
cggtaagcgc                                                           10

<210> SEQ ID NO 226
<211> LENGTH: 10
<212> TYPE: DNA

```
<213> ORGANISM: Artificial Sequence
<220> FEATURE:
<223> OTHER INFORMATION: synthetic construct; oligonucleotide

<400> SEQUENCE: 226
ctatcgatag                                                           10

<210> SEQ ID NO 227
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 227
atatatcgaa                                                           10

<210> SEQ ID NO 228
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 228
ttatcgcgag                                                           10

<210> SEQ ID NO 229
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 229
tattggatcg                                                           10

<210> SEQ ID NO 230
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 230
gtaagcgtag                                                           10

<210> SEQ ID NO 231
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 231
ccgctgatac                                                           10

<210> SEQ ID NO 232
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 232
gttcgcacta                                                           10
```

<210> SEQ ID NO 233
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 233
gcgtcgaact                                                                 10

<210> SEQ ID NO 234
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 234
ttcgactagt                                                                 10

<210> SEQ ID NO 235
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 235
gatgcgttaa                                                                 10

<210> SEQ ID NO 236
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 236
cggacgaaaa                                                                 10

<210> SEQ ID NO 237
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 237
tcggtcgtaa                                                                 10

<210> SEQ ID NO 238
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 238
taccggttgc                                                                 10

<210> SEQ ID NO 239
<211> LENGTH: 10
<212> TYPE: DNA
<213> ORGANISM: Artificial Sequence
<220> FEATURE:

<223> OTHER INFORMATION: synthetic construct; oligonucleotide

<400> SEQUENCE: 239
aatagggcga                                                                10

<210> SEQ ID NO 240
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 240
aatcgatcga                                                                10

<210> SEQ ID NO 241
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 241
gcgcgtctaa                                                                10

<210> SEQ ID NO 242
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 242
ggtacgctat                                                                10

<210> SEQ ID NO 243
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 243
tatcggtcaa                                                                10

<210> SEQ ID NO 244
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 244
cgtacctaga                                                                10

<210> SEQ ID NO 245
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 245
ggtacgcgac                                                                10

```
<210> SEQ ID NO 246
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 246
cggtacgacg                                                              10

<210> SEQ ID NO 247
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 247
ccgcatatag                                                              10

<210> SEQ ID NO 248
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 248
ataatatcgc                                                              10

<210> SEQ ID NO 249
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 249
cttaacgatc                                                              10

<210> SEQ ID NO 250
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 250
tcgccatacg                                                              10

<210> SEQ ID NO 251
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 251
tatcgtattg                                                              10

<210> SEQ ID NO 252
<211> LENGTH: 10
<212> TYPE: DNA
<213> ORGANISM: Artificial Sequence
<220> FEATURE:
<223> OTHER INFORMATION: synthetic construct; oligonucleotide
```

<400> SEQUENCE: 252
gtactcgtag                                                          10

<210> SEQ ID NO 253
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 253
tacgaatgcg                                                          10

<210> SEQ ID NO 254
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 254
acgcttgcgt                                                          10

<210> SEQ ID NO 255
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 255
cggttagatc                                                          10

<210> SEQ ID NO 256
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 256
acgataggac                                                          10

<210> SEQ ID NO 257
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 257
cgacccataa                                                          10

<210> SEQ ID NO 258
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 258
attcgcgcat                                                          10

<210> SEQ ID NO 259
<211> LENGTH: 10

```
<212> TYPE: DNA
<213> ORGANISM: Artificial Sequence
<220> FEATURE:
<223> OTHER INFORMATION: synthetic construct; oligonucleotide

<400> SEQUENCE: 259
ataggggcgt                                                              10

<210> SEQ ID NO 260
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 260
taacatgcga                                                              10

<210> SEQ ID NO 261
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 261
atcgtatcga                                                              10

<210> SEQ ID NO 262
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 262
tctacgcatc                                                              10

<210> SEQ ID NO 263
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 263
cgtcatcggt                                                              10

<210> SEQ ID NO 264
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 264
cacgattcgt                                                              10

<210> SEQ ID NO 265
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 265
```
cgtctctcgt          10

<210> SEQ ID NO 266
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 266
tatcgattag          10

<210> SEQ ID NO 267
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 267
gttaatacga          10

<210> SEQ ID NO 268
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 268
tcgaaccggc          10

<210> SEQ ID NO 269
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 269
gtctaacgac          10

<210> SEQ ID NO 270
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 270
acaagtcgca          10

<210> SEQ ID NO 271
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 271
tatcgtacac          10

<210> SEQ ID NO 272
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 272 gtgcggtatc								10

<210> SEQ ID NO 273
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 273 actacgcatt								10

<210> SEQ ID NO 274
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 274 tgacggttcg								10

<210> SEQ ID NO 275
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 275 tacctaaccg								10

<210> SEQ ID NO 276
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 276 ataatggtcg								10

<210> SEQ ID NO 277
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 277 actcattccg								10

<210> SEQ ID NO 278
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 278 atcgttaacg								10

<210> SEQ ID NO 279
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 279
atgtcgcatc                                                          10

<210> SEQ ID NO 280
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 280
cgtactatta                                                          10

<210> SEQ ID NO 281
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 281
tagtgtcgcc                                                          10

<210> SEQ ID NO 282
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 282
ctacggttag                                                          10

<210> SEQ ID NO 283
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 283
taggctagcg                                                          10

<210> SEQ ID NO 284
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 284
cgattcggtt                                                          10

<210> SEQ ID NO 285
<211> LENGTH: 10
<212> TYPE: DNA
<213> ORGANISM: Artificial Sequence
<220> FEATURE:
<223> OTHER INFORMATION: synthetic construct; oligonucleotide

```
<400> SEQUENCE: 285
gatgcgacta                                                                   10

<210> SEQ ID NO 286
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 286
taagttaccg                                                                   10

<210> SEQ ID NO 287
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 287
ggtatgcgta                                                                   10

<210> SEQ ID NO 288
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 288
aaccgaacgt                                                                   10

<210> SEQ ID NO 289
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 289
tcacgataca                                                                   10

<210> SEQ ID NO 290
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 290
caattgccga                                                                   10

<210> SEQ ID NO 291
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 291
attaatatcg                                                                   10

<210> SEQ ID NO 292
```

```
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 292
caatccgtac                                                              10

<210> SEQ ID NO 293
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 293
ggtcgaataa                                                              10

<210> SEQ ID NO 294
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 294
cgcaataagg                                                              10

<210> SEQ ID NO 295
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 295
tactttcggt                                                              10

<210> SEQ ID NO 296
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 296
ctcgaccaaa                                                              10

<210> SEQ ID NO 297
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 297
gttgacgtat                                                              10

<210> SEQ ID NO 298
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 298
```
catcgctaga                                                          10

<210> SEQ ID NO 299
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 299
tgtcgcgtca                                                          10

<210> SEQ ID NO 300
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 300
cgcgcttatt                                                          10

<210> SEQ ID NO 301
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 301
cgagcatgta                                                          10

<210> SEQ ID NO 302
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 302
tagcgagtag                                                          10

<210> SEQ ID NO 303
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 303
gaccatagcg                                                          10

<210> SEQ ID NO 304
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 304
taatcaaccg                                                          10

<210> SEQ ID NO 305
<211> LENGTH: 10
<212> TYPE: DNA

```
<213> ORGANISM: Artificial Sequence
<220> FEATURE:
<223> OTHER INFORMATION: synthetic construct; oligonucleotide

<400> SEQUENCE: 305
gcaatcgttg                                                            10

<210> SEQ ID NO 306
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 306
attagtcgag                                                            10

<210> SEQ ID NO 307
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 307
cgccgtttga                                                            10

<210> SEQ ID NO 308
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 308
cgtttccgaa                                                            10

<210> SEQ ID NO 309
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 309
cgactgatca                                                            10

<210> SEQ ID NO 310
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 310
acgactaatg                                                            10

<210> SEQ ID NO 311
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 311
gttgtccgat                                                            10
```

```
<210> SEQ ID NO 312
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 312
acttatcgga                                                           10

<210> SEQ ID NO 313
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 313
gaactatcgt                                                           10

<210> SEQ ID NO 314
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 314
tatagtttcg                                                           10

<210> SEQ ID NO 315
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 315
atacggacaa                                                           10

<210> SEQ ID NO 316
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 316
taacgctagg                                                           10

<210> SEQ ID NO 317
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 317
cggtccgtat                                                           10

<210> SEQ ID NO 318
<211> LENGTH: 10
<212> TYPE: DNA
<213> ORGANISM: Artificial Sequence
<220> FEATURE:
```

<223> OTHER INFORMATION: synthetic construct; oligonucleotide

<400> SEQUENCE: 318
ttaaacggta                                                                10

<210> SEQ ID NO 319
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 319
tatcgcgtgt                                                                10

<210> SEQ ID NO 320
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 320
actagggtcg                                                                10

<210> SEQ ID NO 321
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 321
tctagcgaat                                                                10

<210> SEQ ID NO 322
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 322
taacatcgcc                                                                10

<210> SEQ ID NO 323
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 323
ttcaatccgg                                                                10

<210> SEQ ID NO 324
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 324
ttcgataact                                                                10

```
<210> SEQ ID NO 325
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 325
accgtctcga                                                            10

<210> SEQ ID NO 326
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 326
tatccgttcg                                                            10

<210> SEQ ID NO 327
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 327
cggtgtatat                                                            10

<210> SEQ ID NO 328
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 328
gggcatagcg                                                            10

<210> SEQ ID NO 329
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 329
taagctacgg                                                            10

<210> SEQ ID NO 330
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 330
tagaacgcga                                                            10

<210> SEQ ID NO 331
<211> LENGTH: 10
<212> TYPE: DNA
<213> ORGANISM: Artificial Sequence
<220> FEATURE:
<223> OTHER INFORMATION: synthetic construct; oligonucleotide
```

-continued

```
<400> SEQUENCE: 331
tgctaatcgc                                                                10

<210> SEQ ID NO 332
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 332
cgaaccgaac                                                                10

<210> SEQ ID NO 333
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 333
atcgtatggt                                                                10

<210> SEQ ID NO 334
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 334
tgtcgatcac                                                                10

<210> SEQ ID NO 335
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 335
cgtaccgatg                                                                10

<210> SEQ ID NO 336
<211> LENGTH: 10
<212> TYPE: DNA
<213> ORGANISM: Artificial Sequence
<220> FEATURE:
<223> OTHER INFORMATION: synthetic construct; oligonucleotide

<400> SEQUENCE: 336
atacatgcgg                                                                10
```

METHODS AND COMPOSITIONS FOR ENRICHING NON-HOST SEQUENCES IN HOST SAMPLES

CROSS-REFERENCE TO RELATED APPLICATION

This application claims the benefit of and priority under 35 U.S.C. § 371 of PCT/US2014/068644, filed Dec. 4, 2014, which claims the benefit under 35 U.S.C. § 119(e) of U.S. Provisional Application No. 61/911,642 filed Dec. 4, 2013, which are incorporated herein by reference in their entireties.

STATEMENT REGARDING FEDERALLY SPONSORED RESEARCH

This invention was made with government support under P20GM103395 awarded by Alaska INBRE through the National Institute of General Medical Sciences of the National Institutes of Health. The government has certain rights in the invention.

REFERENCE TO SEQUENCE LISTING

The Sequence Listing submitted Jun. 3, 2016 as a text file named "21002_0055U2_Sequence_Listing.txt", created on Jun. 2, 2016, and having a size of 71,124 bytes is hereby incorporated by reference pursuant to 37 C.F.R. § 1.52(e)(5).

The Sequence Listing submitted Jan. 9, 2019, as a text file named "21002_0055U2_Updated_Sequence_Listing.txt" created on Jan. 8, 2019, and having a size of 71,124 bytes is hereby incorporated by reference pursuant to 37 C.F.R. § 1.52(e)(5).

BACKGROUND

There is an increasing demand for public health laboratories to provide diagnoses and references of human pathogens in an accurate and timely manner, particularly in the context of an infectious disease outbreak where the pathogen is unknown. The biggest challenge with traditional diagnosis is people have to know what they are looking for. For example, a respiratory infection outbreak may be caused by any one of dozens of human pathogens, but the current practice can only detect one or a few of these pathogens at a time. This often results in delayed treatment and inconclusive diagnoses like the case of the SARS-coronavirus outbreak in China. This practice becomes especially problematic when an unknown infection or a complicated infectious disease case occurs. When unsure about the source of an infection, physicians must order a large number of diagnostic tests to cover a spectrum of pathogens. This is time intensive, financially costly, and physically uncomfortable for patients who must provide blood, sputum, and other tissue samples to support numerous diagnostic tests. There has been no alternative to this approach for diagnosis until very recently, with the development of next generation sequencing (NGS) technologies. The NGS technologies, including 2nd and 3rd generation DNA sequencing platforms, have started a revolution in genomics and provided opportunities for its broad application in many fields, including in the discovery of human pathogens. Currently, NGS technology is used as a research tool, rather than a diagnostic tool. The current limitations of NGS technology is due to the scarcity of pathogen sequences in human clinical samples, necessary subsequent requirement of extensive deep sequencing, and the complexity of bioinformatics analysis required in order to identify the pathogenic sequences. For example, the average viral genome in a human clinical sample is about 1-100 per 10 million human genome sequence reads, which usually require a deep sequencing and subsequent bioinformatics analysis to identify the viral sequences. It is a big challenge for diagnostic laboratories to diagnose unknown infections in a fast, accurate, and comprehensive manner. Many laboratories have developed various strategies to address this challenge, from consensus PCR assays that use degenerate primers to computational subtraction of large sequence data in order to find possible pathogens—with little success.

BRIEF SUMMARY

Disclosed are methods of enriching non-host nucleic acids from a host sample comprising selectively amplifying nucleic acids isolated from the host sample using non-host target primers to form an enriched population of non-host nucleic acids.

Disclosed are methods of enriching non-human nucleic acids from a human sample comprising selectively amplifying nucleic acids isolated from the human sample using non-human target primers to form an enriched population of non-human nucleic acids. In some aspects, the nucleic acids isolated from the human sample can be DNA or RNA.

Disclosed are methods of enriching non-human nucleic acids from a human sample comprising selectively reverse transcribing total or mRNA isolated from the human sample to form first cDNA strands using non-human target primers, wherein the first cDNA strands form an enriched population of non-human nucleic acids.

Disclosed are methods of enriching non-human nucleic acids from a human sample comprising reverse transcribing total RNA or mRNA isolated from the human sample to form first cDNA strands; and selectively amplifying the first cDNA strands with non-human target primers to form an enriched population of non-human nucleic acids.

Disclosed are methods of detecting non-host nucleic acids in a host sample comprising selectively amplifying nucleic acids isolated from the host sample using non-host target primers to form an enriched population of non-host nucleic acids; and detecting the non-host nucleic acids by sequencing the enriched population of non-host nucleic acids.

Disclosed are methods of detecting non-host nucleic acids in a host sample comprising selectively amplifying nucleic acids isolated from the host sample using non-host target primers to form an enriched population of non-host nucleic acids; and detecting the non-host nucleic acids by sequencing the enriched population of non-host nucleic acids, further comprising performing subtractive hybridization against a reference population of host cDNAs, wherein the subtractive hybridization results in a further enriched population of cDNAs, wherein the subtractive hybridization occurs prior to step of detecting.

Disclosed are methods of detecting a non-host sequence in a host sample comprising: selectively reverse transcribing total RNA or mRNA isolated from the host sample to form first cDNA strands using non-host target primers, wherein the first cDNA strands form an enriched population of non-host nucleic acids; and detecting the non-host sequence by sequencing the enriched population of non-host nucleic acids.

Disclosed are methods of detecting a non-host sequence in a host sample comprising: selectively reverse transcribing total RNA or mRNA isolated from the host sample to form first cDNA strands using non-host target primers, wherein the first cDNA strands form an enriched population of non-host nucleic acids; and detecting the non-host sequence by sequencing the enriched population of non-host nucleic acids, further comprising performing subtractive hybridization against a reference population of host cDNAs, wherein the subtractive hybridization results in a further enriched population of cDNAs, wherein the subtractive hybridization occurs prior to the step of detecting the non-host sequence by sequencing the enriched population of non-host nucleic acids.

Disclosed are methods of detecting non-host nucleic acids from a host sample comprising reverse transcribing total RNA or mRNA obtained from the host sample to form first cDNA strands; selectively amplifying the first cDNA strands with non-host target primers to form an enriched population of non-host nucleic acids; and detecting the non-host sequence by sequencing the enriched population of non-host nucleic acids.

Disclosed are methods of detecting non-host nucleic acids from a host sample comprising reverse transcribing total RNA or mRNA obtained from the host sample to form first cDNA strands; selectively amplifying the first cDNA strands with non-host target primers to form an enriched population of non-host nucleic acids; and detecting the non-host sequence by sequencing the enriched population of non-host nucleic acids, further comprising performing subtractive hybridization against a reference population of host cDNAs, wherein the subtractive hybridization results in a further enriched population of cDNAs, wherein the subtractive hybridization occurs prior to step of detecting.

The disclosed methods can further comprise performing subtractive hybridization against a population of reference human cDNAs, wherein the subtractive hybridization results in a further enriched population of non-human nucleic acids. Non-human target primers can be eight, nine, ten, or eleven nucleotides in length. In some aspects, non-human target primers do not hybridize to the most abundant human transcripts. In some aspects, the most abundant human transcripts can comprise at least 65% of all human transcripts. In some aspects, the most abundant human transcripts can be greater than 200 base pairs in length. In some aspects, the most abundant human transcripts can be the 1000, 2000, 3000, 4000, 5000, 6000, 7000, 8000, 9000, 10000, 20000 most abundant human transcripts or whole human transcriptome identified in the ENCODE database.

Non-human target primers can comprise one or more of the oligonucleotides in FIG. 10 or 11.

Non-human nucleic acids can be pathogenic sequences. For example, pathogenic sequences can be from viruses, bacteria, fungi, or any infectious agents.

Disclosed are methods of enriching non-host nucleic acids in a host sample, wherein the non-host nucleic acids can be, but is not limited to, non-human nucleic acids. The non-human nucleic acids can be pathogenic sequences. For example, the pathogenic sequences can be sequences from viruses, bacteria, fungi, protozoa, parasites or any infectious agent.

Disclosed are methods of detecting non-host sequences in a host sample, wherein detecting non-host sequences can be achieved by detecting the enriched population of non-host nucleic acids. The detection can be performed using any known molecular biology technique, such as NGS technology, Sanger sequencing, ensemble sequencing, capillary electrophoresis, single molecule sequencing, hybridization, or microarray.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 4 shows Next Generation Sequencing (NGS) instruments and comparison of their capacities.

FIGS. 5A and 5B are tables showing the generation of sample identifiers (barcodes) through the combination of 20+20 adaptors.

FIG. 6 shows the number of short oligos that do not match to the most abundant human transcripts.

FIG. 7 shows the percentage of human viruses that can be covered by short oligos. K-mers total number: Number of total short oligos that match to the human virome (can have multiple matches within one virus); K-mers number in short list: Number of total short oligos that match at least one site for each virus.

FIG. 9 is a table showing the percent of the sequences in the virome covered by the oligos.

FIG. 10 is a table showing 179 10mers that exclude the top 10,000 human transcripts. Starting from the left column and going top to bottom, the sequences in FIG. 10 are SEQ ID NOs:42-190. For example, from top to bottom in the first column are SEQ ID NOs:42-75; from top to bottom in the second column are SEQ ID NOs:76-109; from top to bottom in the third column are SEQ ID NOs:110-143; from top to bottom in the fourth column are SEQ ID NOs:144-177; from top to bottom in the last column are SEQ ID NOs:178-190.

FIG. 11 is a table showing 171 10mers that exclude the top 20,000 human transcripts. Starting from the left column and going top to bottom, the sequences in FIG. 10 are SEQ ID NOs:191-336. For example, from top to bottom in the first column are SEQ ID NOs:191-225; from top to bottom in the second column are SEQ ID NOs:226-260; from top to bottom in the third column are SEQ ID NOs:261-295; from top to bottom in the fourth column are SEQ ID NOs:296-330; from top to bottom in the last column are SEQ ID NOs:331-336.

DETAILED DESCRIPTION

Figure 1:
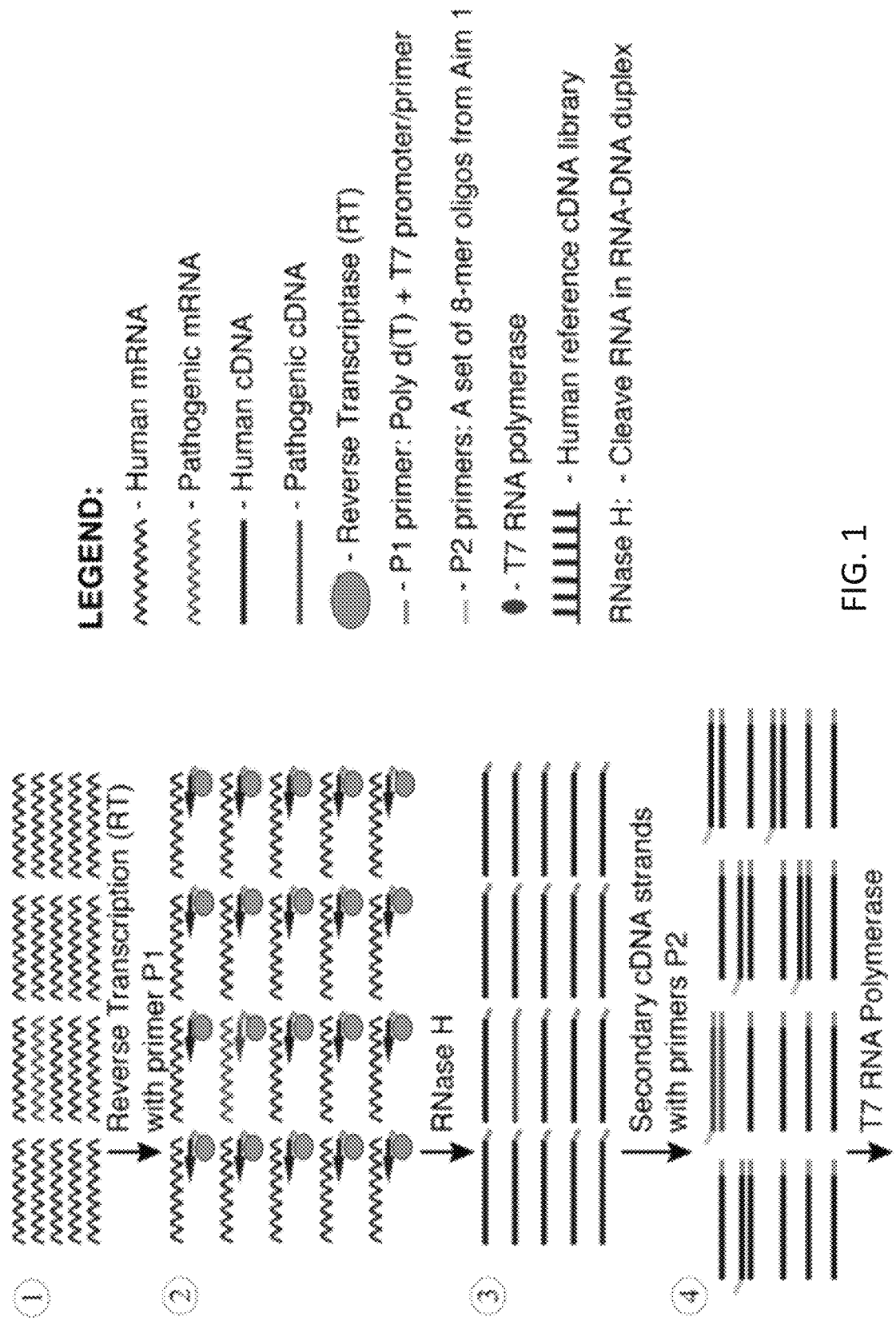
FIG. 1 is a schematic representation of one embodiment, the PATHseq (Preferential Amplification of Pathogenic Sequences) method. (1) Total mRNAs from clinical sample, including human mRNAs and relatively scarce pathogenic mRNAs; (2) Total mRNAs are transcribed into first strand cDNAs with P1 primer; (3) RNase H cleaves RNAs in RNA-DNA duplex; (4) Reverse transcriptase (RT) synthesizes secondary cDNA strands with P2 primers; (5) T7 RNA polymerase synthesizes RNAs in the presence of T7 promoter; (6) Synthesized anti-sense RNAs; (7) Synthesized RNAs are hybridized to human reference (non-pathogenic) cDNA library. RNase H cleaves bound RNAs (human RNAs) in RNA-DNA duplex; (8) Pathogenic RNAs are enriched; (9) Reverse transcription; (10) RNase H cleaves RNAs in RNA-DNA duplex; (11) T7 RNA polymerase synthesizes RNAs; (12) New RNAs synthesized from enriched pathogenic RNAs are amplified 100-1000 fold.
Figure 1:
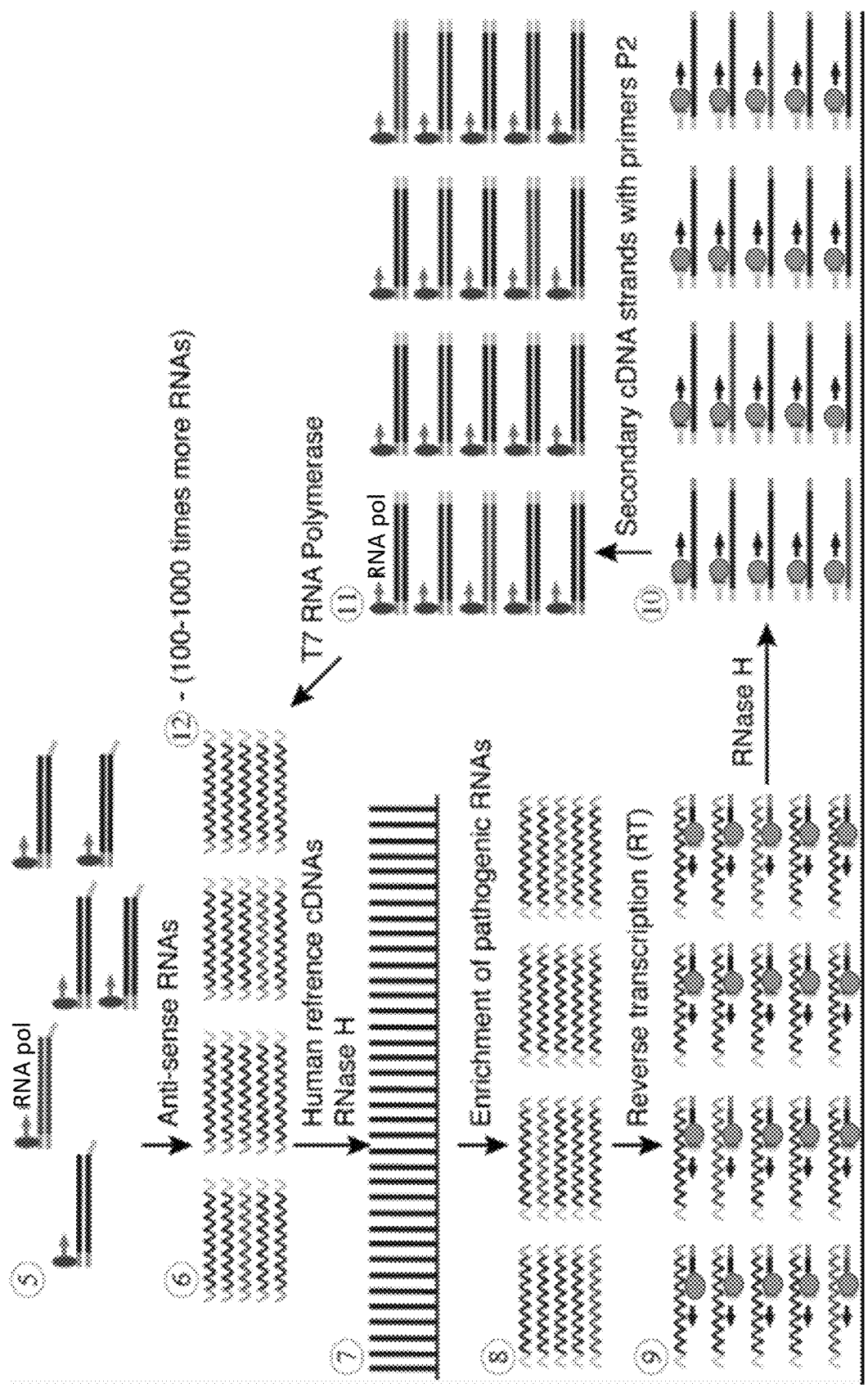

The disclosed method and compositions may be understood more readily by reference to the following detailed description of particular embodiments and the example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

The phrase "non-host target primers" refers to oligonucleotides that can serve as primers that are designed to not hybridize to host transcripts. In some aspects, the non-host target primers are designed such that they do not hybridize to the most abundant host transcripts.

The phrase "non-human target primers" refers to oligonucleotides that can serve as primers that are designed to not hybridize to one or more human transcripts. In some aspects, the non-human target primers are designed such that they do not hybridize to the most abundant human transcripts. For example, the most abundant human transcripts can be the top 1000, 2000, or 4000 transcripts found in the human transcriptome. Non-human target primers can be eight, nine, then or eleven nucleotides in length. In some aspects, the non-human target primers can comprise one or more of the sequences in Tables 5-8 or 3. For example, the non-human target primers can be one or more of the sequences in Table 6.

"Non-host nucleic acids" refers to nucleic acids exogenous to the nucleic acids of the host. Non-host nucleic acids can also be referred to as non-host sequences.

"Non-human nucleic acids" refers to exogenous nucleic acids to the nucleic acids of a human. Non-human nucleic acids can also be referred to as non-human sequences.

"Host specific DNA" refers to the host's own DNA. For example, if the host is human then human specific DNA refers to DNA present in the human genome. If a human had a viral infection, the human specific DNA would not include the viral DNA present in the human.

The term "host" refers to the biological organism from which nucleic acids are isolated. For example, a host can be, but is not limited to, a human, plant, animal such as dog, cat, horse, or cow.

The term "host sample" refers to a biological sample obtained from the host. Examples of biological samples include, but are not limited to, biological fluids, cells, tissue, hair, and any combinations thereof. Examples of biological fluids include, but are not limited to, saliva, blood, sputum, urine, an aspirate, a secretion, and any combinations thereof.

The phrase "selectively amplifying" refers to the amplification of nucleic acids with primers that allow for amplification of selected targets (i.e. non-host nucleic acids).

"Reference host cDNA population" refers to a control cDNA population wherein the control is a control for the host sample. A reference cDNA population is a cDNA population comprising substantially pure host cDNAs and free from other substances or non-host cDNAs. For example, if the host is a human, then a reference host cDNA population would be a pathogen-free human cDNA population.

The term "purification" or "pure" (e.g., with respect to a cDNA population or a composition containing a pathogen) refers to the process of removing components from a composition, the presence of which is not desired. Purification is a relative term, and does not require that all traces of the undesirable component be removed from the composition. In the context of a reference host cDNA population, purification includes such processes as centrifugation, amplification or precipitation. Thus, the term "purified" does not require absolute purity; rather, it is intended as a relative term. Thus, for example, a purified cDNA preparation or population is one in which the cDNA is more enriched than it is in its generative environment, for instance within a cell or population of cells or other nucleic acids in which it is replicated naturally or in an artificial environment. A preparation of substantially pure cDNA population can be purified such that the desired cDNA represents at least 50% of the total nucleic acid content of the preparation. In certain embodiments, a substantially pure cDNA population will represent at least 60%, at least 70%, at least 80%, at least 85%, at least 90%, or at least 95% or more of the total nucleic acid content of the preparation.

It must be noted that as used herein and in the appended claims, the singular forms "a", "an", and "the" include plural reference unless the context clearly dictates otherwise. Thus, for example, reference to "a non-host target primer" can include a plurality of such primers, reference to "the host sample" can be a reference to one or more host samples and equivalents thereof known to those skilled in the art, and so forth.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

B. Methods of Enriching

Disclosed are methods of enriching non-host nucleic acids from a host sample comprising selectively amplifying nucleic acids isolated from the host sample using non-host target primers to form an enriched population of non-host nucleic acids. The non-host nucleic acids isolated or obtained from a host sample can be DNA or RNA.

In some aspects, the host can be a human. Thus, disclosed are methods of enriching non-human nucleic acids from a human sample comprising selectively amplifying nucleic acids isolated from the human sample using non-human target primers to form an enriched population of non-human nucleic acids.

Enriching non-host nucleic acids from a host sample allows for an increase in the ratio of non-host to host nucleic acids. The increased ratio of non-host nucleic acids provides an increased quantity of non-host nucleic acids, which can result in easier detection of the non-host nucleic acids. For example, if the initial host sample contains an average 1-10 pathogenic sequences in 1 million host sequences, the disclosed methods can enrich the pathogenic sequences about 1,000 times. Thus, about 0.1-1% of the sample would be enriched pathogenic sequences 1. Methods of Enriching DNA Disclosed are methods of enriching non-host nucleic acids from a host sample comprising selectively amplifying nucleic acids isolated from the host sample using non-host target primers to form an enriched population of non-host nucleic acids, wherein the nucleic acids isolated from the host sample are DNA.

Disclosed are methods of enriching non-host nucleic acids from a host sample comprising selectively amplifying nucleic acids isolated from the host sample using non-host target primers to form an enriched population of non-host nucleic acids, wherein the nucleic acids isolated from the host sample are DNA, wherein the non-host target primers are eight, nine, ten, or eleven nucleotides in length.

Disclosed are methods of enriching non-host nucleic acids from a host sample comprising selectively amplifying nucleic acids isolated from the host sample using non-host target primers to form an enriched population of non-host nucleic acids, wherein the nucleic acids isolated from the host sample are DNA, wherein the non-host target primers do not hybridize to the most abundant host transcripts. In some aspects, the most abundant host transcripts comprise at least 65% of all host transcripts. In some aspects, the most abundant host transcripts can be greater than 200 base pairs in length. In some aspects, the most abundant host transcripts can be the 1000, 2000, 3000, 4000, 5000, 6000, 7000, 8000, 9000, 10000, 20000 most abundant human transcripts or whole host transcriptome identified in the ENCODE database.

Disclosed are methods of enriching non-host nucleic acids from a host sample comprising selectively amplifying nucleic acids isolated from the host sample using non-host target primers to form an enriched population of non-host nucleic acids, wherein the nucleic acids isolated from the host sample are DNA, wherein the non-host target primers comprise one or more of the oligonucleotides in Table 5-8.

Disclosed are methods of enriching non-host nucleic acids from a host sample comprising selectively amplifying nucleic acids isolated from the host sample using non-host target primers to form an enriched population of non-host nucleic acids, wherein the nucleic acids isolated from the host sample are DNA, wherein the non-host sequences can be pathogenic sequences. In some aspects, the pathogenic sequences can be from viruses, bacteria, fungi, or any infectious agents.

In some aspects, the host can be a human. Thus, disclosed are methods of enriching non-human nucleic acids from a human sample comprising selectively amplifying nucleic acids isolated from the human sample using non-human target primers to form an enriched population of non-human nucleic acids, wherein the nucleic acids isolated from the human sample are DNA.

Disclosed are methods of enriching non-human nucleic acids from a human sample comprising selectively amplifying nucleic acids isolated from the human sample using non-human target primers to form an enriched population of non-human nucleic acids, wherein the nucleic acids isolated from the human sample are DNA, wherein the non-human target primers are eight, nine, ten, or eleven nucleotides in length.

Disclosed are methods of enriching non-human nucleic acids from a human sample comprising selectively amplifying nucleic acids isolated from the human sample using non-human target primers to form an enriched population of non-human nucleic acids, wherein the nucleic acids isolated from the human sample are DNA, wherein the non-human target primers do not hybridize to the most abundant human transcripts. In some aspects, the most abundant human transcripts comprise at least 65% of all human transcripts. In some aspects, the most abundant human transcripts can be greater than 200 base pairs in length. In some aspects, the most abundant human transcripts can be the 1000, 2000, 3000, 4000, 5000, 6000, 7000, 8000, 9000, 10000, 20000 most abundant human transcripts or whole human transcriptome identified in the ENCODE database.

Disclosed are methods of enriching non-human nucleic acids from a human sample comprising selectively amplifying nucleic acids isolated from the human sample using non-human target primers to form an enriched population of non-human nucleic acids, wherein the nucleic acids isolated from the human sample are DNA, wherein the non-human target primers comprise one or more of the oligonucleotides in FIG. 10 or 11.

Disclosed are methods of enriching non-human nucleic acids from a human sample comprising selectively amplifying nucleic acids isolated from the human sample using non-human target primers to form an enriched population of non-human nucleic acids, wherein the nucleic acids isolated from the human sample are DNA, wherein the non-human nucleic acids can be pathogenic sequences. In some aspects, the pathogenic sequences can be from viruses, bacteria, fungi, or any infectious agents.

i. Isolating

Methods of enriching non-host nucleic acids from a host sample can include the isolation of DNA from a host sample. DNA isolated from a host sample can include host specific DNA as well as DNA from any non-host pathogens that may be present within the host. DNA can be isolated from a host sample and used as a template for non-host target primers. Techniques well-known in the art can be used to DNA from a sample.

ii. Selectively Amplifying

Selectively amplifying DNA isolated from a host sample with non-host target primers can form an enriched population of non-host nucleic acids.

Non-host target primers can be used to selectively amplify non-host cDNA. The non-host target primers are designed to hybridize to non-host sequences and not to hybridize to host sequences. In some aspects, the non-host target primers do not hybridize to the most abundant host transcripts. For example, non-human target primers can be used that do not hybridize to the most abundant human transcripts. Any of the non-host target primers disclosed herein can be used. For example, when the host is human, the non-host (i.e. non-human) target primers can be one or more of the primers comprising the sequences in FIG. 10 or 11. In some aspects, the non-human target primers can be one or more sequences in Table 3.

Non-host target primers can hybridize to non-host DNA and can serve to prime synthesis of non-host DNA.

In some aspects, RNAs can be synthesized from dsDNA. Any DNA dependent RNA polymerase can be used for synthesis of RNA from dsDNA. For example, T7 RNA polymerase can be used. Other RNA polymerases such as, but not limited to, T3 and SP6 RNA polymerases can also be used.

The resulting RNAs can be RNA copies of the selectively amplified DNAs. Therefore, the RNA copies can be considered selective RNAs or an enriched RNA population. The selective RNAs comprise RNA copies of non-host DNA sequences. In some aspects, selective RNAs can be antisense RNAs.

Selective amplification results in an enriched population of non-host nucleic acids. In some aspects, the enriched population of non-host nucleic acids can comprise a DNA population that contains a higher percentage of non-host nucleic acids compared to the DNA population before selective amplification.

iii. Subtractive Hybridization

In some aspects, subtractive hybridization can be performed after the selective amplification. Thus, disclosed are methods of enriching non-host nucleic acids from a host sample comprising selectively amplifying nucleic acids isolated from the host sample using non-host target primers to form an enriched population of non-host nucleic acids, wherein the nucleic acids are DNA, further comprising performing subtractive hybridization against a population of reference host nucleic acids, wherein the subtractive hybridization results in a further enriched population of non-host nucleic acids. The reference host nucleic acids can be, but are not limited to, cDNAs.

Because the host sample can be a human sample, the disclosed methods include methods of enriching non-human nucleic acids from a human sample comprising selectively amplifying nucleic acids isolated from the human sample using non-human target primers to form an enriched population of non-human nucleic acids, wherein the nucleic acids are DNA, further comprising performing subtractive hybridization against a population of reference human nucleic acids, wherein the subtractive hybridization results in a further enriched population of non-human nucleic acids.

Performing subtractive hybridization can further enrich the enriched population of non-host nucleic acids previously enriched by selectively amplifying non-host sequences with non-host target primers.

Subtractive hybridization comprises the subtraction or removal of unwanted nucleic acids (e.g. host nucleic acids). Subtractive hybridization can comprise hybridizing the selective or enriched nucleic acids with a reference host cDNA population. Reference host cDNA populations can be created using techniques well-known in the art. In some instances, a reference host cDNA population can be one or more commercially available host cDNA libraries, such as, but not limited to, a human peripheral blood mononuclear cell (PBMC) cDNA library.

Subtractive hybridization can comprise hybridization between selective or enriched nucleic acids and a reference host cDNA population. For example, the enriched population of non-host nucleic acids can be reverse transcribed to make a selective or enriched RNA population. The selective or enriched RNA population can hybridize to the reference host cDNA population. If any of the RNAs are host RNAs, then the host RNA can hybridize to the reference host cDNA population form an RNA/DNA duplex and can be removed using RNase H. Thus, the remaining RNAs would be the selective RNAs that did not hybridize to the reference host cDNA population and therefore would be considered non-host nucleic acids. The removal of any host RNAs that were present in the selective or enriched RNA population can result in a further enriched RNA population comprising non-host RNAs.

After subtractive hybridization, the further enriched RNA population can be reverse transcribed and the methods described below can be performed or the cDNA produced from the reverse transcription can then be selectively amplified using the method described herein. For example, the enrichment steps can be repeated continuously to increase the amount of non-host nucleic acids. In one aspect, the further enriched RNA population can be reverse transcribed to form a first cDNA strand; the first cDNA strand can be selectively amplified with non-host target primers to form a second enriched population of non-host nucleic acids. The second enriched population of non-host nucleic acids can undergo selective hybridization resulting in a second further enriched RNA population. The cycle of reverse transcription, selective amplification, and subtractive hybridization can be repeated indefinitely.

2. Methods of Enriching RNA i. Selective Reverse Transcription

Disclosed are methods of enriching non-host nucleic acids from a host sample comprising selectively reverse transcribing total or mRNA isolated from the host sample to form first cDNA strands using non-host target primers, wherein the first cDNA strands form an enriched population of non-host nucleic acids.

Disclosed are methods of enriching non-host nucleic acids from a host sample comprising selectively reverse transcribing total or mRNA isolated from the host sample to form first cDNA strands using non-host target primers, wherein the first cDNA strands form an enriched population of non-host nucleic acids, wherein the non-host target primers are eight, nine, ten, or eleven nucleotides in length.

Disclosed are methods of enriching non-host nucleic acids from a host sample comprising selectively reverse transcribing total or mRNA isolated from the host sample to form first cDNA strands using non-host target primers, wherein the first cDNA strands form an enriched population of non-host nucleic acids, wherein the non-host target primers do not hybridize to the most abundant host transcripts. In some aspects, the most abundant host transcripts comprise at least 65% of all host transcripts. In some aspects, the most abundant host transcripts can be greater than 200 base pairs in length. In some aspects, the most abundant host transcripts can be the 1000, 2000, 3000, 4000, 5000, 6000, 7000, 8000, 9000, 10000, 20000 most abundant human transcripts or whole host transcriptome identified in the ENCODE database.

Disclosed are methods of enriching non-host nucleic acids from a host sample comprising selectively reverse transcribing total or mRNA isolated from the host sample to form first cDNA strands using non-host target primers, wherein the non-host target primers comprise the complement of one or more of the oligonucleotides in Table 5-8.

Disclosed are methods of enriching non-host nucleic acids from a host sample comprising selectively reverse transcribing total or mRNA isolated from the host sample to form first cDNA strands using non-host target primers, wherein the first cDNA strands form an enriched population of non-host nucleic acids, wherein the non-host sequences can be pathogenic sequences. In some aspects, the pathogenic sequences can be from viruses, bacteria, fungi, or any infectious agents.

In some aspects the host can be a human. Thus, disclosed are methods of enriching non-human nucleic acids from a human sample comprising selectively reverse transcribing total or mRNA isolated from the human sample to form first cDNA strands using non-human target primers, wherein the first cDNA strands form an enriched population of non-human nucleic acids.

Disclosed are methods of enriching non-human nucleic acids from a human sample comprising selectively reverse transcribing total or mRNA isolated from the human sample to form first cDNA strands using non-human target primers, wherein the first cDNA strands form an enriched population of non-human nucleic acids, wherein the non-human target primers are eight, nine, ten, or eleven nucleotides in length.

Disclosed are methods of enriching non-human nucleic acids from a human sample comprising selectively reverse transcribing total or mRNA isolated from the human sample to form first cDNA strands using non-human target primers, wherein the first cDNA strands form an enriched population of non-human nucleic acids, wherein the non-human target primers do not hybridize to the most abundant human transcripts. In some aspects, the most abundant human transcripts comprise at least 65% of all human transcripts. In some aspects, the most abundant human transcripts can be greater than 200 base pairs in length. In some aspects, the most abundant human transcripts can be the 1000, 2000, 3000, 4000, 5000, 6000, 7000, 8000, 9000, 10000, 20000 most abundant human transcripts or whole human transcriptome identified in the ENCODE database.

Disclosed are methods of enriching non-human nucleic acids from a human sample comprising selectively reverse transcribing total or mRNA isolated from the human sample to form first cDNA strands using non-human target primers, wherein the first cDNA strands form an enriched population of non-human nucleic acids, wherein the non-human target primers comprise one or more of the oligonucleotides in Table 5-8.

Disclosed are methods of enriching non-human nucleic acids from a human sample comprising selectively reverse transcribing total or mRNA isolated from the human sample to form first cDNA strands using non-human target primers, wherein the first cDNA strands form an enriched population of non-human nucleic acids, wherein the non-human nucleic acids can be pathogenic sequences. In some aspects, the pathogenic sequences can be from viruses, bacteria, fungi, or any infectious agents.

a. Isolating

Methods of enriching non-host nucleic acids from a host sample can include the isolation of total RNA or mRNA from a host sample. Total RNA or mRNA can be isolated from a host sample and used as a template for creating first cDNA strands. Techniques well-known in the art can be used to isolate total RNA or mRNA from a sample.

b. Reverse Transcribing and Selective Amplification Combined

Non-host target primers can be used to selectively amplify total RNA or mRNA. The non-host target primers are designed to hybridize non-host sequences and not to hybridize to host sequences. The complement of any of the non-host target primers disclosed herein can be used. For example, when the host is human, the non-host (i.e. non-human) target primers can be one or more of the primers comprising the complement of the sequences in FIG. 10 or 11. In some aspects, the non-human target primers can be one or more of the complement of the sequences in Table 3.

Non-host target primers can hybridize to non-host total RNA or mRNA and can serve to prime synthesis of non-host cDNA strands.

The combination of reverse transcription and selective amplification can also be known as selective reverse transcription.

c. Subtractive Hybridization

In some aspects, a further step of subtractive hybridization can be performed.

Thus, disclosed are methods of enriching non-host nucleic acids from a host sample comprising selectively reverse transcribing total or mRNA isolated from the host sample to form first cDNA strands using non-host target primers, wherein the first cDNA strands form an enriched population of non-host nucleic acids, further comprising performing subtractive hybridization against a population of reference host cDNAs, wherein the subtractive hybridization results in a further enriched population of non-host nucleic acids.

Because the host sample can be a human sample, the disclosed methods include methods of enriching non-human nucleic acids from a human sample comprising selectively reverse transcribing total or mRNA isolated from the human sample to form first cDNA strands using non-human target primers, wherein the first cDNA strands form an enriched population of non-human nucleic acids, further comprising performing subtractive hybridization against a population of reference human cDNAs, wherein the subtractive hybridization results in a further enriched population of non-human cDNAs.

Performing subtractive hybridization can further enrich the enriched population of non-host nucleic acids previously enriched by selectively reverse transcribing non-host sequences with non-host target primers.

Subtractive hybridization comprises the subtraction or removal of unwanted nucleic acids (e.g. host nucleic acids). Subtractive hybridization can comprise hybridizing the selective or enriched RNAs with a reference host cDNA population. Reference host cDNA populations can be created using techniques well-known in the art. In some instances, a reference host cDNA population can be one or more commercially available host cDNA libraries, such as, but not limited to, a human peripheral blood mononuclear cell (PBMC) cDNA library.

The enriched population of non-host nucleic acids can be reverse transcribed to form an enriched or selective population of RNA. Subtractive hybridization can comprise hybridization between selective or enriched RNA and a reference host cDNA population. Any host RNAs present in the selective RNAs can hybridize to the reference host cDNA population. Host RNAs hybridized to the reference host cDNA population form an RNA/DNA duplex and can be removed using RNase H. Thus, the remaining RNAs would be the selective RNAs that did not hybridize to the reference host cDNA population and therefore would be considered non-host nucleic acids. The removal of any host RNAs that were present in the selective or enriched RNA population can result in a further enriched RNA population comprising non-host RNAs.

After subtractive hybridization, the further enriched RNA population can be treated as the original RNA obtained from the sample and the further enriched RNA population can be used to repeat one or more of the steps described above. For example, the enrichment steps can be repeated continuously to increase the amount of non-host nucleic acids. In one aspect, the further enriched RNA population can be selectively reverse transcribed using non-host target primers to form a second enriched population of non-host nucleic acids. The cycle of selective reverse transcription and subtractive hybridization can be repeated indefinitely.

ii. Reverse Transcription and then Selective Amplification

Disclosed are methods of enriching non-host nucleic acids from a host sample comprising reverse transcribing total RNA or mRNA obtained from the host sample to form first cDNA strands; and selectively amplifying the first cDNA strands with non-host target primers to form an enriched population of non-host nucleic acids.

Disclosed are methods of enriching non-host nucleic acids from a host sample comprising reverse transcribing total RNA or mRNA obtained from the host sample to form first cDNA strands; and selectively amplifying the first cDNA strands with non-host target primers to form an enriched population of non-host nucleic acids, wherein the non-host target primers are eight, nine, ten, or eleven nucleotides in length.

Disclosed are methods of enriching non-host nucleic acids from a host sample comprising reverse transcribing total RNA or mRNA obtained from the host sample to form first cDNA strands; and selectively amplifying the first cDNA strands with non-host target primers to form an enriched population of non-host nucleic acids, wherein the non-host target primers do not hybridize to the most abundant host transcripts. In some aspects, the most abundant host transcripts comprise at least 65% of all host transcripts. In some aspects, the most abundant host transcripts can be greater than 200 base pairs in length. In some aspects, the most abundant host transcripts can be the 1000, 2000, 3000, 4000, 5000, 6000, 7000, 8000, 9000, 10000, 20000 most abundant human transcripts or whole host transcriptome identified in the ENCODE database.

Disclosed are methods of enriching non-host nucleic acids from a host sample comprising reverse transcribing total RNA or mRNA obtained from the host sample to form first cDNA strands; and selectively amplifying the first cDNA strands with non-host target primers to form an enriched population of non-host nucleic acids, wherein the non-host target primers comprise one or more of the oligonucleotides in FIG. 10 or 11.

Disclosed are methods of enriching non-host nucleic acids from a host sample comprising reverse transcribing total RNA or mRNA obtained from the host sample to form first cDNA strands; and selectively amplifying the first cDNA strands with non-host target primers to form an enriched population of non-host nucleic acids, wherein the non-host sequences can be pathogenic sequences. In some aspects, the pathogenic sequences can be from viruses, bacteria, fungi, or any infectious agents.

In some aspects, the host can be a human. Thus, also disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids.

Disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids, wherein the non-human target primers are eight, nine, ten, or eleven nucleotides in length.

Disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids, wherein the non-human target primers do not hybridize to the most abundant human transcripts. In some aspects, the most abundant human transcripts comprise at least 65% of all human transcripts. In some aspects, the most abundant human transcripts can be greater than 200 base pairs in length. In some aspects, the most abundant human transcripts can be the 1000, 2000, 3000, 4000, 5000, 6000, 7000, 8000, 9000, 10000, 20000 most abundant human transcripts or whole human transcriptome identified in the ENCODE database.

Disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids, wherein the non-human target primers comprise one or more of the oligonucleotides in FIG. 10 or 11.

Disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids, wherein the non-human nucleic acids can be pathogenic sequences. In some aspects, the pathogenic sequences can be from viruses, bacteria, fungi, or any infectious agents.

a. Isolating

Methods of enriching non-host nucleic acids from a host sample can include the isolation of total RNA or mRNA from a host sample. Total RNA or mRNA can be isolated from a host sample and used as a template for creating first cDNA strands. Techniques well-known in the art can be used to isolate total RNA or mRNA from a sample.

b. Reverse Transcribing

Isolated total RNA or mRNA obtained from a host sample can be used as the template for creating a first cDNA strand for each of the isolated total RNA or mRNAs. Methods for reverse transcribing mRNA are well-known in the art. For example, a poly d(T) primer in combination with reverse transcriptase can be used to produce a first cDNA strand from mRNA.

Reverse transcriptases have RNA dependent DNA polymerase activity and thus can produce a cDNA strand from an RNA template. In some instances, reverse transcriptases can further comprise RNase H activity, which results in the cleavage of RNA from an RNA-DNA duplex. In some instances, RNase H can be added separately from the reverse transcriptase.

Several types of primers can be used during reverse transcription. For example, the primers can be but are not limited to random primers, sequence specific primers, and/or poly d(T) primers. When reverse transcribing total RNA, random primers and poly d(T) primers are often used since the sequences of the RNA may not be known.

Figures 2, 3:
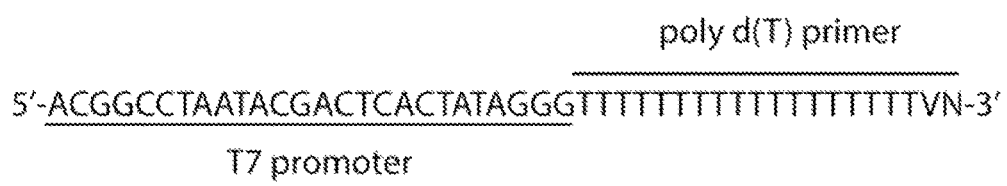
FIG. 2 shows P1 (Poly d(T)-T7 promoter) primer used to form first cDNA strands. The sequence shown in FIG. 2 is SEQ ID NO:41.
FIG. 3 shows numbers of oligonucleotides that do not match the sequences of human transcripts.

In some aspects, the primers can be poly d(T) primers further comprising an RNA polymerase promoter sequence. Thus, a poly d(T)-RNA polymerase promoter primer can be used to form first cDNA strands from a host sample comprising reverse transcribing mRNA obtained from the host sample. In some aspects, the poly d(T)-RNA polymerase promoter primer can comprise poly d(T)-T7 promoter sequences as shown in FIG. 2. Promoter sequences for other RNA polymerases such as, but not limited to, T3 and SP6 RNA polymerases can also be used.

c. Selectively Amplifying

The first cDNA strands produced from reverse transcribing total RNA or mRNA obtained from a host sample can be used for selective amplification. Selectively amplifying the first cDNA strands with non-host target primers can form an enriched population of non-host nucleic acids.

Before selectively amplifying the first cDNA strands, the total RNA or mRNA that served as the template for the first cDNA strand can be removed. Removal of the total RNA or mRNA can be performed by adding RNase H before selective amplification. In some instances, the RNA dependent DNA polymerase used to produce the first cDNA strand can have RNase H activity. In some instances, RNase H can be added as a separate enzyme independent of the DNA polymerase. After removing the total RNA or mRNA, or after selectively isolating the first cDNA strands, only first cDNA strands remain.

Non-host target primers can be used to selectively amplify non-host cDNA. The non-host target primers are designed to hybridize non-host sequences and not to hybridize to host sequences. Any of the non-host target primers disclosed herein can be used. For example, when the host is human, the non-host (i.e. non-human) target primers can be one or more of the primers comprising the sequences in FIG. 10 or 11. In some aspects, the non-human target primers can be one or more sequences in Table 3.

Non-host target primers can hybridize to non-host first cDNA strands and can serve to prime synthesis of second non-host cDNA strand.

RNAs can also be synthesized from dsDNA. For example, RNA can be synthesized from dsDNA comprising non-host first cDNA strand and non-host second cDNA strands. Any DNA dependent RNA polymerase can be used for synthesis of RNA from dsDNA. For example, T7 RNA polymerase can be used. Other RNA polymerases such as, but not limited to, T3 and SP6 RNA polymerases can also be used.

The resulting RNAs can be RNA copies of the selectively amplified cDNAs. Therefore, the RNA copies can be considered selective RNAs or an enriched RNA population. The selective RNAs comprise RNA copies of non-host cDNA sequences. In some aspects, selective RNAs can be antisense RNAs.

Selective amplification results in an enriched population of non-host nucleic acids. In some aspects, the enriched population of non-host nucleic acids can comprise a cDNA population that contains a higher percentage of non-host nucleic acids compared to the cDNA population before selective amplification. In some aspects, the enriched population of non-host nucleic acids can comprise a population of RNAs that contains a higher percentage of non-host RNA sequences compared to the mRNA obtained from the host sample.

d. Subtractive Hybridization

Disclosed are methods of enriching non-host nucleic acids from a host sample comprising reverse transcribing mRNA isolated from the host sample to form first cDNA strands; and selectively amplifying the first cDNA strands with non-host target primers to form an enriched population of non-host nucleic acids, further comprising performing subtractive hybridization against a population of reference host cDNAs, wherein the subtractive hybridization results in a further enriched population of non-human cDNAs.

Because the host sample can be a human sample, the disclosed methods include methods of enriching non-human nucleic acids from a human sample comprising reverse transcribing mRNA isolated from the human sample to form first cDNA strands; and selectively amplifying the first cDNA strands with non-human target primers to form an enriched population of non-human nucleic acids, further comprising performing subtractive hybridization against a population of reference human cDNAs, wherein the subtractive hybridization results in a further enriched population of non-human cDNAs.

Performing subtractive hybridization can further enrich the enriched population of non-host nucleic acids previously enriched by selectively amplifying non-host sequences with non-host target primers.

Subtractive hybridization comprises the subtraction or removal of unwanted nucleic acids (e.g. host nucleic acids). Subtractive hybridization can comprise hybridizing the selective or enriched RNAs with a reference host cDNA population. Reference host cDNA populations can be created using techniques well-known in the art. In some instances, a reference host cDNA population can be one or more commercially available host cDNA libraries, such as, but not limited to, a human peripheral blood mononuclear cell (PBMC) cDNA library.

Subtractive hybridization can comprise hybridization between selective or enriched RNA and a reference host cDNA population. Any host RNAs present in the selective RNAs can hybridize to the reference host cDNA population. Host RNAs hybridized to the reference host cDNA population form an RNA/DNA duplex and can be removed using RNase H. Thus, the remaining RNAs would be the selective RNAs that did not hybridize to the reference host cDNA population and therefore would be considered non-host nucleic acids. The removal of any host RNAs that were present in the selective or enriched RNA population can result in a further enriched RNA population comprising non-host RNAs.

After subtractive hybridization, the further enriched RNA population can be treated as the original RNA obtained from the sample and the further enriched RNA population can be used to repeat one or more of the steps described above. For example, the enrichment steps can be repeated continuously to increase the amount of non-host nucleic acids. In one aspect, the further enriched RNA population can be reverse transcribed to form a first cDNA strand; the first cDNA strand can be selectively amplified with non-host target primers to form a second enriched population of non-host nucleic acids. The second enriched population of non-host nucleic acids can undergo selective hybridization resulting in a second further enriched RNA population. The cycle of reverse transcription, selective amplification, and subtractive hybridization can be repeated indefinitely.

In some aspects, the subtractive hybridization can be performed prior to the selective amplification.

C. Methods of Detecting or Diagnosing

Disclosed are methods of detecting non-host nucleic acids in a host sample comprising selectively amplifying nucleic acids isolated from the host sample using non-host target primers to form an enriched population of non-host nucleic acids; and detecting the non-host nucleic acids by sequencing the enriched population of non-host nucleic acids.

In some instances, the host can be a human. For example, disclosed are methods of detecting non-human nucleic acids in a human sample comprising selectively amplifying nucleic acids isolated from the human sample using non-host target primers to form an enriched population of non-human nucleic acids; and detecting the non-human nucleic acids by sequencing the enriched population of non-human nucleic acids.

Non-host nucleic acids being detected can be pathogenic or non-pathogenic sequences. For example, the non-host sequences can be pathogenic sequences from viruses, bacteria, fungi or can be from any infectious agent. In some instances, the non-host sequence is unknown. For example, a human sample can be tested to determine whether a non-human nucleic acid is present in the sample. Once detected by sequencing, it can be determined whether the non-human nucleic acid is a pathogenic sequence. In some instances, the detected pathogenic sequence is unknown. A non-host nucleic acid, such as a pathogenic sequence, being unknown can mean that the pathogen sequence was not previously known, or is a new variant of a known pathogen, or is a sequence polymorphism different from host reference.

Figure 8:
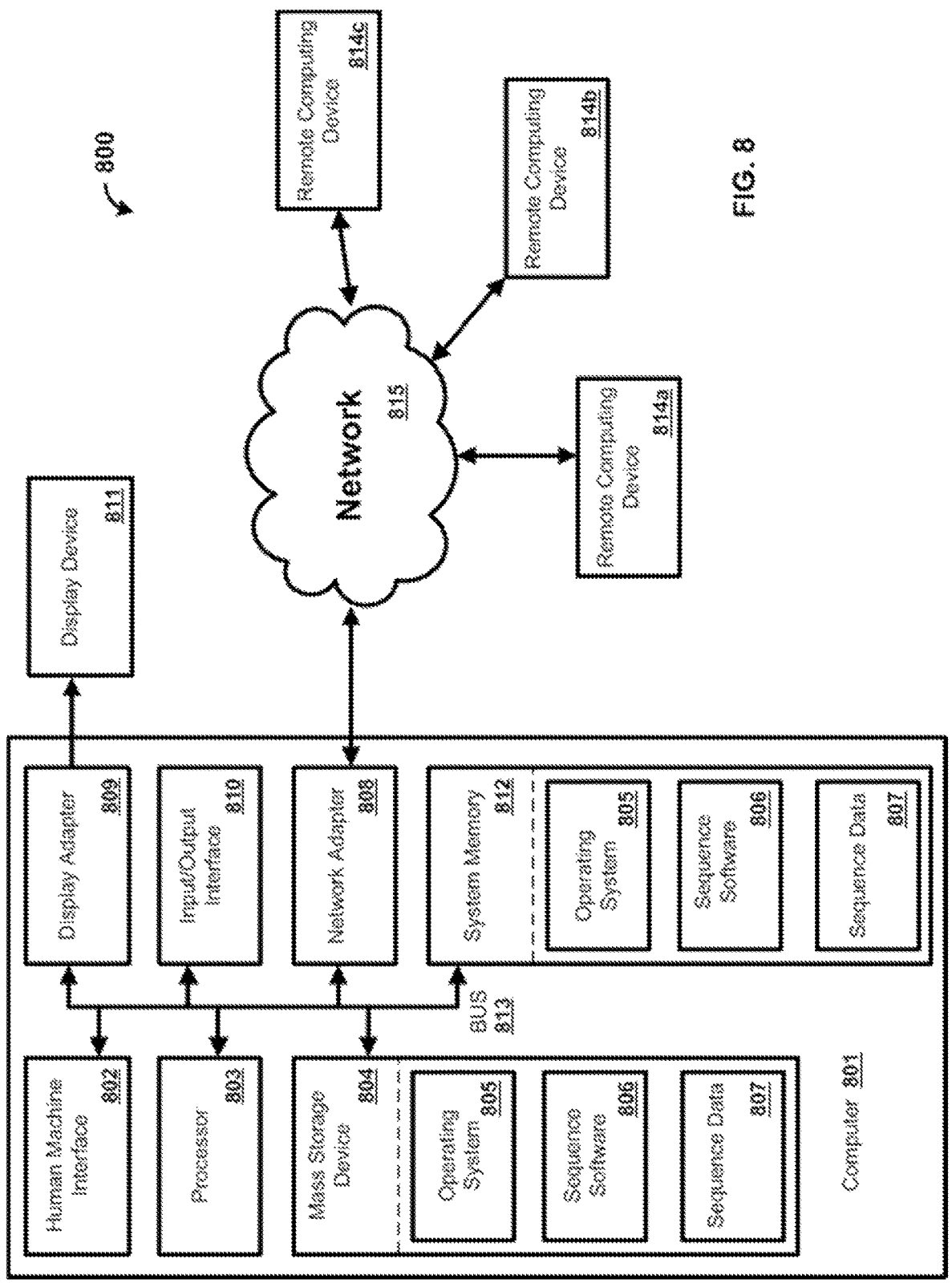
FIG. 8 is an example operating environment.

In an exemplary aspect, the methods and systems can be implemented on a computer 801 as illustrated in FIG. 8 and described below. For example, it can be determined whether the detected non-host (e.g., non-human) sequence is known. For example, it can be determined whether the non-host (e.g., non-human) sequence is a pathogenic (or other) sequence. Such a determination can be made by utilizing a computing device to compare the detected non-host (e.g., non-human) sequence to one or more other sequences (e.g., a database of known pathogenic sequences). Databases comprising full and partial sequences of known pathogens are well known in the art. For example, a program, such as BLAST, can be used to determine the percent identity of the detected non-host sequence to a known pathogen sequence. Known pathogen sequences can be found in databases similar to the ENCODE database but that are specific to the many known pathogens. For example, there is a HIV Database and a Hemorrhagic Fever Viruses Database that comprise genetic sequences of HIV and Ebola, respectively. The methods and systems disclosed can utilize one or more computers to perform one or more functions in one or more locations. FIG. 8 is a block diagram illustrating an exemplary operating environment 800 for performing the disclosed methods. This exemplary operating environment 800 is only an example of an operating environment and is not intended to suggest any limitation as to the scope of use or functionality of operating environment architecture. Neither should the operating environment 800 be interpreted as having any dependency or requirement relating to any one or combination of components illustrated in the exemplary operating environment 800.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, and/or the like that perform particular tasks or implement particular abstract data types. The disclosed methods can also be practiced in grid-based and distributed computing environments where tasks are performed by remote processing devices that are linked through a communications network. In a distributed computing environment, program modules can be located in local and/or remote computer storage media including memory storage devices.

Further, one skilled in the art will appreciate that the systems and methods disclosed herein can be implemented via a general-purpose computing device in the form of a computer 801. The computer 801 can comprise one or more components, such as one or more processors 803, a system memory 812, and a bus 813 that couples various components of the computer 801 including the one or more processors 803 to the system memory 812. In the case of multiple processors 803, the computer 801 can utilize parallel computing.

The bus 813 can comprise one or more of several possible types of bus structures, such as a memory bus, memory controller, a peripheral bus, an accelerated graphics port, and a processor or local bus using any of a variety of bus architectures. The bus 813, and all buses specified in this description can also be implemented over a wired or wireless network connection and one or more of the components of the computer 801, such as the one or more processors 803, a mass storage device 804, an operating system 805, sequence software 806, sequence data 807, a network adapter 808, a system memory 812, an Input/Output Interface 810, a display adapter 809, a display device 811, and a human machine interface 802 can be contained within one or more remote computing devices 814a,b,c at physically separate locations.

The computer 801 typically comprises a variety of computer readable media. Exemplary readable media can be any available media that is accessible by the computer 801 and comprises, for example and not meant to be limiting, both volatile and non-volatile media, removable and non-removable media. The system memory 812 can comprise computer readable media in the form of volatile memory, such as random access memory (RAM), and/or non-volatile memory, such as read only memory (ROM). The system memory 812 typically can comprise data such as sequence data 807 and/or program modules such as operating system 805 and sequence software 806 that are accessible to and/or are operated on by the one or more processors 803.

In another aspect, the computer 801 can also comprise other removable/non-removable, volatile/non-volatile computer storage media. The mass storage device 804 can provide non-volatile storage of computer code, computer readable instructions, data structures, program modules, and other data for the computer 801. For example, a mass storage device 804 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 804, including by way of example, an operating system 805 and sequence software 806. One or more of the operating system 805 and sequence software 806 (or some combination thereof) can comprise elements of the program modules and the sequence software 806. Sequence data 807 can also be stored on the mass storage device 804. Sequence data 807 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple locations within the network 815.

A user can enter commands and information into the computer 801 via an input device (not shown). Examples of such input devices comprise, but are not limited to, a keyboard, pointing device (e.g., a computer mouse, remote control), a microphone, a joystick, a scanner, tactile input devices such as gloves, and other body coverings, motion sensor, and the like These and other input devices can be connected to the one or more processors 803 via a human machine interface 802 that is coupled to the bus 813, but can be connected by other interface and bus structures, such as a parallel port, game port, an IEEE 1394 Port (also known as a Firewire port), a serial port, network adapter 808, and/or a universal serial bus (USB).

In yet another aspect, a display device 811 can also be connected to the bus 813 via an interface, such as a display adapter 809. It is contemplated that the computer 801 can have more than one display adapter 809 and the computer 801 can have more than one display device 811. For example, a display device 811 can be a monitor, an LCD (Liquid Crystal Display), light emitting diode (LED) display, television, smart lens, smart glass, and/or a projector. In addition to the display device 811, other output peripheral devices can comprise components such as speakers (not shown) and a printer (not shown) which can be connected to the computer 801 via Input/Output Interface 810. Any step and/or result of the methods can be output in any form to an output device. Such output can be any form of visual representation, including, but not limited to, textual, graphical, animation, audio, tactile, and the like. The display 811 and computer 801 can be part of one device, or separate devices.

The computer 801 can operate in a networked environment using logical connections to one or more remote computing devices 814a,b,c. By way of example, a remote computing device 814a,b,c can be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computer 801 and a remote computing device 814a,b,c can be made via a network 815, such as a local area network (LAN) and/or a general wide area network (WAN). Such network connections can be through a network adapter 808. A network adapter 808 can be implemented in both wired and wireless environments. Such networking environments are conventional and commonplace in dwellings, offices, enterprise-wide computer networks, intranets, and the Internet.

For purposes of illustration, application programs and other executable program components such as the operating system 805 are illustrated herein as discrete blocks, although it is recognized that such programs and components can reside at various times in different storage components of the computing device 801, and are executed by the one or more processors 803 of the computer 801. An implementation of sequence software 806 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ artificial intelligence (AI) techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

1. Starting from a DNA Sample

Disclosed are methods of detecting non-host nucleic acids from a host sample comprising selectively amplifying nucleic acids isolated from the host sample using non-host target primers to form an enriched population of non-host nucleic acids, wherein the nucleic acids isolated from the host sample are DNA; and detecting the non-host sequence by sequencing the enriched population of non-host nucleic acids.

Disclosed are methods of detecting non-host nucleic acids from a host sample comprising selectively amplifying nucleic acids isolated from the host sample using non-host target primers to form an enriched population of non-host nucleic acids, wherein the nucleic acids isolated from the host sample are DNA; and detecting the non-host sequence by sequencing the enriched population of non-host nucleic acids, wherein the non-host target primers are eight, nine, ten, or eleven nucleotides in length.

Disclosed are methods of detecting non-host nucleic acids from a host sample comprising selectively amplifying nucleic acids isolated from the host sample using non-host target primers to form an enriched population of non-host nucleic acids, wherein the nucleic acids isolated from the host sample are DNA; and detecting the non-host sequence by sequencing the enriched population of non-host nucleic acids, wherein the non-host target primers do not hybridize to the most abundant host transcripts. In some aspects, the most abundant host transcripts comprise at least 65% of all host transcripts. In some aspects, the most abundant host transcripts can be greater than 200 base pairs in length. In some aspects, the most abundant host transcripts can be the 1000, 2000, 3000, 4000, 5000, 6000, 7000, 8000, 9000, 10000, 20000 most abundant human transcripts or whole host transcriptome identified in the ENCODE database.

Disclosed are methods of detecting non-host nucleic acids from a host sample comprising selectively amplifying nucleic acids isolated from the host sample using non-host target primers to form an enriched population of non-host nucleic acids, wherein the nucleic acids isolated from the host sample are DNA; and detecting the non-host sequence by sequencing the enriched population of non-host nucleic acids, wherein the non-host target primers comprise one or more of the oligonucleotides in FIG. 10 or 11.

Disclosed are methods of detecting non-host nucleic acids from a host sample comprising selectively amplifying nucleic acids isolated from the host sample using non-host target primers to form an enriched population of non-host nucleic acids, wherein the nucleic acids isolated from the host sample are DNA; and detecting the non-host sequence by sequencing the enriched population of non-host nucleic acids, wherein the non-host sequences can be pathogenic sequences. In some aspects, the pathogenic sequences can be from viruses, bacteria, fungi, or any infectious agents.

In some aspects, the host can be a human. Thus, disclosed are methods of detecting non-human nucleic acids from a human sample comprising selectively amplifying nucleic acids isolated from the human sample using non-human target primers to form an enriched population of non-human nucleic acids, wherein the nucleic acids isolated from the human sample are DNA; and detecting the non-human sequence by sequencing the enriched population of non-human nucleic acids.

Disclosed are methods of detecting non-human nucleic acids from a human sample comprising selectively amplifying nucleic acids isolated from the human sample using non-human target primers to form an enriched population of non-human nucleic acids, wherein the nucleic acids isolated from the human sample are DNA; and detecting the non-human sequence by sequencing the enriched population of non-human nucleic acids, wherein the non-human target primers are eight, nine, ten, or eleven nucleotides in length.

Disclosed are methods of detecting non-human nucleic acids from a human sample comprising selectively amplifying nucleic acids isolated from the human sample using non-human target primers to form an enriched population of non-human nucleic acids, wherein the nucleic acids isolated from the human sample are DNA; and detecting the non-human sequence by sequencing the enriched population of non-human nucleic acids, wherein the non-human target primers do not hybridize to the most abundant human transcripts. In some aspects, the most abundant human transcripts comprise at least 65% of all human transcripts. In some aspects, the most abundant human transcripts can be greater than 200 base pairs in length. In some aspects, the most abundant human transcripts can be the 1000, 2000, 3000, 4000, 5000, 6000, 7000, 8000, 9000, 10000, 20000 most abundant human transcripts or whole human transcriptome identified in the ENCODE database.

Disclosed are methods of detecting non-human nucleic acids from a human sample comprising selectively amplifying nucleic acids isolated from the human sample using non-human target primers to form an enriched population of non-human nucleic acids, wherein the nucleic acids isolated from the human sample are DNA; and detecting the non-human sequence by sequencing the enriched population of non-human nucleic acids, wherein the non-human target primers comprise one or more of the oligonucleotides in FIG. 10 or 11.

Disclosed are methods of detecting non-human nucleic acids from a human sample comprising selectively amplifying nucleic acids isolated from the human sample using non-human target primers to form an enriched population of non-human nucleic acids, wherein the nucleic acids isolated from the human sample are DNA; and detecting the non-human sequence by sequencing the enriched population of non-human nucleic acids, wherein the non-human sequences can be pathogenic sequences. In some aspects, the pathogenic sequences can be from viruses, bacteria, fungi, or any infectious agents i. Isolating Methods of detecting non-host nucleic acids from a host sample can include the isolation of DNA from a host sample.

DNA isolated from a host sample can include host specific DNA as well as DNA from any non-host pathogens that may be present within the host. DNA can be isolated from a host sample and used as a template for non-host target primers. Techniques well-known in the art can be used to isolate DNA from a sample.

ii. Selectively Amplifying

Selectively amplifying DNA isolated from a host sample with non-host target primers can form an enriched population of non-host nucleic acids.

Non-host target primers can be used to selectively amplify non-host cDNA. The non-host target primers are designed to hybridize to non-host sequences and not to hybridize to host sequences. Any of the non-host target primers disclosed herein can be used. For example, when the host is human, the non-host (i.e. non-human) target primers can be one or more of the primers comprising the sequences in FIG. 10 or 11. In some aspects, the non-human target primers can be one or more sequences in Table 3.

Non-host target primers can hybridize to non-host DNA and can serve to prime synthesis of non-host DNA.

In some aspects, RNAs can be synthesized from dsDNA. Any DNA dependent RNA polymerase can be used for synthesis of RNA from dsDNA. For example, T7 RNA polymerase can be used. Other RNA polymerases such as, but not limited to, T3 and SP6 RNA polymerases can also be used.

The resulting RNAs can be RNA copies of the selectively amplified DNAs. Therefore, the RNA copies can be considered selective RNAs or an enriched RNA population. The selective RNAs comprise RNA copies of non-host DNA sequences. In some aspects, selective RNAs can be antisense RNAs.

Selective amplification results in an enriched population of non-host nucleic acids. In some aspects, the enriched population of non-host nucleic acids can comprise a DNA population that contains a higher percentage of non-host nucleic acids compared to the DNA population before selective amplification.

iii. Subtractive Hybridization

In some aspects, subtractive hybridization can be performed after the selective amplification. Thus, disclosed are methods of detecting non-host nucleic acids from a host sample comprising selectively amplifying nucleic acids isolated from the host sample using non-host target primers to form an enriched population of non-host nucleic acids, wherein the nucleic acids isolated from the host sample are DNA; and detecting the non-host sequence by sequencing the enriched population of non-host nucleic acids, further comprising performing subtractive hybridization against a population of reference host nucleic acids, wherein the subtractive hybridization results in a further enriched population of non-host nucleic acids, wherein the subtractive hybridization occurs prior to the detecting step. The reference host nucleic acids can be, but are not limited to, cDNAs.

Because the host sample can be a human sample, the disclosed methods include methods of detecting non-human nucleic acids from a human sample comprising selectively amplifying nucleic acids isolated from the human sample using non-human target primers to form an enriched population of non-human nucleic acids, wherein the nucleic acids isolated from the human sample are DNA; and detecting the non-human sequence by sequencing the enriched population of non-human nucleic acids, further comprising performing subtractive hybridization against a population of reference human nucleic acids, wherein the subtractive hybridization results in a further enriched population of non-human nucleic acids, wherein the subtractive hybridization occurs prior to the detecting step.

Performing subtractive hybridization can further enrich the enriched population of non-host nucleic acids previously enriched by selectively amplifying non-host sequences with non-host target primers.

Subtractive hybridization comprises the subtraction or removal of unwanted nucleic acids (e.g. host nucleic acids). Subtractive hybridization can comprise hybridizing the selective or enriched nucleic acids with a reference host cDNA population. Reference host cDNA populations can be created using techniques well-known in the art. In some instances, a reference host cDNA population can be one or more commercially available host cDNA libraries, such as, but not limited to, a human peripheral blood mononuclear cell (PBMC) cDNA library.

Subtractive hybridization can comprise hybridization between selective or enriched nucleic acids and a reference host cDNA population. For example, the enriched population of non-host nucleic acids can be reverse transcribed to make a selective or enriched RNA population. The selective or enriched RNA population can hybridize to the reference host cDNA population. If any of the RNAs are host RNAs, then the host RNA can hybridize to the reference host cDNA population form an RNA/DNA duplex and can be removed using RNase H. Thus, the remaining RNAs would be the selective RNAs that did not hybridize to the reference host cDNA population and therefore would be considered non-host nucleic acids. The removal of any host RNAs that were present in the selective or enriched RNA population can result in a further enriched RNA population comprising non-host RNAs.

After subtractive hybridization, the further enriched RNA population can be reverse transcribed and the methods described below can be performed or the cDNA produced from the reverse transcription can then be selectively amplified using the method described herein. For example, the enrichment steps can be repeated continuously to increase the amount of non-host nucleic acids. In one aspect, the further enriched RNA population can be reverse transcribed to form a first cDNA strand; the first cDNA strand can be selectively amplified with non-host target primers to form a second enriched population of non-host nucleic acids. The second enriched population of non-host nucleic acids can undergo selective hybridization resulting in a second further enriched RNA population. The cycle of reverse transcription, selective amplification, and subtractive hybridization can be repeated indefinitely.

iv. Detecting

Disclosed are methods of detecting a non-host sequence in a host sample comprising selectively amplifying nucleic acids isolated from the host sample using non-host target primers to form an enriched population of non-host nucleic acids, wherein the nucleic acids are DNA; and detecting the non-host sequence by sequencing the enriched population of non-host nucleic acids. In some aspects the host can be a human. As such, disclosed are methods of detecting a non-human sequence in a human sample comprising selectively amplifying nucleic acids isolated from the human sample using non-human target primers to form an enriched population of non-human nucleic acids, wherein the nucleic acids are DNA; and detecting the non-human sequence by sequencing the enriched population of non-human nucleic acids.

Detecting a non-host sequence in a host sample can comprise detecting nucleic acids obtained from the host that have been enriched for non-host sequences. Nucleic acid molecules can be detected by any method known in the art. For example sequencing, hybridization, or microarray can be used in the methods described herein. Sequencing techniques such as but not limited to Next Generation sequencing (NGS), Sanger sequencing, ensemble sequencing, capillary electrophoresis, and single molecule sequencing can be used.

Detecting the non-host sequence can be performed by sequencing the enriched population of non-human nucleic acids. Sequencing can be performed after performing one or more cycles of selective amplification or after performing selective amplification and subtractive hybridization. Also disclosed are methods of detecting a non-host sequence in a host sample comprising reverse transcribing mRNA isolated from the host sample to form first cDNA strands; selectively amplifying the first cDNA strands with non-host target primers to form an enriched population of non-host nucleic acids; and detecting the non-host sequence by sequencing the enriched population of non-host nucleic acids, further comprising performing subtractive hybridization against a reference population of host cDNAs, wherein the subtractive hybridization results in a further enriched population of cDNAs, wherein the subtractive hybridization occurs prior to the step of detecting the non-host sequence.

NGS refers to sequencing technologies having increased throughput as compared to traditional Sanger- and capillary electrophoresis-based approaches, for example with the ability to generate hundreds of thousands of relatively small sequence reads at a time. Some examples of NGS techniques include, but are not limited to, sequencing by synthesis, sequencing by ligation, sequencing by hybridization, pyrosequencing, ion semiconductor sequencing, polony sequencing, DNA nanoball sequencing, nanopore sequencing, or single molecule sequencing. NGS platforms including, but not limited to, Illumina MiSeq or HiSeq, Ion Torrent Proton, Oxford Nanopore, 454, SOLiD, and Heliscope can be used.

Besides NGS, sequencing can be performed by chain termination and gel separation, as described by Sanger et al., Proc Natl Acad Sci USA, 74(12): 5463 67 (1977). Another conventional sequencing method involves chemical degradation of nucleic acid fragments. See, Maxam et al., Proc. Natl. Acad. Sci., 74: 560 564 (1977). Finally, methods have been developed based upon sequencing by hybridization. See, e.g., Drmanac, et al. (Nature Biotech., 16: 54 58, 1998). The contents of each of reference is incorporated by reference herein in its entirety for their teaching of sequencing processes.

In some aspects, sequencing can be performed by the Sanger sequencing technique. Classical Sanger sequencing involves a single-stranded DNA template, a DNA primer, a DNA polymerase, radioactively or fluorescently labeled nucleotides, and modified nucleotides that terminate DNA strand elongation. If the label is not attached to the dideoxynucleotide terminator (e.g., labeled primer), or is a monochromatic label (e.g., radioisotope), then the DNA sample is divided into four separate sequencing reactions, containing four standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'-OH group required for the formation of a phosphodiester bond between two nucleotides during DNA strand elongation. If each of the dideoxynucleotides carries a different label, however, (e.g., 4 different fluorescent dyes), then all the sequencing reactions can be carried out together without the need for separate reactions. Sanger sequencing is well-known in the art.

Sequencing can also be accomplished by a single-molecule sequencing by synthesis technique. Single molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety. Briefly, a single-stranded nucleic acid (e.g., DNA or cDNA) is hybridized to oligonucleotides attached to a surface of a flow cell. The oligonucleotides may be covalently attached to the surface or various attachments other than covalent linking as known to those of ordinary skill in the art may be employed. Moreover, the attachment may be indirect, e.g., via a polymerase directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

v. Diagnosing

The methods described herein can also be used for diagnosing infectious disease. In some aspects, after detecting a pathogenic sequence in a host sample, the host can be diagnosed as having an infectious disease related to the pathogenic sequence. For example, if a pathogenic sequence from an influenza virus is detected in a host sample, then the host can be diagnosed with having an influenza virus infection.

Thus disclosed are methods of diagnosing infectious disease in a host comprising selectively amplifying nucleic acids isolated from the host sample using non-host target primers to form an enriched population of non-host nucleic acids, wherein the nucleic acids are DNA; detecting a non-host sequence by sequencing the enriched population of non-host nucleic acids; and diagnosing the host with an infectious disease when the non-host sequence is a pathogenic sequence.

2. Starting from a RNA Sample i. Selective Reverse Transcription

Disclosed are methods of detecting non-host nucleic acids from a host sample comprising selectively reverse transcribing total or mRNA isolated from the host sample to form first cDNA strands using non-host target primers, wherein the first cDNA strands form an enriched population of non-host nucleic acids; and detecting the non-host sequence by sequencing the enriched population of non-host nucleic acids.

Disclosed are methods of detecting non-host nucleic acids from a host sample comprising selectively reverse transcribing total or mRNA isolated from the host sample to form first cDNA strands using non-host target primers, wherein the first cDNA strands form an enriched population of non-host nucleic acids; and detecting the non-host sequence by sequencing the enriched population of non-host nucleic acids, wherein the non-host target primers are eight, nine, ten, or eleven nucleotides in length.

Disclosed are methods of detecting non-host nucleic acids from a host sample comprising selectively reverse transcribing total or mRNA isolated from the host sample to form first cDNA strands using non-host target primers, wherein the first cDNA strands form an enriched population of non-host nucleic acids; and detecting the non-host sequence by sequencing the enriched population of non-host nucleic acids, wherein the non-host target primers do not hybridize to the most abundant host transcripts. In some aspects, the most abundant host transcripts comprise at least 65% of all host transcripts. In some aspects, the most abundant host transcripts can be greater than 200 base pairs in length. In some aspects, the most abundant host transcripts can be the 1000, 2000, 3000, 4000, 5000, 6000, 7000, 8000, 9000, 10000, 20000 most abundant human transcripts or whole host transcriptome identified in the ENCODE database.

Disclosed are methods of detecting non-host nucleic acids from a host sample comprising selectively reverse transcribing total or mRNA isolated from the host sample to form first cDNA strands using non-host target primers, wherein the first cDNA strands form an enriched population of non-host nucleic acids; and detecting the non-host sequence by sequencing the enriched population of non-host nucleic acids, wherein the non-host target primers comprise the complement of one or more of the oligonucleotides in Table 5-8.

Disclosed are methods of detecting non-host nucleic acids from a host sample comprising selectively reverse transcribing total or mRNA isolated from the host sample to form first cDNA strands using non-host target primers, wherein the first cDNA strands form an enriched population of non-host nucleic acids; and detecting the non-host sequence by sequencing the enriched population of non-host nucleic acids, wherein the non-host sequences can be pathogenic sequences. In some aspects, the pathogenic sequences can be from viruses, bacteria, fungi, or any infectious agents.

In some aspects the host can be a human. Thus, disclosed are methods of detecting non-human nucleic acids from a human sample comprising selectively reverse transcribing total or mRNA isolated from the human sample to form first cDNA strands using non-human target primers, wherein the first cDNA strands form an enriched population of non-human nucleic acids; and detecting the non-human sequence by sequencing the enriched population of non-human nucleic acids.

Disclosed are methods of detecting non-human nucleic acids from a human sample comprising selectively reverse transcribing total or mRNA isolated from the human sample to form first cDNA strands using non-human target primers, wherein the first cDNA strands form an enriched population of non-human nucleic acids; and detecting the non-human sequence by sequencing the enriched population of non-human nucleic acids, wherein the non-human target primers are eight, nine, ten, or eleven nucleotides in length.

Disclosed are methods of detecting non-human nucleic acids from a human sample comprising selectively reverse transcribing total or mRNA isolated from the human sample to form first cDNA strands using non-human target primers, wherein the first cDNA strands form an enriched population of non-human nucleic acids; and detecting the non-human sequence by sequencing the enriched population of non-human nucleic acids, wherein the non-human target primers do not hybridize to the most abundant human transcripts. In some aspects, the most abundant human transcripts comprise at least 65% of all human transcripts. In some aspects, the most abundant human transcripts can be greater than 200 base pairs in length. In some aspects, the most abundant human transcripts can be the 1000, 2000, 3000, 4000, 5000, 6000, 7000, 8000, 9000, 10000, 20000 most abundant human transcripts or whole human transcriptome identified in the ENCODE database.

Disclosed are methods of detecting non-human nucleic acids from a human sample comprising selectively reverse transcribing total or mRNA isolated from the human sample to form first cDNA strands using non-human target primers, wherein the first cDNA strands form an enriched population of non-human nucleic acids; and detecting the non-human sequence by sequencing the enriched population of non-human nucleic acids, wherein the non-human target primers comprise one or more of the oligonucleotides in Table 5-8.

Disclosed are methods of detecting non-human nucleic acids from a human sample comprising selectively reverse transcribing total or mRNA isolated from the human sample to form first cDNA strands using non-human target primers, wherein the first cDNA strands form an enriched population of non-human nucleic acids; and detecting the non-human sequence by sequencing the enriched population of non-human nucleic acids, wherein the non-human sequences can be pathogenic sequences. In some aspects, the pathogenic sequences can be from viruses, bacteria, fungi, or any infectious agents.

a. Isolating

Methods of detecting non-host nucleic acids from a host sample can include the isolation of total RNA or mRNA from a host sample. Total RNA or mRNA can be isolated from a host sample and used as a template for creating first cDNA strands. Techniques well-known in the art can be used to isolate total RNA or mRNA from a sample.

b. Reverse Transcribing and Selective Amplification Combined

Non-host target primers can be used to selectively amplify total RNA or mRNA. The non-host target primers are designed to hybridize non-host sequences and not to hybridize to host sequences. The complement of any of the non-host target primers disclosed herein can be used. For example, when the host is human, the non-host (i.e. non-human) target primers can be one or more of the primers comprising the complement of the sequences FIG. 10 or 11. In some aspects, the non-human target primers can be one or more of the complement of the sequences in Table 3.

Non-host target primers can hybridize to non-host total RNA or mRNA and can serve to prime synthesis of non-host cDNA strands.

The combination of reverse transcription and selective amplification can also be known as selective reverse transcription.

c. Subtractive Hybridization

In some aspects, a further step of subtractive hybridization can be performed.

Thus, disclosed are methods of detecting non-host nucleic acids from a host sample comprising selectively reverse transcribing total or mRNA isolated from the host sample to form first cDNA strands using non-host target primers, wherein the first cDNA strands form an enriched population of non-host nucleic acids; and detecting the non-host sequence by sequencing the enriched population of non-host nucleic acids, further comprising performing subtractive hybridization against a population of reference host cDNAs, wherein the subtractive hybridization results in a further enriched population of non-host nucleic acids, wherein the subtractive hybridization occurs prior to the detecting step.

Because the host sample can be a human sample, the disclosed methods include methods of detecting non-human nucleic acids from a human sample comprising selectively reverse transcribing total or mRNA isolated from the human sample to form first cDNA strands using non-human target primers, wherein the first cDNA strands form an enriched population of non-human nucleic acids; and detecting the non-human sequence by sequencing the enriched population of non-human nucleic acids, further comprising performing subtractive hybridization against a population of reference human cDNAs, wherein the subtractive hybridization results in a further enriched population of non-human cDNAs, wherein the subtractive hybridization occurs prior to the detecting step.

Performing subtractive hybridization can further enrich the enriched population of non-host nucleic acids previously enriched by selectively reverse transcribing non-host sequences with non-host target primers.

Subtractive hybridization comprises the subtraction or removal of unwanted nucleic acids (e.g. host nucleic acids). Subtractive hybridization can comprise hybridizing the selective or enriched RNAs with a reference host cDNA population. Reference host cDNA populations can be created using techniques well-known in the art. In some instances, a reference host cDNA population can be one or more commercially available host cDNA libraries, such as, but not limited to, a human peripheral blood mononuclear cell (PBMC) cDNA library.

The enriched population of non-host nucleic acids can be reverse transcribed to form an enriched or selective population of RNA. Subtractive hybridization can comprise hybridization between selective or enriched RNA and a reference host cDNA population. Any host RNAs present in the selective RNAs can hybridize to the reference host cDNA population. Host RNAs hybridized to the reference host cDNA population form an RNA/DNA duplex and can be removed using RNase H. Thus, the remaining RNAs would be the selective RNAs that did not hybridize to the reference host cDNA population and therefore would be considered non-host nucleic acids. The removal of any host RNAs that were present in the selective or enriched RNA population can result in a further enriched RNA population comprising non-host RNAs.

After subtractive hybridization, the further enriched RNA population can be treated as the original RNA obtained from the sample and the further enriched RNA population can be used to repeat one or more of the steps described above. For example, the enrichment steps can be repeated continuously to increase the amount of non-host nucleic acids. In one aspect, the further enriched RNA population can be selectively reverse transcribed using non-host target primers to form a second enriched population of non-host nucleic acids. The cycle of selective reverse transcription and subtractive hybridization can be repeated indefinitely.

d. Detecting

Disclosed are methods of detecting a non-host sequence in a host sample comprising selectively reverse transcribing total or mRNA isolated from the host sample to form first cDNA strands using non-host target primers, wherein the first cDNA strands form an enriched population of non-host nucleic acids; and detecting the non-host sequence by sequencing the enriched population of non-host nucleic acids. In some aspects the host can be a human. As such, disclosed are methods of detecting a non-human sequence in a human sample comprising selectively reverse transcribing total or mRNA isolated from the host sample to form first cDNA strands using non-host target primers, wherein the first cDNA strands form an enriched population of non-host nucleic acids; and detecting the non-host sequence by sequencing the enriched population of non-host nucleic acids.

Detecting a non-host sequence in a host sample can comprise detecting nucleic acids obtained from the host that have been enriched for non-host sequences. Nucleic acid molecules can be detected by any method known in the art. For example sequencing, hybridization, or microarray can be used in the methods described herein. Sequencing techniques such as but not limited to Next Generation sequencing (NGS), Sanger sequencing, ensemble sequencing, capillary electrophoresis, and single molecule sequencing can be used.

Detecting the non-host sequence can be performed by sequencing the enriched population of non-human nucleic acids. Sequencing can be performed after performing one or more cycles of selective amplification or after performing selective amplification and subtractive hybridization. Also disclosed are methods of detecting a non-host sequence in a host sample comprising reverse transcribing mRNA isolated from the host sample to form first cDNA strands; selectively amplifying the first cDNA strands with non-host target primers to form an enriched population of non-host nucleic acids; and detecting the non-host sequence by sequencing the enriched population of non-host nucleic acids, further comprising performing subtractive hybridization against a reference population of host cDNAs, wherein the subtractive hybridization results in a further enriched population of cDNAs, wherein the subtractive hybridization occurs prior to the step of detecting the non-host sequence.

NGS refers to sequencing technologies having increased throughput as compared to traditional Sanger- and capillary electrophoresis-based approaches, for example with the ability to generate hundreds of thousands of relatively small sequence reads at a time. Some examples of NGS techniques include, but are not limited to, sequencing by synthesis, sequencing by ligation, sequencing by hybridization, pyrosequencing, ion semiconductor sequencing, polony sequencing, DNA nanoball sequencing, nanopore sequencing, or single molecule sequencing. NGS platforms including, but not limited to, Illumina MiSeq or HiSeq, Ion Torrent Proton, Oxford Nanopore, 454, SOLiD, and Heliscope can be used.

Besides NGS, sequencing can be performed by chain termination and gel separation, as described by Sanger et al., Proc Natl Acad Sci USA, 74(12): 5463 67 (1977). Another conventional sequencing method involves chemical degradation of nucleic acid fragments. See, Maxam et al., Proc. Natl. Acad. Sci., 74: 560 564 (1977). Finally, methods have been developed based upon sequencing by hybridization. See, e.g., Drmanac, et al. (Nature Biotech., 16: 54 58, 1998). The contents of each of reference is incorporated by reference herein in its entirety for their teaching of sequencing processes.

In some aspects, sequencing can be performed by the Sanger sequencing technique. Classical Sanger sequencing involves a single-stranded DNA template, a DNA primer, a DNA polymerase, radioactively or fluorescently labeled nucleotides, and modified nucleotides that terminate DNA strand elongation. If the label is not attached to the dideoxynucleotide terminator (e.g., labeled primer), or is a monochromatic label (e.g., radioisotope), then the DNA sample is divided into four separate sequencing reactions, containing four standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'-OH group required for the formation of a phosphodiester bond between two nucleotides during DNA strand elongation. If each of the dideoxynucleotides carries a different label, however, (e.g., 4 different fluorescent dyes), then all the sequencing reactions can be carried out together without the need for separate reactions. Sanger sequencing is well-known in the art.

Sequencing can also be accomplished by a single-molecule sequencing by synthesis technique. Single molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety. Briefly, a single-stranded nucleic acid (e.g., DNA or cDNA) is hybridized to oligonucleotides attached to a surface of a flow cell. The oligonucleotides may be covalently attached to the surface or various attachments other than covalent linking as known to those of ordinary skill in the art may be employed. Moreover, the attachment may be indirect, e.g., via a polymerase directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

e. Diagnosing

The methods described herein can also be used for diagnosing infectious disease. In some aspects, after detecting a pathogenic sequence in a host sample, the host can be diagnosed as having an infectious disease related to the pathogenic sequence. For example, if a pathogenic sequence from an influenza virus is detected in a host sample, then the host can be diagnosed with having an influenza virus infection.

Thus disclosed are methods of diagnosing infectious disease in a host comprising selectively amplifying nucleic acids isolated from the host sample using non-host target primers to form an enriched population of non-host nucleic acids, wherein the nucleic acids are DNA; detecting a non-host sequence by sequencing the enriched population of non-host nucleic acids; and diagnosing the host with an infectious disease when the non-host sequence is a pathogenic sequence.

ii. Reverse Transcription and then Selective Amplification

Disclosed are methods of detecting non-host nucleic acids from a host sample comprising reverse transcribing total RNA or mRNA obtained from the host sample to form first cDNA strands; selectively amplifying the first cDNA strands with non-host target primers to form an enriched population of non-host nucleic acids; and detecting the non-host sequence by sequencing the enriched population of non-host nucleic acids.

Disclosed are methods of detecting non-host nucleic acids from a host sample comprising reverse transcribing total RNA or mRNA obtained from the host sample to form first cDNA strands; selectively amplifying the first cDNA strands with non-host target primers to form an enriched population of non-host nucleic acids; and detecting the non-host sequence by sequencing the enriched population of non-host nucleic acids, wherein the non-host target primers are eight, nine, ten, or eleven nucleotides in length.

Disclosed are methods of detecting non-host nucleic acids from a host sample comprising reverse transcribing total RNA or mRNA obtained from the host sample to form first cDNA strands; selectively amplifying the first cDNA strands with non-host target primers to form an enriched population of non-host nucleic acids; and detecting the non-host sequence by sequencing the enriched population of non-host nucleic acids, wherein the non-host target primers do not hybridize to the most abundant host transcripts. In some aspects, the most abundant host transcripts comprise at least 65% of all host transcripts. In some aspects, the most abundant host transcripts can be greater than 200 base pairs in length. In some aspects, the most abundant host transcripts can be the 1000, 2000, 3000, 4000, 5000, 6000, 7000, 8000, 9000, 10000, 20000 most abundant human transcripts or whole host transcriptome identified in the ENCODE database.

Disclosed are methods of detecting non-host nucleic acids from a host sample comprising reverse transcribing total RNA or mRNA obtained from the host sample to form first cDNA strands; selectively amplifying the first cDNA strands with non-host target primers to form an enriched population of non-host nucleic acids; and detecting the non-host sequence by sequencing the enriched population of non-host nucleic acids, wherein the non-host target primers comprise one or more of the oligonucleotides in FIG. 10 or 11.

Disclosed are methods of detecting non-host nucleic acids from a host sample comprising reverse transcribing total RNA or mRNA obtained from the host sample to form first cDNA strands; selectively amplifying the first cDNA strands with non-host target primers to form an enriched population of non-host nucleic acids; and detecting the non-host sequence by sequencing the enriched population of non-host nucleic acids, wherein the non-host sequences can be pathogenic sequences. In some aspects, the pathogenic sequences can be from viruses, bacteria, fungi, or any infectious agents.

In some aspects, the host can be a human. Thus, also disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids; and detecting the non-human sequence by sequencing the enriched population of non-human nucleic acids.

Disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids; and detecting the non-human sequence by sequencing the enriched population of non-human nucleic acids, wherein the non-human target primers are eight, nine, ten, or eleven nucleotides in length.

Disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids; and detecting the non-human sequence by sequencing the enriched population of non-human nucleic acids, wherein the non-human target primers do not hybridize to the most abundant human transcripts. In some aspects, the most abundant human transcripts comprise at least 65% of all human transcripts. In some aspects, the most abundant human transcripts can be greater than 200 base pairs in length. In some aspects, the most abundant human transcripts can be the 1000, 2000, 3000, 4000, 5000, 6000, 7000, 8000, 9000, 10000, 20000 most abundant human transcripts or whole human transcriptome identified in the ENCODE database.

Disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids; and detecting the non-human sequence by sequencing the enriched population of non-human nucleic acids, wherein the non-human target primers comprise one or more of the oligonucleotides in FIG. 10 or 11.

Disclosed are methods of enriching non-human nucleic acids from a human sample comprising reverse transcribing total RNA or mRNA obtained from the human sample to form first cDNA strands; and selectively amplifying the first cDNA strands with non-human target primers to form an enriched population of non-human nucleic acids; and detecting the non-human sequence by sequencing the enriched population of non-human nucleic acids, wherein the non-human sequences can be pathogenic sequences. In some aspects, the pathogenic sequences can be from viruses, bacteria, fungi, or any infectious agents.

a. Isolating

Methods of detecting a non-host sequence in a host sample can include the isolation of total RNA or mRNA from a host sample. Total RNA or mRNA can be isolated from a host sample and used as a template for creating cDNA. Techniques well-known in the art can be used to isolate total RNA or mRNA from a sample.

b. Reverse Transcribing

Isolated total RNA or mRNA obtained from a host sample can be used as the template for creating a first cDNA strand for each of the isolated total RNA or mRNAs. Methods for reverse transcribing mRNA are well-known in the art. For example, a poly d(T) primer in combination with reverse transcriptase can be used to produce a first cDNA strand from mRNA.

Reverse transcriptases have RNA dependent DNA polymerase activity and thus can produce a cDNA strand from an RNA template. In some instances, reverse transcriptases can further comprise RNase H activity, which results in the cleavage of RNA from an RNA-DNA duplex. In some instances, RNase H can be added separately from the reverse transcriptase.

Several types of primers can be used during reverse transcription. For example, the primers can be but are not limited to random primers, sequence specific primers, and/or poly d(T) primers. When reverse transcribing total RNA, random primers and poly d(T) primers are often used since the sequences of the RNA may not be known.

In some aspects, the primers can be poly d(T) primers further comprising an RNA polymerase promoter sequence. Thus, a poly d(T)-RNA polymerase promoter primer can be used to form first cDNA strands from a host sample comprising reverse transcribing mRNA obtained from the host sample. In some aspects, the poly d(T)-RNA polymerase promoter primer can comprise poly d(T)-T7 promoter sequences as shown in FIG. 2. Promoter sequences for other RNA polymerases such as, but not limited to, T3 and SP6 RNA polymerases can also be used.

c. Selectively Amplifying

When reverse transcription is performed without the combination of selective amplification, the step of selective amplification is performed on the first cDNA strands produced from reverse transcription.

The first cDNA strands produced from reverse transcribing mRNA obtained from a host sample can be used for selective amplification. Selectively amplifying the first cDNA strands with non-host target primers can form an enriched population of non-host nucleic acids.

Before selectively amplifying the first cDNA strands, the mRNA that served as the template for the first cDNA strand can be removed. Removal of the mRNA can be performed by adding RNase H before selective amplification. In some instances, the RNA Dependent DNA polymerase used to produce the first cDNA strand can have RNase H activity. In some instances, RNase H can be added as a separate enzyme independent of the DNA polymerase. After removing the mRNA, or after selectively isolating the first cDNA strands, only first cDNA strands remain.

Non-host target primers can be used to selectively amplify non-host cDNA. The non-host target primers are designed to hybridize non-host sequences and not to hybridize to host sequences. Any of the non-host target primers disclosed herein can be used. For example, when the host is human, the non-host (i.e. non-human) target primers can be one or more of the primers comprising the sequences in FIG. 10 or 11. In some aspects, the non-human target primers can be one or more of the sequences in Table 3.

Non-host target primers can hybridize to non-host first cDNA strands and can serve to prime synthesis of second non-host cDNA strand.

RNAs can also be synthesized from dsDNA. For example, RNA can be synthesized from dsDNA comprising non-host first cDNA strand and non-host second cDNA strands. Any DNA dependent RNA polymerase can be used for synthesis of RNA from dsDNA. For example, T7 RNA polymerase can be used. Other RNA polymerases such as, but not limited to, T3 and SP6 RNA polymerases can also be used.

The resulting RNAs can be RNA copies of the selectively amplified cDNAs. Therefore, the RNA copies can be considered selective RNAs or an enriched RNA population. The selective RNAs comprise RNA copies of non-host cDNA sequences. In some aspects, selective RNAs can be antisense RNAs.

Selective amplification can result in an enriched population of non-host nucleic acids. In some aspects, the enriched population of non-host nucleic acids can comprise a cDNA population that contains a higher percentage of non-host nucleic acids compared to the cDNA population before selective amplification. In some aspects, the enriched population of non-host nucleic acids can comprise a population of RNAs that contains a higher percentage of non-host RNA sequences compared to the mRNA obtained from the host sample.

d. Subtractive Hybridization

In some aspects, subtractive hybridization can be performed when detecting non-host nucleic acids in a host sample.

Disclosed are methods of detecting non-host nucleic acids in a host sample comprising reverse transcribing total RNA or mRNA isolated from the host sample to form first cDNA strands; selectively amplifying the first cDNA strands with non-host target primers to form an enriched population of non-host nucleic acids; and detecting the non-host nucleic acids by sequencing the enriched population of non-host nucleic acids, further comprising performing subtractive hybridization against a reference population of host cDNAs, wherein the subtractive hybridization results in a further enriched population of cDNAs, wherein the subtractive hybridization occurs prior to the detecting step.

Because the host sample can be a human sample, the disclosed methods include methods of detecting a non-human sequence in a human sample comprising reverse transcribing total RNA or mRNA isolated from the human sample to form first cDNA strands; selectively amplifying the first cDNA strands with non-human target primers to form an enriched population of non-human nucleic acids; and detecting the non-human nucleic acids by sequencing the enriched population of non-human nucleic acids, further comprising performing subtractive hybridization against a reference population of human cDNAs, wherein the subtractive hybridization results in a further enriched population of cDNAs, wherein the subtractive hybridization occurs prior to detecting the pathogenic sequence.

Performing subtractive hybridization can further enrich the enriched population of non-host nucleic acids previously enriched by selectively amplifying non-host sequences with non-host target primers.

Subtractive hybridization can comprise the subtraction or removal of unwanted nucleic acids (e.g. host nucleic acids). Subtractive hybridization can comprise hybridizing the selective or enriched RNAs with a reference host cDNA population. Reference host cDNA populations can be created using techniques well-known in the art. In some instances, a reference host cDNA population can be one or more commercially available host cDNA libraries, such as, but not limited to, human peripheral blood mononuclear cell (PBMC) cDNA library.

Subtractive hybridization can comprise hybridization between selective or enriched RNA and a reference host cDNA population. Any host RNAs present in the selective RNAs can bind to the reference host cDNA population. Host RNAs hybridized to the reference host cDNA population form an RNA/DNA duplex and can be removed using RNase H. Thus, the remaining RNAs would be the selective RNAs that did not hybridize to the reference host cDNA population and therefore would be considered non-host nucleic acids. The removal of any host RNAs that were present in the selective or enriched RNA population can result in a further enriched RNA population comprising non-host RNAs.

After subtractive hybridization, the further enriched RNA population can be treated as the original RNA obtained from the sample and the further enriched RNA population can be used to repeat one or more of the steps described above. For example, the enrichment steps can be repeated continuously to increase the amount of non-host nucleic acids. In one aspect, the further enriched RNA population can be reverse transcribed to form a first cDNA strand; the first cDNA strand can be selectively amplified with non-host target primers to form a second enriched population of non-host nucleic acids. The second enriched population of non-host nucleic acids can undergo selective hybridization resulting in a second further enriched RNA population. The cycle of reverse transcription, selective amplification, and subtractive hybridization can be repeated indefinitely. The first cDNA strand can be reverse transcribed using a poly d(T)-T7 promoter primer listed in FIG. 2.

e. Detecting

Disclosed are methods of detecting a non-host sequence in a host sample comprising reverse transcribing total RNA or mRNA obtained from the host sample to form first cDNA strands; selectively amplifying the first cDNA strands with non-host target primers to form an enriched population of non-host nucleic acids; and detecting the non-host sequence by sequencing the enriched population of non-host nucleic acids. In some aspects the host can be a human. As such, disclosed are methods of detecting a non-human sequence in a human sample comprising reverse transcribing total RNA or mRNA obtained from the human sample to form first cDNA strands; selectively amplifying the first cDNA strands with non-human target primers to form an enriched population of non-human nucleic acids; and detecting the non-human sequence by sequencing the enriched population of non-human nucleic acids.

Detecting a non-host sequence in a host sample can comprise detecting nucleic acids obtained from the host that have been enriched for non-host sequences. Nucleic acid molecules can be detected by any method known in the art. For example sequencing, hybridization, or microarray can be used in the methods described herein. Sequencing techniques such as but not limited to Next Generation sequencing (NGS), Sanger sequencing, ensemble sequencing, capillary electrophoresis, and single molecule sequencing can be used.

Detecting the non-host sequence can be performed by sequencing the enriched population of non-human nucleic acids. Sequencing can be performed after performing one or more cycles of selective amplification or after performing selective amplification and subtractive hybridization. Also disclosed are methods of detecting a non-host sequence in a host sample comprising reverse transcribing mRNA isolated from the host sample to form first cDNA strands; selectively amplifying the first cDNA strands with non-host target primers to form an enriched population of non-host nucleic acids; and detecting the non-host sequence by sequencing the enriched population of non-host nucleic acids, further comprising performing subtractive hybridization against a reference population of host cDNAs, wherein the subtractive hybridization results in a further enriched population of cDNAs, wherein the subtractive hybridization occurs prior to the step of detecting the non-host sequence.

NGS refers to sequencing technologies having increased throughput as compared to traditional Sanger- and capillary electrophoresis-based approaches, for example with the ability to generate hundreds of thousands of relatively small sequence reads at a time. Some examples of NGS techniques include, but are not limited to, sequencing by synthesis, sequencing by ligation, sequencing by hybridization, pyrosequencing, ion semiconductor sequencing, polony sequencing, DNA nanoball sequencing, nanopore sequencing, or single molecule sequencing. NGS platforms including, but not limited to, Illumina MiSeq or HiSeq, Ion Torrent Proton, Oxford Nanopore, 454, SOLiD, and Heliscope can be used.

Besides NGS, sequencing can be performed by chain termination and gel separation, as described by Sanger et al., Proc Natl Acad Sci USA, 74(12): 5463 67 (1977). Another conventional sequencing method involves chemical degradation of nucleic acid fragments. See, Maxam et al., Proc. Natl. Acad. Sci., 74: 560 564 (1977). Finally, methods have been developed based upon sequencing by hybridization. See, e.g., Drmanac, et al. (Nature Biotech., 16: 54 58, 1998). The contents of each of reference is incorporated by reference herein in its entirety for their teaching of sequencing processes.

In some aspects, sequencing can be performed by the Sanger sequencing technique. Classical Sanger sequencing involves a single-stranded DNA template, a DNA primer, a DNA polymerase, radioactively or fluorescently labeled nucleotides, and modified nucleotides that terminate DNA strand elongation. If the label is not attached to the dideoxynucleotide terminator (e.g., labeled primer), or is a monochromatic label (e.g., radioisotope), then the DNA sample is divided into four separate sequencing reactions, containing four standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'-OH group required for the formation of a phosphodiester bond between two nucleotides during DNA strand elongation. If each of the dideoxynucleotides carries a different label, however, (e.g., 4 different fluorescent dyes), then all the sequencing reactions can be carried out together without the need for separate reactions. Sanger sequencing is well-known in the art.

Sequencing can also be accomplished by a single-molecule sequencing by synthesis technique. Single molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety. Briefly, a single-stranded nucleic acid (e.g., DNA or cDNA) is hybridized to oligonucleotides attached to a surface of a flow cell. The oligonucleotides may be covalently attached to the surface or various attachments other than covalent linking as known to those of ordinary skill in the art may be employed. Moreover, the attachment may be indirect, e.g., via a polymerase directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

f. Diagnosing

The methods described herein can also be used for diagnosing infectious disease. In some aspects, after detecting a pathogenic sequence in a host sample, the host can be diagnosed as having an infectious disease related to the pathogenic sequence. For example, if a pathogenic sequence from an influenza virus is detected in a host sample, then the host can be diagnosed with having an influenza virus infection.

Thus disclosed are methods of diagnosing infectious disease in a host comprising reverse transcribing mRNA isolated from a sample obtained from the host to form first cDNA strands; selectively amplifying the first cDNA strands with non-host target primers to form an enriched population of non-host nucleic acids; detecting a non-host sequence by sequencing the enriched population of non-host nucleic acids; and diagnosing the host with an infectious disease when the non-host sequence is a pathogenic sequence.

D. Non-Host Target Primers

Disclosed herein are non-host target primers that can be used in any of the disclosed methods. Non-host target primers are primers that do not hybridize (i.e. are not complementary) to any host transcripts or to the most abundant host transcripts. Non-host target primers are designed to target a sequence other than host nucleic acid sequences. Non-host target primers can hybridize to non-host sequences present in a host sample. Because the non-host sequences present within a host sample may not be known, the non-host target primers are not necessarily specific to non-host sequences; however they are specifically designed not to hybridize to host sequences or not to hybridize to the most abundant host transcripts. Thus, the non-host target primers can be considered random although they are not completely random because they are specifically designed not to hybridize to the most abundant transcripts of the host.

Non-host target primers can range in size depending on what the host is and depending on what the non-host is. Because the non-host target primers are designed not to bind to host nucleic acid sequences, the non-host target primers are dependent on the sequence of the host nucleic acids. For example, if the host is human then the non-host target primers are considered non-human target primers and are dependent on human nucleic acid sequences. Based on the human nucleic sequences, the non-human target primers can be designed so that they do not hybridize to the known human sequences. Non-human target primers can be eight, nine, ten or eleven nucleotides in length. When the host is not human, the non-host target primers can be at least 5, 6, 7, 8, 9, 10, 15, 20, 25, or 30 nucleotides in length.

The length of the non-host target primer is based on its ability to exclude the majority of host transcripts while retaining the ability to hybridize to non-host sequences. For example the likelihood of finding a match for a 9-mer oligo in a random sequence is $4^9 \times 9 = 2,359,296$, which is larger than the genome size of many human pathogens. That means, this 9-mer oligo, although it can get rid of all human transcripts, is less likely to pick up (amplify) all potential pathogen sequences.

Non-host target primers can be designed so that they do not hybridize to the most abundant host transcripts. The most abundant host transcripts can be those transcripts that comprise at least 60%, 65%, 70%, 75%, 80%, 85%, 90%, 95, 96%, 97%, 98%, 99% or 100% of all host transcripts. The most abundant transcripts can vary depending on the host. Knowing the host transcriptome data can help design non-host target primers. For example, the human transcriptome data obtained from the Encyclopedia of DNA Elements (ENCODE) was used to identify the most abundant human transcripts. The most abundant human transcripts can be those transcripts that comprise at least 60%, 65%, 70%, 75%, 80%, 85%, 90%, 95, 96%, 97%, 98%, 99% or 100% of all human transcripts. Other species' transcriptomes can be accessed from public databases for other species including, but not limited to, dog, cattle, sheep, swine, chicken, sea urchin, yeast, Arabidopsis, honey bee, etc.

The most abundant host transcripts, can be considered those transcripts having greater than 100, 150, 200, 250, 300, 350, 400, 450, 500, 1000, 2000, 3000, 4000, 5000, 6000, 7000, 8000, 9000, or 10000 base pairs in length. For example, when the host is human, the most abundant human transcripts can be greater than 200 base pairs in length. The most abundant host transcripts can be the 10, 20, 30, 40, 50, 60, 70, 80, 90, 100, 250, 500, 1000, 2000, 3000, 4000, 5000, 6000, 7000, 8000, 9000, 10000, 12000, 14000, 16000, 18000 or 20000 most abundant host transcripts known in that host. For example, the most abundant human transcripts can be the 1000, 2000, 3000, 4000, 5000, 6000, 7000, 8000, 9000, 10000, 20000 most abundant human transcripts or all human transcripts identified in the ENCODE database.

Non-host target primers can be non-human target primers. Non-human target primers can comprise one or more of the oligonucleotides of Tables 3 or FIG. 10 or 11.

Disclosed are compositions comprising at least two of the non-human oligonucleotides listed in Tables 3 or FIG. 10 or 11.

In some aspects, compositions comprise at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 of the oligonucleotides listed in Tables 3 or FIG. 10 or 11. In some aspects, compositions comprise up to 150, 200, 250, 300, 350, 400, 450, 500, 1000, 2000, 3000, 4000, or 5000 of the oligonucleotides listed in Tables 3, or FIG. 10 or 11.

Also disclosed are compositions comprising at least two of the complement of the non-human oligonucleotides listed in Tables 3 or FIG. 10 or 11.

In some aspects, compositions comprise at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 of the complement of the oligonucleotides listed in Tables 3 or FIG. 10 or 11. In some aspects, compositions comprise up to 150, 200, 250, 300, 350, 400, 450, 500, 1000, 2000, 3000, 4000, or 5000 of the complement of the oligonucleotides listed in Tables 3 or FIG. 10 or 11.

E. Kits

The materials described above as well as other materials can be packaged together in any suitable combination as a kit useful for performing, or aiding in the performance of, the disclosed method. The kit can be used for research use or for in vitro diagnosis (IVD). It is useful if the kit components in a given kit are designed and adapted for use together in the disclosed method. For example disclosed are kits for enriching non-host sequences from a host sample, the kit comprising non-host target primers. For example, disclosed are kits that can comprise one or more of the oligonucleotides of Tables 3, or 5-8. The kits also can contain polymerase or oligo d(T) primers. In some aspects, the oligo d(T) primers can be oligo d(T)-RNA polymerase promoter primers.

EXAMPLES

To make NGS technology a practical diagnostic tool in clinical labs, the key is to greatly increase the presence of pathogenic sequences in a clinical sample. To address this challenge, the Preferential Amplification of Pathogenic Sequences (PATHseq) technology was developed to preferentially amplify non-human sequences in a clinical sample. The strategy is based on the following rationales: 1) Active infection is the result of pathogenic gene expression, which produces polyadenylated RNAs (mRNAs), or pathogenic transcripts; 2) Only about 3% of human genome produce protein-coding transcripts (mRNAs), among these, the top 1,000 and 2,000 most abundant human transcripts comprise more than 65% and 72% of all human transcripts, respectively; 3) By selectively excluding the amplification of these abundant human transcripts, pathogenic transcripts can be preferentially amplified in human clinical samples; 4) Pathogenic transcripts can be further enriched through subtractive hybridization against a reference (normal) human transcription library (human transcriptome). The PATHseq technology, in combination with NGS technology, can provide comprehensive and unbiased diagnosis of pathogens responsible for any infectious disease The NGS technology has started a revolution in genomics and provided opportunities for its broad application in many fields, including in the diagnosis of human pathogens. However, prior to the methods described herein, NGS technology was still a research tool, rather than a diagnostic tool, due to the scarcity of pathogen sequences in human clinical samples and subsequent requirement of deep sequencing, and the complexity of bioinformatics analysis required to identify the pathogenic sequences. In order to address these challenges, current mainstream science focuses on three kinds of research: 1) Increasing the capacity of deep sequencing; 2) Increasing the capacity of bioinformatics analysis in order to identify the pathogenic sequences; 3) Hoping to use traditional methods to solve novel challenges (Table 1).

TABLE 1

List of current mainstream methods and their features

| Method | Application | Problem |
|---|---|---|
| Shortgun sequencing | Viral metagenome studies Microbiome studies | Remove host sequences Mapping pathogenic sequences |
| Amplicon sequencing with targeted PCR primers | Identify know human pathogens Identify mutations and variation | Unknown or novel pathogens Advantage over regular PCR? |
| Amplicon sequencing with random PCR primers | Amplification of enriched viral particles Discovery of new pathogens | Many viruses do not produce particles Remove host sequences |
| Enrichment through cell culture | Known pathogens Unknown pathogens grown on tissue | Not all pathogens can be cultured Method for unknown pathogen culture |

PATHseq is significantly different from mainstream science in that it focuses on how to increase the presence of pathogenic sequences in clinical samples through a new approach. For example, in PATHseq technology, a specific set of 8-mer primers, instead of random primers or pathogen-specific primers, are used to construct cDNA library. The 8-mer primers are short enough to amplify any pathogen sequence larger than 5,958 bp $((4^8 \times 8)/88)$, while selectively excluding the amplification of most abundant human transcripts. The pathogenic sequences can further be enriched by subtractive hybridization against reference human transcripts.

F. The Most Abundant Human Transcripts

One strategy for NGS application is to look at only the transcripts. Although the size of the human genome is huge (containing over 3 billion base pairs (bp)), it encodes only about 20,000 protein-coding genes, accounting for a very small fraction of the genome (approximately 2%). A recent report found that most protein-coding genes have one major transcript expressed at significantly higher levels than others, and in human tissues these major transcripts contribute almost 85 percent to the total mRNA. Given that the average length of human mRNAs is 1.3 kb, the complexity can be reduced by 26.8 times, if cDNA is sequenced instead of genomic DNA. This strategy has been used successfully by several publications in searching human pathogens and other applications. However, this strategy is still impractical for diagnostic laboratories, because the number of human transcripts is still too large compared to the relative scarcity of pathogenic transcripts.

In order to solve this problem, an alternative strategy using the most abundant human transcripts was used (Table 2). If the most abundant human transcripts are eliminated from clinical samples, the pathogenic sequences can be selectively enriched and further reduce the sequencing complexity. The recent completion of the Encyclopedia of DNA Elements (ENCODE) project provides a genome-wide "landscape of transcription in human cells" in 14 different cell lines. Based on the publicly available ENCODE database, the total human large transcripts (>200 bp polyadenylated RNAs) in GM12878 (a cell line that contributed most to the ENCODE database) are 161,999. Among these, 86,248 transcripts are reproducible (in a duplicated experiment). These 86,248 transcripts are defined as human transcriptome (Table 2). As shown in table 2, the most abundant 1,000 and 2,000 transcripts comprised about 65% and 72% of all human transcripts, respectively, based on ENCODE data.

TABLE 2

The most abundant human transcripts

| Most abundant human transcripts | RPKM | % of total human transcriptome |
|---|---|---|
| Top 1000 | 23391.45 | 65.52% |
| Top 2000 | 25847.42 | 72.40% |
| Top 3000 | 27355.52 | 76.62% |
| Top 4000 | 28440.66 | 79.66% |
| Top 5000 | 29287.62 | 82.04% |
| Top 6000 | 29973.64 | 83.96% |
| Top 7000 | 30544.67 | 85.56% |
| Top 8000 | 31035.38 | 86.93% |
| Top 9000 | 31463.82 | 88.13% |
| Top 10000 | 31838.97 | 89.18% |
| Top 20000 | 34018.78 | 95.29% |
| All 86248 | 35700.85 | 100% |

(RPKM: Reads per kilobase of transcript per million mapped reads)

G. Generation of a Set of Non-Human Target Primers that do not Match the Sequence of the Most Abundant Human Transcripts.

A computer program was further developed to look for specific patterns in the human transcriptome database. As predicted, human transcript sequences are not randomly distributed. Using this computer program, a set of 88 8-mer oligonucleotides (non-human target primers) (Table 3) were generated that do not match the sequences of the 2,000 most abundant human transcripts. In other words, by using this set of oligos as primers in the construction of cDNA library, 72% of human transcripts can be eliminated from clinical samples, greatly increasing the chance of selectively targeting pathogenic sequences. Theoretically, this set of primers has the probability to amplify any sequences larger than 5,958 bp (($4^8 \times 8$)/88), which include almost all human pathogens (both viruses and bacteria).

transcripts, for example, using the top 1000, or top 4000 human transcripts (FIG. 3). Whether it produces better results by using partial sequences of human transcripts (i.e. sequences from upstream 500 bp or 1,000 bp to 3'-end of transcripts) (FIG. 3) can also be tested. Whether this set will be different if the sequence data from a different cell line is used can be tested. The current technology is based on sequence data from GM12878, a blood cell line, therefore this approach is suitable for its application in blood donor screening, but may not be suitable for skin infection. In that case, the sequence data from an epithelial or endothelial cell line can be used. Currently, ENCODE database provides sequence data from 14 different cell lines.

I. Technology Development—Preferential Amplification of Pathogenic Sequences (PATHseq)

A technology, called PATHseq (FIG. 1) can be developed. This technology is based on the following rationale: 1) Active infection is the cause of pathogenic gene expression, which generates protein-coding transcripts or polyadenylated RNAs (mRNA); 2) By searching for pathogenic transcripts (mRNA) in the background of human transcriptome instead of genomic DNA, the sequencing complexity can be greatly reduced; 3) The 2,000 most abundant human transcripts comprise about 72% of all human transcripts and the use of a set of 8-mer primers can preferentially eliminate the amplification of these human transcripts; 4) Pathogenic sequences can be further enriched through subtractive hybridization against a human reference (non-pathogenic) cDNA library.

Total RNA or mRNAs can be purified from clinical samples (FIG. 1, step 1). Total RNA or mRNAs can be extracted and purified from clinical samples. Only RNAs larger than 200 bp are collected. Reverse transcription is shown in FIG. 1, step 2. A primer (P1) is designed to

TABLE 3

A list of 88 8-mer oligonucleotides (non-human target primers) that do not match the sequences of the 2,000 most abundant human transcripts

```
AAACGCGA ACGCGATA CCCTAACC CGCGATAC CGGTCGAT GTATAACG TAGCGTAT TCGAATAG

AACGCATA ATACCGGT CCGGTAAT CGCGCGTA CGTATATC GTTACGCG TAGTAACG TCGCGTAT

AATAACGC ATACGTAC CCGTAGTA CGCGGTTA CGTATTCG TAACCGTT TAGTCGAG TCGGTAAC

AATATCGT ATAGCGCA CGAACGTA CGCGTAAT CGTCGAAT TAACGTAA TAGTCGGT TCGTCGAT

AATATTCG ATAGCGCG CGAATAAC CGCGTATA CTAATACG TAAGCGCG TATAGCGC TCTAAGCG

AATCGGTA ATGCGATA CGACGTAC CGCGTATC CTTAGCGA TAAGCTCG TATCACGC TTAACGTA

ACACGTTA ATGCGTTA CGATAGGT CGCTAAAA GATACGTA TAATACGT TATCCGAC TTACGATA

ACCGGTTA ATTAGCGT CGATAGTA CGGGTCGA GCGAATAT TAGAGTCG TATCGCTA TTAGTCGA

ACGAACCG ATTGCGAC CGATATCC CGGTAAGC CCGACGTA TAGATCCG TATCGGAC TTATACCG

ACGAATAA ATTGTACG CGATCGTA CGGTAGAT GCGTAATT TAGCGAAT TATCGGTA TTATATCG

ACGATAGG CAATCGCG CGCAATAT CGGTAGTA GTACCGTA TAGCGTAC TATCGGTC TTATCGCG
```

H. Development and Test of a Set of 8-mer Oligonucleotides (Non-Human Target Primers) that do not Match the Sequence of the Most Abundant Human Transcripts.

The feasibility of using this set of oligos as primers to selectively amplify non-human sequences during construction of cDNA library can be tested. To make this set more efficient, these non-human target primers can be fine-tuned based on different sets of data of the most abundant human specifically transcribe mRNA into first-strand cDNAs (antisense) while introducing a T7 promoter/primer sequence into the cDNA. RNase H activity occurs at FIG. 1, step 3. The ribonuclease activity of RNase H cleaves RNA in a DNA/RNA duplex, allowing the synthesis of secondary cDNA strands. Synthesis of secondary cDNA strands is shown in FIG. 1, step 4. A set of 88 specific 8-mer oligonucleotides (Table 2) has been developed and can be used as primers for the synthesis of secondary cDNA strands. Because these primers do not amplify the 2,000 most abundant human mRNAs, about 72% of all human mRNAs can be eliminated from amplification, preferentially amplifying non-human (pathogenic) sequences.

Synthesis of RNAs is shown in FIG. 1, step 5. Using the T7 promoter introduced in FIG. 1, step 2, the T7 RNA polymerase synthesizes RNAs with double-stranded DNA as template. Anti-sense RNAs can be synthesized as shown in FIG. 1, step 6. Because the T7 promoter is attached to the poly(A) end, newly generated RNAs are anti-sense. Human reference cDNAs are used (FIG. 1, step 7). Human reference cDNA library can be created using the same set of 8-mer primers as in FIG. 1, step 4, plus a poly d(T) primer (not P1 primer). Normal (non-pathogenic) human mRNAs can be used as templates when the library is constructed. Sense strands of human reference cDNAs can be separated using poly d(T) beads. The beads are further used as solid phase for subtractive hybridization. Newly generated anti-sense human RNAs from FIG. 1, step 6 can be captured (hybridized) by these cDNAs and specifically degraded by RNase H in RNA-DNA hybrids. RNase H does not digest single or double-stranded DNA.

Enrichment of pathogenic RNAs is shown in FIG. 1, step 8. Pathogenic RNAs can be greatly enriched because they do not hybridize to human reference cDNAs. Reverse transcription occurs again as shown in FIG. 1, step 9. A poly d(T)-T7 promoter primer can be used to synthesize the first cDNA strands. Another round of RNase H activity occurs in FIG. 1, step 10. Again, RNase H cleaves RNAs in a DNA/RNA duplex.

RNA synthesis is shown in FIG. 1, step 11. Synthesized RNAs are anti-sense. Enrichment of pathogenic RNAs is shown in FIG. 1, step 12. Step 6 through 12 form a cycle in which pathogenic RNAs are repeatedly enriched. Through this process, the non-human (pathogenic) sequences can be increased by several orders of magnitude in the final samples for sequencing.

J. Next Generation Sequencing

The development of the NGS technologies have dramatically increased the capacity to sequence large genomes; now, a mammalian-sized genome can be sequenced with the time and affordability that would not have been feasible even a few years ago. NGS technology is following "Moore's Law" (a metric of technology improvement), with dramatic decreases in the cost per genome sequenced since its invention. New NGS instruments and platforms are coming to the market quickly. To determine the best possible NGS platform for the PATHseq technology, a comparison of current available NGS instruments was done (FIG. 4), modified from Glenn, T. C. 18 and updated from "2013 NGS Field Guide").

Among these available HGS platforms, the Illumina MiSeq, Ion Torrent Proton, and Oxford Nanopore can be good choices for diagnostic laboratories, based on the consideration of instrument cost, sequencing capacity, and running cost. For example, the Illumina MiSeq (Illumina, Calif.) has a capacity of 4 million reads per run while the second version has a capacity of 15 million reads with the length of reads up to 250+250 bp of PE (paired end), totaling the yield per run to 7,500 million by per run, about 6 times than the first version. The sequencing service fee has also decreased rapidly, with current price of $3,500 per lane using HiSeq 2500.

K. Multiplex Sequencing Per Run

The maximal number of samples that can be loaded onto one sequencing lane depends on two factors: 1) the minimal sequencing coverage required for successfully identifying a pathogen, usually the sequencing depth to achieve at least 1 RPKM (Reads per kilobase of transcript per million mapped reads) of pathogen sequences is required; 2) the capacity of the sequencing instrument. A single run of current HiSeq 2500 yields as many as 600 million reads (FIG. 4), each containing approximately 150 bases in length with paired ends (PE), totaling the yield to 180,000 Mbp. The second version of MiSeq platform has the capacity of 15 million reads per run and totaling the yield to 7,500 Mbp.

Based on this calculation, further reducing the sequencing cost per sample by introducing multiple sample identifiers (FIG. 4) can be achieved. Using the same computer program, a total of 40 10-mer oligonucleotides were generated that do not match the sequences to any of the total 161,999 human transcripts. These oligos can be divided into two sets and used as adaptors for the construction of sequencing libraries. The maximum combination of these 20+20 adaptors can generate 400 (20×20=400) sample identifiers (barcodes) from A1 to T20. Therefore, a total of maximum 400 samples can be separately labeled by these two sets of adaptors, mixed into one sample run for sequencing and then separated by its own sample identifier (barcode) from A1 to T20 (FIG. 5). Of course, the actual number of samples loaded into one sequencing lane may be fewer depending on different situation.

L. Computational Subtraction

The sequencing data can be analyzed by subtracting fragments that match human sequences and assembling them into contiguous sequences for direct comparison with the GenBank databases of nucleic acids using BLASTN software. By this method, any non-matching sequences representing potential pathogens can be enriched and remain in the final dataset.

M. Test of PATHseq Technology in Identification of Non-Human Sequences and Application in Diagnosis of Human Infection.

The PATHseq technology can be tested by imbedding pathogenic nucleic acid into human nucleic acid sample at different ratios of between $1:10^4$ and $1:10^{10}$ (pathogenic sequences:human sequences). Specific pathogenic sequences can then be preferentially amplified over human sequences. To accurately calculate the efficiency of this set of primers, quantitative PCR assay can be used to monitor the fold increase of imbedded pathogenic sequences. This technology can be used in the following fields.

PATHseq can be used for diagnosis of infectious diseases. The clinical specimens can be collected from routine test samples. PATHseq can quickly and accurately diagnose clinical specimens from unknown infections or from those samples with inconclusive results.

PATHseq can be used during investigation of infectious disease outbreaks and contributions to epidemiology studies. NGS technologies represent an evolving and rapidly changing field, with the potential to significantly reshape clinical practice and diagnosis of infectious diseases. NGS technology has been recently used to investigate outbreaks of drug-resistant bacteria in hospitals at the NIH Clinical Center and in the UK, as well as an outbreak of tuberculosis in Canada. Termed "genomic epidemiology," the NGS technology has the transformative potential to quickly pinpoint the origin of emerging diseases, the degree of antibiotic resistance of microbes, and the speed with which an infection moves through a population. By applying PATHseq technology in this field, the diagnosis of human pathogens can be improved by increasing the accuracy and speed with which the infectious diseases outbreaks can be characterized.

PATHseq can be used for blood donor screening. The development of increasingly sensitive and inclusive laboratory screening methods for blood products has greatly decreased the risk of transmission of many known pathogens through blood transfusion. However, transfusion is still not risk-free and the emergence of new pathogens continues to be potential threats to the blood supply. There are some limitations in the current screening test system for preventing transfusion-transmitted infections: 1) Current system requires some prior knowledge of the pathogen under investigation and therefore, cannot detect previously unknown pathogens; 2) Current system does not test for all potentially human pathogens due to the consideration of cost- and labor-efficiency; 3) Current system is already heavily burdened with multiple testing steps and more screening tests are likely to be added to the requirements in the future; 4) Current system is reactive to the occurrence of emerging pathogens after some patients are actually harmed and has a substantial delay before implementation; 5) Many donors who do not pose a risk to patients are temporarily or permanently deferred because of the impreciseness of current screening system which is based on risk evaluation of different groups. It is clear that a revolutionary screening test needs to be developed to sufficiently protect the safety of the blood supply while retain cost- and labor-efficiency. PATHseq can be a universal, one-step, and unbiased blood testing method to detect potential harmful pathogens (known or unknown) and guarantee a safe blood supply.

N. Preferential Amplification of Pathogenic Sequences

1. Human Transcriptome

Human transcriptome data was obtained from publicly available ENCODE (Encyclopedia of DNA Elements) database (http://encodeproject.org/ENCODE/). The total protein-coding human transcripts (>200 bp polyadenylated RNAs) detected by this study was 59,822, representing 18,939 genes expressed in at least one cell line (total studied cell lines are 14). The total human large transcripts identified in the cytosol of GM12878 cells (a cell line that contributed most to the ENCODE database) were 161,999. Among these, 86,248 transcripts were reproducible in the sequencing duplicate2. Therefore, 86,248 transcripts were defined as total human transcriptome. Previously, the Mammalian Gene Collection (MGC), a trans-NIH initiative, has identified a total of 29,818 human full-length protein-coding cDNA clones, representing 17,592 non-redundant human genes. MGC cDNA clones were obtained by screening of cDNA libraries, by transcript-specific RT-PCR cloning, and by DNA synthesis of cDNA inserts. The MGC database was also used in the study.

2. The Most Abundant Human Transcripts

The most abundant human transcripts were based on the sequencing data from cytosol portion of cell line GM12878, as calculated by RPKM (reads per kilobase of transcript per million mapped reads). As shown in Table 2, the top 1,000 and 2,000 most abundant human transcripts consist of 65.52% and 72.40% of total human transcripts, respectively.

3. Shortest Unmatched Sequences within Human Transcripts

A total of 86,248 transcripts were generated as human transcriptome based on ENCODE data in GM128782. To find out the shortest unmatched sequences within human transcripts, all shortest k-mers (substrings of length k) were then counted in human transcriptome sequencing data using a computer program described previously, with some modification. The computer program counted k-mers for a given k or the size of substring in a DNA sequence. It started from k=1, and checked if all of the possible k-mers occurred at least once. It stopped when it reached a k value where there was at least one k-mers that was not found as a substring in the set of transcripts. Table 4 lists the number of k-mer not found in human transcripts. FIG. 9 lists the percent of the sequences in the Virome covered by the oligos. For example, FIG. 9 shows that the top 10,000 human transcripts can be eliminated by using the 179 10-mers in FIG. 10 while covering all (100%) of known human viruses. By using the 171 10-mers in FIG. 11 the top 20,000 human transcripts can be eliminated while covering 95.477% of known human viruses.

TABLE 4

| | Number of k-mer not found in human transcripts | | | | | | | | | | | |
|---|---|---|---|---|---|---|---|---|---|---|---|---|
| | Top 1000 | Top 2000 | Top 3000 | Top 4000 | Top 5000 | Top 6000 | Top 7000 | Top 8000 | Top 9000 | Top 10000 | Top 20000 | All 86248 |
| 8-mer | 329 | 44 | 9 | 4 | 2 | 1 | 1 | 0 | 0 | 0 | 0 | 0 |
| 9-mer | 23473 | 8883 | 4402 | 2411 | 1493 | 953 | 651 | 455 | 347 | 249 | 28 | 1 |
| 10-mer | 351888 | 203816 | 139254 | 100542 | 76937 | 60510 | 49753 | 41374 | 35737 | 30336 | 10053 | 1075 |

4. Construction of cDNA Libraries and Subtractive Hybridization

A clinical specimen with bronchitis & pulmonary inflammation was collected. Total RNA was extracted using Qiagen's RNease Mini Kit (Catalog number: 74106, Qiagen, Valencia, Calif.) according to the product's protocol. cDNA library was constructed using NEB's T7 Quick High Yield RNA Synthesis Kit (Catalog number: E2050S, New England Biolabs, Ipswich, Mass.) with the following modification. First, the random primer mix in the kit was replaced by 88 8-mer oligonucleotides listed on Table 8. Second, the oligo d(T)23VN was replaced by a custom poly d(T) oligo, T7-d(T)18VN, which adds a T7 promoter/primer sequence to the 5'-end of poly d(T) sequence (5'-ACGGCCTAATACGACTCAC-TATAGGGTTTTTTTTTTTTTTTTTTVN-3'; SEQ ID NO:41) (FIG. 2). Third, M-MuLV Reverse Transcriptase was included in the reaction. Normal human cDNA library was constructed from peripheral blood mononuclear cells (PBMCs) with the same procedure.

Subtractive hybridization of cDNAs from clinical specimen against human normal cDNAs was carried out according to the protocol published previously with some modification (FIG. 1). Briefly, two enzymes (M-MuLV Reverse Transcriptase and T7 RNA polymerase) were used in the reaction, in addition to the custom primer, T7-d(T)18VN. Since M-MuLV Reverse Transcriptase possess RNAse H activity, the human transcripts resulting from the RNA-DNA duplex were degraded by M-MuLV Reverse Transcriptase. Each of the newly produced human or pathogen transcripts re-entered the subtractive hybridization process and served as a template for a new round of reverse transcription. The circulation of antisense transcripts resulted in exponential amplification of pathogenic transcripts (FIG. 1).

5. Next Generation Sequencing

NGS was performed using BGI sequencing service (BGI Americas, Cambridge, Mass.). Briefly, sample DNA was sheared into small fragments by nebulization. Overhangs resulting from fragmentation were filled into blunt ends by T4 DNA polymerase, Klenow fragment, and T4 polynucleotide kinase. After adding "A" base to the 3'-ends of the blunt phosphorylated DNA fragments, adapters were ligated to the ends of the small DNA fragments. Too short fragments were removed with Ampure beads (Beckman Coulter, Inc., Indianapolis Ind.) and the qualified DNA library was used for the sequencing.

Sequencing was carried out via the Illumina HiSeq2000 (Illumina, San Diego, Calif.). Read length was 101 PE (paired ends). Output was set to 3 Gb clean data. The actual raw reads was 3,206.25 Mb. The high quality reads was 3,100 Mb, representing approximately 15 million PE reads with 97% clean data.

6. Sequencing Data Analysis

Raw sequencing data was filtered by in-house scripts: 1) Remove reads with 3 N; 2) Remove reads contaminated by adapter (default: 15 bases overlapped by reads and adapter); 3) Remove reads with a certain proportion of low quality (20) bases (40% as default, parameter setting at 36 bp); 4) Remove duplication contamination.

Using a computer program called STAR, quality sequencing reads (approximately 15 million PE reads) were aligned against the human genome primarily assembled from ENSEMBL (uswest.ensembl.org/index.html). Reads aligned on multiple loci in the reference human genome were also considered as unmapped reads, and filtered out, which could reduce false positive rate. To obtain longer non-human origin reads, 729,313 unaligned reads were further assembled using a de novo assembly computer program named Trinity, resulting in 2067 contig sequences. The de novo assembled unaligned sequences were blasted against the nucleotide sequence database known as NCBI "nr" database. Finally, the assembled sequences were identified using the NCBI genomic BLAST database for "Microbes" including bacteria, fungi, and viruses.

7. 9-mer Non-Human Target Primers for the Construction of cDNA Library

In order to get rid of all human transcripts, or as many as possible from a clinical sample, a set of 9-mer oligos can be used. As shown in Table 7, there is one 9-mer oligo that does not match the full length of all human transcripts. However, this oligo is not ideal because the likelihood of finding a match for a 9-mer oligo in a random sequence is $4^9 \times 9 = 2,359,296$, which is larger than the genome size of many human pathogens. That means, by using this 9-mer oligo, even though it can get rid of all human transcript, it is less likely to pick up (amplify) most potential pathogen sequences.

To make this strategy work, the 3'-end sequences of all human transcripts are focused on. As shown in Table 6, there are 197 9-mer oligos that do not match the sequences from 500 bp upstream to the 3'-end of all human transcripts. In order to control the cDNA length to approximately 500 bp, a mixture of ddNTP (such as 1% ddATP, although this is adjustable) can be used with normal dNTP in the construction of first strand cDNA library. ddNTP lacks the OH needed to continue the elongation of the DNA strand. When ddATP is added to the reaction, the elongation of the strand will stop once the ddATP is added to the new strand. Using this set of 9-mer oligos, the likelihood to find a match in a non-human sequence is $4^9 \times 9/197 = 11,976$ bp. Most human pathogens have genome sizes larger, therefore, this strategy is feasible. Construction of a cDNA library can follow the same procedure as described above except 1% of ddATP (2',3'-Dideoxyadenosine 5'-Triphosphate, 100 MM Solution, GE Healthcare, Catalog number 27-2051-01) is added into dNTP solution.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention, which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

REFERENCES

1 Metzker, M. L. Sequencing technologies—the next generation. Nat Rev Genet 11, 31-46, doi:10.1038/nrg2626 (2010).
2 Shendure, J. & Ji, H. Next-generation DNA sequencing. Nat Biotechnol 26, 1135-1145, 1486 (2008).
3 Djebali, S. et al. Landscape of transcription in human cells. Nature 489, 101-108, nature11233 (2012).
4 Shendure, J. & Lieberman Aiden, E. The expanding scope of DNA sequencing. Nat Biotechnol 30, 1084-1094, doi: 10.1038/nbt.2421 (2012).
5 Feng, H., Shuda, M., Chang, Y. & Moore, P. S. Clonal integration of a polyomavirus in human Merkel cell carcinoma. Science 319, 1096-1100, doi:10.1126/science.1152586 (2008).
6 Palacios, G. et al. A New Arenavirus in a Cluster of Fatal Transplant-Associated Diseases. The New England journal of medicine (2008).
7 Consortium, E. P. et al. An integrated encyclopedia of DNA elements in the human genome. Nature 489, 57-74, doi:10.1038/nature11247 (2012).
8 Gonzalez-Porta, M., Frankish, A., Rung, J., Harrow, J. & Brazma, A. Transcriptome analysis of human tissues and cell lines reveals one dominant transcript per gene. Genome Biol 14, R70, doi:10.1186/gb-2013-14-7-r70 (2013).
9 Lander, E. S. et al. Initial sequencing and analysis of the human genome. Nature 409, 860-921, doi:10.1038/35057062 (2001).
10 Feng, H. et al. Human transcriptome subtraction by using short sequence tags to search for tumor viruses in conjunctival carcinoma. J Virol 81, 11332-11340 (2007).
11 Wheeler, D. A. et al. The complete genome of an individual by massively parallel DNA sequencing. Nature 452, 872-876 (2008).
12 von Bubnoff, A. Next-generation sequencing: the race is on. Cell 132, 721-723 (2008).
13 Mardis, E. R. The impact of next-generation sequencing technology on genetics. Trends Genet 24, 133-141 (2008).
14 Schuster, S. C. Next-generation sequencing transforms today's biology. Nat Methods 5, 16-18 (2008).
15 Shaffer, C. Next-generation sequencing outpaces expectations. Nat Biotechnol 25, 149 (2007).

16 Mardis, E. R. Anticipating the 1,000 dollar genome. Genome Biol 7, 112 (2006).
17 Metzker, M. L. Emerging technologies in DNA sequencing. Genome Res 15, 1767-1776 (2005).
18 Glenn, T. C. Field guide to next-generation DNA sequencers. Mol Ecol Resour 11, 759-769, doi:10.1111/j.1755-0998.2011.03024.x (2011).
19 Weber, G., Shendure, J., Tanenbaum, D. M., Church, G. M. & Meyerson, M. Identification of foreign gene sequences by transcript filtering against the human genome. Nat Genet 30, 141-142 (2002).
20 Xu, Y. et al. Pathogen discovery from human tissue by sequence-based computational subtraction. Genomics 81, 329-335 (2003).
21 Huang, X. & Madan, A. CAP3: A DNA sequence assembly program. Genome Res 9, 868-877 (1999).
22 Li, W. & Godzik, A. Cd-hit: a fast program for clustering and comparing large sets of protein or nucleotide sequences. Bioinformatics 22, 1658-1659 (2006).
23 Schmieder, R. & Edwards, R. Quality control and preprocessing of metagenomic datasets. Bioinformatics 27, 863-864, doi:10.1093/bioinformatics/btr026 (2011).
24 Dobin, A. et al. STAR: ultrafast universal RNA-seq aligner. Bioinformatics 29, 15-21, doi:10.1093/bioinformatics/bts635 (2013).
25 Grabherr, M. G. et al. Full-length transcriptome assembly from RNA-Seq data without a reference genome. Nat Biotechnol 29, 644-652, doi:10.1038/nbt.1883 (2011).
26 Morgulis, A. et al. Database indexing for production MegaBLAST searches. Bioinformatics 24, 1757-1764, doi:10.1093/bioinformatics/btn322 (2008).
27 Sayers, E. W. et al. Database resources of the National Center for Biotechnology Information. Nucleic Acids Res 38, D5-16, doi:10.1093/nar/gkp967 (2010).
28 Kupferschmidt, K. Epidemiology. Outbreak detectives embrace the genome era. Science 333, 1818-1819, doi:10.1126/science.333.6051.1818 (2011).
29 Alter, H. J., Stramer, S. L. & Dodd, R. Y. Emerging infectious diseases that threaten the blood supply. Semin Hematol 44, 32-41 (2007).
30 Holland, P. V. Viral infections and the blood supply. The NEJM 334, 1734-1735 (1996).
31 Schreiber, G. B., Busch, M. P., Kleinman, S. H. & Korelitz, J. J. The risk of transfusion-transmitted viral infections. The Retrovirus Epidemiology Donor Study. The New England journal of medicine 334, 1685-1690 (1996).
32. Consortium, E. P. et al. An integrated encyclopedia of DNA elements in the human genome. Nature 489, 57-74, doi:10.1038/nature11247 (2012).
33 Djebali, S. et al. Landscape of transcription in human cells. Nature 489, 101-108, doi:10.1038/nature11233 (2012).
34 Gerhard, D. S. et al. The status, quality, and expansion of the NIH full-length cDNA project: the Mammalian Gene Collection (MGC). Genome research 14, 2121-2127, doi:10.1101/gr.2596504 (2004).
35 Strausberg, R. L. et al. Generation and initial analysis of more than 15,000 full-length human and mouse cDNA sequences. Proceedings of the National Academy of Sciences of the United States of America 99, 16899-16903, doi:10.1073/pnas.242603899 (2002).
36 Strausberg, R. L., Feingold, E. A., Klausner, R. D. & Collins, F. S. The mammalian gene collection. Science 286, 455-457 (1999).
37 Team, M. G. C. P. et al. The completion of the Mammalian Gene Collection (MGC). Genome research 19, 2324-2333, doi:10.1101/gr.095976.109 (2009).
38 Marcais, G. & Kingsford, C. A fast, lock-free approach for efficient parallel counting of occurrences of k-mers. Bioinformatics 27, 764-770, doi:10.1093/bioinformatics/btr011 (2011).
39 Rizk, G., Lavenier, D. & Chikhi, R. DSK: k-mer counting with very low memory usage. Bioinformatics 29, 652-653, doi:10.1093/bioinformatics/btt020 (2013).
40 Chen, J. Serial analysis of binding elements for human transcription factors. Nat Protoc 1, 1481-1493 (2006).
41 Dobin, A. et al. STAR: ultrafast universal RNA-seq aligner. Bioinformatics 29, 15-21, doi:10.1093/bioinformatics/bts635 (2013).
42 Grabherr, M. G. et al. Full-length transcriptome assembly from RNA-Seq data without a reference genome. Nat Biotechnol 29, 644-652, doi:10.1038/nbt.1883 (2011).
43 Sayers, E. W. et al. Database resources of the National Center for Biotechnology Information. Nucleic Acids Res 38, D5-16, doi:10.1093/nar/gkp967 (2010).

We claim:

1. A method of enriching non-human nucleic acids from a human sample comprising selectively amplifying nucleic acids isolated from the human sample using non-human target primers to form an enriched population of non-human nucleic acids, wherein the non-human target primers are at least the oligonucleotides in FIG. 10 or FIG. 11.

2. The method of claim 1, wherein the nucleic acids isolated from the human sample are DNA.

3. The method of claim 1, wherein the nucleic acids isolated from the human sample are RNA.

4. The method of claim 1 further comprising performing subtractive hybridization against a population of reference human cDNAs, wherein the subtractive hybridization results in a further enriched population of non-human nucleic acids.

5. The method of claim 1, wherein the non-human nucleic acids are pathogenic sequences.

6. The method of claim 5, wherein the pathogenic sequences are from viruses, bacteria, fungi, or any infectious agents.

7. The method of claim 1, wherein the non-human target primers are designed based on their inability to bind to at least the top 1,000 human B cell transcripts.

8. The method of claim 7, wherein the top 1,000 human B cell transcripts comprise at least 65% of all human B cell transcripts.

9. The method of claim 7, wherein the top 1,000 human B cell transcripts are greater than 200 base pairs in length.

10. The method of claim 7, wherein the non-human target primers do not bind to at least the top 2000, 3000, 4000, 5000, 6000, 7000, 8000, 9000, 10000, 20000 human B cell transcripts or whole human B cell transcriptome.

11. A method of enriching non-human nucleic acids from a human sample comprising
hybridizing a set of non-human target primers to total RNA or mRNA isolated from the human sample and selectively reverse transcribing total RNA or mRNA isolated from the human sample to form an enriched population of non-human cDNA strands,
wherein the set of non-human target primers are the complement of at least the set of oligonucleotides in FIG. 10 or FIG. 11.

12. The method of claim 11 further comprising performing subtractive hybridization against a population of reference human cDNAs, wherein the subtractive hybridization results in a further enriched population of non-human cDNAs.

13. The method of claim 11, wherein the non-human target primers do not hybridize to at least the top 1,000 human B cell transcripts.

14. The method of claim 13, wherein the top 1,000 human transcripts comprise at least 65% of all human B cell transcripts.

15. The method of claim 13, wherein the top 1,000 human B cell transcripts are greater than 200 base pairs in length.

16. The method of claim 13, wherein the non-human target primers do not bind to at least the top 2000, 3000, 4000, 5000, 6000, 7000, 8000, 9000, 10000, 20000 human transcripts or whole human transcriptome.

17. The method of claim 11, wherein the non-human nucleic acids are pathogenic sequences.

18. The method of claim 17, wherein the pathogenic sequences are from viruses, bacteria, fungi, or any infectious agents.

19. A method of detecting non-host nucleic acids in a host sample comprising:
a) selectively amplifying nucleic acids isolated from the host sample using non-host target primers to form an enriched population of non-host nucleic acids,
wherein the non-host target primers are at least the oligonucleotides in FIG. 10 or FIG. 11; and
b) detecting the non-host nucleic acids by sequencing the enriched population of unknown, non-host nucleic acids.

20. The method of claim 19, further comprising performing subtractive hybridization against a reference population of host cDNAs, wherein the subtractive hybridization results in a further enriched population of cDNAs, wherein the subtractive hybridization occurs prior to step (b).

21. The method of claim 19, wherein the non-host nucleic acids are a pathogenic sequence.

22. The method of claim 21, wherein the pathogenic sequence is known or unknown.

23. The method of claim 21, wherein the pathogenic sequences are from viruses, bacteria, fungi, or any infectious agents.

24. The method of claim 19, wherein the top 1,000 human transcripts comprise at least 65% of all human B cell transcripts.

25. The method of claim 19, wherein the top 1,000 human B cell transcripts are greater than 200 base pairs in length.

26. The method of claim 19, wherein the non-human target primers do not bind to at least the top 2000, 3000, 4000, 5000, 6000, 7000, 8000, 9000, 10000, 20000 human B cell transcripts or whole human B cell transcriptome.

27. The method of claim 19, wherein the non-host target primers are designed based on their inability to bind to at least the top 1,000 human B cell transcripts.

* * * * *